United States Patent
Suh

(10) Patent No.: US 11,219,664 B2
(45) Date of Patent: Jan. 11, 2022

(54) COMPOSITION FOR DIAGNOSING, PREVENTING, OR TREATING VASCULAR SMOOTH MUSCLE CELL PROLIFERATIVE DISEASES USING FGF12

(71) Applicant: CHUNG-ANG UNIVERSITY INDUSTRY ACADEMIC COOPERATION FOUNDATION, Seoul (KR)

(72) Inventor: Wonhee Suh, Seongnam-si (KR)

(73) Assignee: CHUNG-ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 519 days.

(21) Appl. No.: 15/894,337

(22) Filed: Feb. 12, 2018

(65) Prior Publication Data

US 2018/0243374 A1 Aug. 30, 2018

Related U.S. Application Data

(63) Continuation-in-part of application No. PCT/KR2016/008575, filed on Aug. 3, 2016.

(30) Foreign Application Priority Data

Aug. 12, 2015 (KR) .......................... 10-2015-0113727

(51) Int. Cl.
| | | |
|---|---|---|
| *A61K 48/00* | (2006.01) | |
| *A61K 38/18* | (2006.01) | |
| *C12N 15/63* | (2006.01) | |
| *C12Q 1/686* | (2018.01) | |
| *G01N 33/68* | (2006.01) | |
| *C12Q 1/68* | (2018.01) | |
| *C12Q 1/6883* | (2018.01) | |
| *C07K 14/50* | (2006.01) | |

(52) U.S. Cl.
CPC .......... *A61K 38/1825* (2013.01); *C07K 14/50* (2013.01); *C12Q 1/68* (2013.01); *C12Q 1/6883* (2013.01); *G01N 33/6893* (2013.01); *A61K 48/00* (2013.01); *C12N 2710/10343* (2013.01); *C12N 2710/10371* (2013.01); *C12Q 2600/158* (2013.01); *G01N 2333/50* (2013.01); *G01N 2800/32* (2013.01); *G01N 2800/321* (2013.01)

(58) Field of Classification Search
None
See application file for complete search history.

(56) References Cited

U.S. PATENT DOCUMENTS 5,693,775 A * 12/1997 Nathans .................. A61P 27/02
536/23.1
2003/0166551 A1 9/2003 Matsuzawa et al.

FOREIGN PATENT DOCUMENTS

WO 2011/044927 A1 10/2009

OTHER PUBLICATIONS

Paulin et al., New therapeutics for pulmonary arterial hypertension: do gene therapies have translational values? Clin. Invest. (2011) 1(3), 363-366 N.*
Fumoto et al, Targeted Gene Delivery: Importance of Administration Routes, Chapter 1, Intech, 2013, pp. 3-31.*
Stegmann, TJ, Protein Therapy vs. Gene THerapy, DDNEWS, 2006, pp. 1-2.*
Auguero et al., Intratracheal Gene Delivery of SERCA2a Ameliorates Chronic Post-Capillary Pulmonary Hypertension, J Am Coll Cardiol 2016;67:2032-46.*
Reynolds, PN, Gene therapy for pulmonary hypertension: prospects and challenges, Expert Opinion on Biological Therapy, 11:2, 133-143, 2011.*
Materials and Methods, supplementary data from Arteriosclerosis, Thrombosis, and Vascular Biologyvol. 36, Issue 9, Sep. 2016, pp. 1-4.*
Tables, supplementary data from Arteriosclerosis, Thrombosis, and Vascular Biologyvol. 36, Issue 9, Sep. 2016, pp. 1-2.*
Chan et al., Fibroblast Growth Factor-10 Promotes Cardiomyocyte Differentiation from Embryonic and Induced Pluripotent Stem Cells, PLoS One, pp. 1-12, 2010.*
Pablo et al., "Fibroblast Growth Factor Homologous Factors: New Roles in Neuronal Health and Disease", The Neuroscientist, 2016, vol. 22, No. 1, pp. 19-25 (total 7 pages).
Hitzeman et al., "Isolation and Characterization of the Yeast 3-Phosphoglycerokinase Gene (PGK) by an Immunological Screening Technique", The Journal of Biological Chemistry, Dec. 25, 1980, vol. 255, No. 24, pp. 12073-12080 (total 8 pages).
Archer et al., "Basic Science of Pulmonary Arterial Hypertension for Clinicians New Concepts and Experimental Therapies", Circulation, American Heart Association, May 11, 2010, pp. 2045-2066 (total 22 pages).
Mingming Zhang, Md et al., "Regulation of Smooth Muscle Contractility by Competing Endogenous mRNAs in Intracranial Aneurysms", Journal of Neuropathology and Experimental Neurology, May 2015, pp. 411-424, vol. 74, No. 5.
"Human fibroblast growth factor homologous factor 1 (FHF-1) mRNA, complete cds", NCBI, GenBank accession No. U66197.1, Nov. 15, 1996.
Chistiakov, et al., "Vascular smooth muscle cell in atherosclerosis", Acta Physiologica, 2015, pp. 33-50, vol. 214.

(Continued)

*Primary Examiner* — Maria Marvich
(74) *Attorney, Agent, or Firm* — Sughrue Mion, PLLC

(57) ABSTRACT

The present invention directs to a method for treating a smooth muscle cell proliferative disease by using a recombinant expression vector comprising a polynucleotide encoding FGF12, or by using FGF12 protein or a fragment thereof; and a method for detecting a marker for diagnosis of smooth muscle cell proliferative disease, comprising the measurement of FGF12 expression level.

10 Claims, 27 Drawing Sheets
(16 of 27 Drawing Sheet(s) Filed in Color)
Specification includes a Sequence Listing.

(56) References Cited

OTHER PUBLICATIONS

Sun-Hwa Song, et al., "Fibroblast Growth Factor 12 is a Novel Regulator of Vascular Smooth Muscle Cell Plasticity and Fate", Arteriosclerosis, Thrombosis, and Vascular Biology, Jul. 28, 2016, pp. 1928-1936, vol. 36.
Genbank, "*Homo sapiens* fibroblast growth factor 12 (FGF12), transcript variant 1, mRNA", NCBI Reference Sequence: NM_021032.4, 2020, 4 pages.
Genbank, "*Homo sapiens* fibroblast growth factor 12 (FGF12), transcript variant 2, mRNA", NCBI Reference Sequence: NM_004113.5, 2020, 4 pages.

* cited by examiner

SEQUENCE LISTING

```
<160> NUMBER OF SEQ ID NOS: 57

<210> SEQ ID NO 1
<211> LENGTH: 732
<212> TYPE: RNA
<213> ORGANISM: artificial sequence
<220> FEATURE:
<223> OTHER INFORMATION: human FGF12 isoform 1 mRNA

<400> SEQUENCE: 1
auggcugcgg cgauagccag cuccuugauc cggcagaagc ggcaggcgag ggaguccaac      60
agcgaccgag ugucggccuc caagcgccgc uccagcccca gcaaagacgg gcgcucccug     120
ugcgagaggc acguccucgg gguguucagc aaagugcgcu ucugcagcgg ccgcaagagg     180
ccggugaggc ggagaccaga accccagcuc aaagggauug ugacaagguu auucagccag     240
cagggauacu uccugcagau gcacccagau gguaccauug augggaccaa ggacgaaaac     300
agcgacuaca cucucuucaa ucuaauuccc gugggccugc guguagugc cauccaagga     360 gugaaggcua gccucuaugu ggccaugaau ggugaaggcu aucucuacag uucagauguu     420
uucacuccag aaugcaaauu caaggaaucu guguuugaaa acuacuaugu gaucuauucu     480
uccacacugu accgccagca agaaucaggc cgagcuuggu uucugggacu caauaaagaa     540
ggucaaauua ugaagggaa cagagugaag aaaaccaagc ccucaucaca uuuuguaccg     600
aaaccuauug aagugguau guacagagaa ccaucgcuac augaaauugg agaaaaacaa     660
gggcguucaa ggaaaaguuc uggaacacca accaugaaug gaggcaaagu ugugaaucaa     720
gauucaacau ag                                                         732

<210> SEQ ID NO 2
<211> LENGTH: 243
<212> TYPE: PRT
<213> ORGANISM: artificial sequence
<220> FEATURE:
<223> OTHER INFORMATION: human FGF12 isoform 1 protein
```

<400> SEQUENCE: 2

| | | | | | | | | | | | | | | | |
|---|---|---|---|---|---|---|---|---|---|---|---|---|---|---|---|
|Met|Ala|Ala|Ala|Ile|Ala|Ser|Ser|Leu|Ile|Arg|Gln|Lys|Arg|Gln|Ala|
|1| | | |5| | | | |10| | | | |15| |
|Arg|Glu|Ser|Asn|Ser|Asp|Arg|Val|Ser|Ala|Ser|Lys|Arg|Arg|Ser|Ser|
| | | | |20| | | | |25| | | | |30| |
|Pro|Ser|Lys|Asp|Gly|Arg|Ser|Leu|Cys|Glu|Arg|His|Val|Leu|Gly|Val|
| | | | |35| | | | |40| | | | |45| |
|Phe|Ser|Lys|Val|Arg|Phe|Cys|Ser|Gly|Arg|Lys|Arg|Pro|Val|Arg|Arg|
| | | | |50| | | | |55| | | | |60| |
|Arg|Pro|Glu|Pro|Gln|Leu|Lys|Gly|Ile|Val|Thr|Arg|Leu|Phe|Ser|Gln|
|65| | | | |70| | | | |75| | | | |80|
|Gln|Gly|Tyr|Phe|Leu|Gln|Met|His|Pro|Asp|Gly|Thr|Ile|Asp|Gly|Thr|
| | | | |85| | | | |90| | | | |95| |
|Lys|Asp|Glu|Asn|Ser|Asp|Tyr|Thr|Leu|Phe|Asn|Leu|Ile|Pro|Val|Gly|
| | | | |100| | | | |105| | | | |110| |
|Leu|Arg|Val|Val|Ala|Ile|Gln|Gly|Val|Lys|Ala|Ser|Leu|Tyr|Val|Ala|
| | | | |115| | | | |120| | | | |125| |
|Met|Asn|Gly|Glu|Gly|Tyr|Leu|Tyr|Ser|Ser|Asp|Val|Phe|Thr|Pro|Glu|
| | | |130| | | | |135| | | | |140| | |
|Cys|Lys|Phe|Lys|Glu|Ser|Val|Phe|Glu|Asn|Tyr|Tyr|Val|Ile|Tyr|Ser|
|145| | | | |150| | | | |155| | | | |160|
|Ser|Thr|Leu|Tyr|Arg|Gln|Glu|Ser|Gly|Arg|Ala|Trp|Phe|Leu|Gly|
| | | | |165| | | | |170| | | | |175| |
|Leu|Asn|Lys|Glu|Gly|Gln|Ile|Met|Lys|Gly|Asn|Arg|Val|Lys|Lys|Thr|
| | | | |180| | | | |185| | | | |190| |
|Lys|Pro|Ser|Ser|His|Phe|Val|Pro|Lys|Pro|Ile|Glu|Val|Cys|Met|Tyr|
| | | | |195| | | | |200| | | | |205| |
|Arg|Glu|Pro|Ser|Leu|His|Glu|Ile|Gly|Glu|Lys|Gln|Gly|Arg|Ser|Arg|
| | | |210| | | | |215| | | | |220| | |
|Lys|Ser|Ser|Gly|Thr|Pro|Thr|Met|Asn|Gly|Gly|Lys|Val|Val|Asn|Gln|
|225| | | | |230| | | | |235| | | | |240|
|Asp|Ser|Thr| | | | | | | | | | | | | |

<210> SEQ ID NO 3
<211> LENGTH: 546
<212> TYPE: RNA
<213> ORGANISM: artificial sequence
<220> FEATURE:
<223> OTHER INFORMATION: human FGF12 isoform 2 mRNA

<400> SEQUENCE: 3

```
auggagagca agaaccccca gcucaaaggg auugugacaa gguuauucag ccagcaggga      60
uacuuccugc agaugcaccc agauggutacc auugauggga ccaaggacga aaacagcgac    120
uacacucucu ucaaucuaau ucccgugggc cugcguguag uggccauucca aggagugaag    180
gcuagccucu augguggccau gaauggugaa ggcuaucucu acaguucaga uguuuucacu    240
ccagaaugca aauucaagga aucuguguuu gaaaacuacu augugaucua uucuuccaca    300
cuguaccgcc agcaagaauc aggccgagcu ugguuucugg gacucaauaa agaaggucaa    360
auuaugaagg ggaacagagu gaagaaaacc aagcccucau cacauuuugu accgaaaccu    420
auugaagugu guauuacag agaaccaucg cuacaugaaa uuggagaaaa acaagggcgu    480
ucaaggaaaa guucuggaac accaaccaug aauggaggca aguugugaa ucaagauuca    540
acauag                                                                546
```

<210> SEQ ID NO 4
<211> LENGTH: 181
<212> TYPE: PRT
<213> ORGANISM: artificial sequence
<220> FEATURE:
<223> OTHER INFORMATION: human FGF12 isoform 2 protein

<400> SEQUENCE: 4

```
Met Glu Ser Lys Glu Pro Gln Leu Lys Gly Ile Val Thr Arg Leu Phe
1               5                   10                  15

Ser Gln Gln Gly Tyr Phe Leu Gln Met His Pro Asp Gly Thr Ile Asp
            20                  25                  30

Gly Thr Lys Asp Glu Asn Ser Asp Tyr Thr Leu Phe Asn Leu Ile Pro
        35                  40                  45

Val Gly Leu Arg Val Val Ala Ile Gln Gly Val Lys Ala Ser Leu Tyr
50                  55                  60

Val Ala Met Asn Gly Glu Gly Tyr Leu Tyr Ser Ser Asp Val Phe Thr
65                  70                  75                  80

Pro Glu Cys Lys Phe Lys Glu Ser Val Phe Glu Asn Tyr Tyr Val Ile
                85                  90                  95

Tyr Ser Ser Thr Leu Tyr Arg Gln Gln Glu Ser Gly Arg Ala Trp Phe
            100                 105                 110

Leu Gly Leu Asn Lys Glu Gly Gln Ile Met Lys Gly Asn Arg Val Lys
        115                 120                 125

Lys Thr Lys Pro Ser Ser His Phe Val Pro Lys Pro Ile Glu Val Cys
    130                 135                 140

Met Tyr Arg Glu Pro Ser Leu His Glu Ile Gly Glu Lys Gln Gly Arg
145                 150                 155                 160

Ser Arg Lys Ser Ser Gly Thr Pro Thr Met Asn Gly Gly Lys Val Val
                165                 170                 175

Asn Gln Asp Ser Thr
            180
```

<210> SEQ ID NO 5
<211> LENGTH: 20
<212> TYPE: DNA
<213> ORGANISM: artificial sequence
<220> FEATURE:
<223> OTHER INFORMATION: rat FGF12 forward

<400> SEQUENCE: 5
gcgatagcca gctccttgat                                                   20

<210> SEQ ID NO 6
<211> LENGTH: 20
<212> TYPE: DNA
<213> ORGANISM: artificial sequence
<220> FEATURE:
<223> OTHER INFORMATION: rat FGF12 reverse

<400> SEQUENCE: 6
gaagcgcact ttgctgaaca                                                   20

<210> SEQ ID NO 7
<211> LENGTH: 20
<212> TYPE: DNA
<213> ORGANISM: artificial sequence
<220> FEATURE:
<223> OTHER INFORMATION: rat SM-MHC forward

```
<400> SEQUENCE: 7
aaagccagat gtccgaagca                                              20

<210> SEQ ID NO 8
<211> LENGTH: 20
<212> TYPE: DNA
<213> ORGANISM: artificial sequence
<220> FEATURE:
<223> OTHER INFORMATION: rat SM-MHC reverse

<400> SEQUENCE: 8
agatctgcta ctggggtgga                                              20

<210> SEQ ID NO 9
<211> LENGTH: 21
<212> TYPE: DNA
<213> ORGANISM: artificial sequence
<220> FEATURE:
<223> OTHER INFORMATION: rat SM22a forward

<400> SEQUENCE: 9
accaagcctt ttctgcctca a                                            21

<210> SEQ ID NO 10
<211> LENGTH: 20
<212> TYPE: DNA
<213> ORGANISM: artificial sequence
<220> FEATURE:
<223> OTHER INFORMATION: rat SM22a reverse

<400> SEQUENCE: 10
ggttctcagg caccttcact                                              20

<210> SEQ ID NO 11
<211> LENGTH: 20
<212> TYPE: DNA
<213> ORGANISM: artificial sequence
<220> FEATURE:
<223> OTHER INFORMATION: rat SRF forward

<400> SEQUENCE: 11
acgaccttca gcaagaggaa                                              20

<210> SEQ ID NO 12
<211> LENGTH: 20
<212> TYPE: DNA
<213> ORGANISM: artificial sequence
<220> FEATURE:
<223> OTHER INFORMATION: rat SRF reverse

<400> SEQUENCE: 12
gagagtctgg cgagttgagg                                              20

<210> SEQ ID NO 13
<211> LENGTH: 20
<212> TYPE: DNA
<213> ORGANISM: artificial sequence
<220> FEATURE:
<223> OTHER INFORMATION: rat GAPDH forward

<400> SEQUENCE: 13
ctcatgacca cagtccatgc                                              20

<210> SEQ ID NO 14
<211> LENGTH: 20
```

```
<212> TYPE: DNA
<213> ORGANISM: artificial sequence
<220> FEATURE:
<223> OTHER INFORMATION: rat GAPDH reverse

<400> SEQUENCE: 14
ttcagctctg ggatgacctt                                               20

<210> SEQ ID NO 15
<211> LENGTH: 20
<212> TYPE: DNA
<213> ORGANISM: artificial sequence
<220> FEATURE:
<223> OTHER INFORMATION: human FGF12 (total) forward

<400> SEQUENCE: 15
gcgatagcca gctccttgat                                               20

<210> SEQ ID NO 16
<211> LENGTH: 20
<212> TYPE: DNA
<213> ORGANISM: artificial sequence
<220> FEATURE:
<223> OTHER INFORMATION: human FGF12 (total) reverse

<400> SEQUENCE: 16
gaagcgcact ttgctgaaca                                               20

<210> SEQ ID NO 17
<211> LENGTH: 20
<212> TYPE: DNA
<213> ORGANISM: artificial sequence
<220> FEATURE:
<223> OTHER INFORMATION: human FGF12 (exo) forward

<400> SEQUENCE: 17
agcttggttt ctgggactca                                               20

<210> SEQ ID NO 18
<211> LENGTH: 24
<212> TYPE: DNA
<213> ORGANISM: artificial sequence
<220> FEATURE:
<223> OTHER INFORMATION: human FGF12 (exo) reverse

<400> SEQUENCE: 18
ctcttctgag atgagtttct gctc                                          24

<210> SEQ ID NO 19
<211> LENGTH: 20
<212> TYPE: DNA
<213> ORGANISM: artificial sequence
<220> FEATURE:
<223> OTHER INFORMATION: human (CDK1) forward

<400> SEQUENCE: 19
aaactggctg attttggcct                                               20

<210> SEQ ID NO 20
<211> LENGTH: 20
<212> TYPE: DNA
<213> ORGANISM: artificial sequence
<220> FEATURE:
<223> OTHER INFORMATION: human (CDK1) reverse
```

```
<400> SEQUENCE: 20
ggagtgccca aagctctgaa                                                    20

<210> SEQ ID NO 21
<211> LENGTH: 20
<212> TYPE: DNA
<213> ORGANISM: artificial sequence
<220> FEATURE:
<223> OTHER INFORMATION: human (CDK2) forward

<400> SEQUENCE: 21
ctccagggcc tagctttctg                                                    20

<210> SEQ ID NO 22
<211> LENGTH: 20
<212> TYPE: DNA
<213> ORGANISM: artificial sequence
<220> FEATURE:
<223> OTHER INFORMATION: human (CDK2) reverse

<400> SEQUENCE: 22
ttcaggagct cggtaccaca                                                    20

<210> SEQ ID NO 23
<211> LENGTH: 20
<212> TYPE: DNA
<213> ORGANISM: artificial sequence
<220> FEATURE:
<223> OTHER INFORMATION: human CCNA2 forward

<400> SEQUENCE: 23
tgcatctctg ggcgtctttg                                                    20

<210> SEQ ID NO 24
<211> LENGTH: 20
<212> TYPE: DNA
<213> ORGANISM: artificial sequence
<220> FEATURE:
<223> OTHER INFORMATION: human CCNA2 reverse

<400> SEQUENCE: 24
acccggccaa agaatagtcg                                                    20

<210> SEQ ID NO 25
<211> LENGTH: 20
<212> TYPE: DNA
<213> ORGANISM: artificial sequence
<220> FEATURE:
<223> OTHER INFORMATION: human CDC6 forward

<400> SEQUENCE: 25
aagggcgttg gggtcataag                                                    20

<210> SEQ ID NO 26
<211> LENGTH: 20
<212> TYPE: DNA
<213> ORGANISM: artificial sequence
<220> FEATURE:
<223> OTHER INFORMATION: human CDC6 reverse

<400> SEQUENCE: 26
ggcttcatct aagggcagca                                                    20
```

<210> SEQ ID NO 27
<211> LENGTH: 20
<212> TYPE: DNA
<213> ORGANISM: artificial sequence
<220> FEATURE:
<223> OTHER INFORMATION: human CDC20 forward

<400> SEQUENCE: 27
gcaagctctg gtgacatcct                                               20

<210> SEQ ID NO 28
<211> LENGTH: 20
<212> TYPE: DNA
<213> ORGANISM: artificial sequence
<220> FEATURE:
<223> OTHER INFORMATION: human CDC20 reverse

<400> SEQUENCE: 28
acatggtgtt ctgctacccg                                               20

<210> SEQ ID NO 29
<211> LENGTH: 22
<212> TYPE: DNA
<213> ORGANISM: artificial sequence
<220> FEATURE:
<223> OTHER INFORMATION: human SM MHC forward

<400> SEQUENCE: 29
atgaggccac ggagagcaac ga                                            22

<210> SEQ ID NO 30
<211> LENGTH: 21
<212> TYPE: DNA
<213> ORGANISM: artificial sequence
<220> FEATURE:
<223> OTHER INFORMATION: human SM MHC reverse

<400> SEQUENCE: 30
ccattgaagt ctgcgtctcg a                                             21

<210> SEQ ID NO 31
<211> LENGTH: 21
<212> TYPE: DNA
<213> ORGANISM: artificial sequence
<220> FEATURE:
<223> OTHER INFORMATION: human p53 forward

<400> SEQUENCE: 31
agcgatggtc tggcccctcc t                                             21

<210> SEQ ID NO 32
<211> LENGTH: 21
<212> TYPE: DNA
<213> ORGANISM: artificial sequence
<220> FEATURE:
<223> OTHER INFORMATION: human p53 reverse

<400> SEQUENCE: 32
ctcaggcggc tcatagggca c                                             21

<210> SEQ ID NO 33
<211> LENGTH: 20
<212> TYPE: DNA
<213> ORGANISM: artificial sequence
<220> FEATURE:

```
<223> OTHER INFORMATION: human p21 forward

<400> SEQUENCE: 33
ttgccgacag gatgcagaag                                          20

<210> SEQ ID NO 34
<211> LENGTH: 20
<212> TYPE: DNA
<213> ORGANISM: artificial sequence
<220> FEATURE:
<223> OTHER INFORMATION: human p21 reverse

<400> SEQUENCE: 34
aggtggacag cgaggccagg                                          20

<210> SEQ ID NO 35
<211> LENGTH: 19
<212> TYPE: DNA
<213> ORGANISM: artificial sequence
<220> FEATURE:
<223> OTHER INFORMATION: human GAPDH forward

<400> SEQUENCE: 35
gaaggtgaag gtcggagtc                                           19

<210> SEQ ID NO 36
<211> LENGTH: 19
<212> TYPE: DNA
<213> ORGANISM: artificial sequence
<220> FEATURE:
<223> OTHER INFORMATION: human GAPDH reverse

<400> SEQUENCE: 36
gaagatggtg atgggatttc                                          19

<210> SEQ ID NO 37
<211> LENGTH: 19
<212> TYPE: RNA
<213> ORGANISM: artificial sequence
<220> FEATURE:
<223> OTHER INFORMATION: human FGF12 siRNA #1 (5'->3')

<400> SEQUENCE: 37
aaacaagggc guucaagga                                           19

<210> SEQ ID NO 38
<211> LENGTH: 19
<212> TYPE: RNA
<213> ORGANISM: artificial sequence
<220> FEATURE:
<223> OTHER INFORMATION: human FGF12 siRNA #2 (5'->3')

<400> SEQUENCE: 38
ggugaaggcu aucucuaca                                           19

<210> SEQ ID NO 39
<211> LENGTH: 19
<212> TYPE: RNA
<213> ORGANISM: artificial sequence
<220> FEATURE:
<223> OTHER INFORMATION: human FGF12 siRNA #3 (5'->3')

<400> SEQUENCE: 39
aaccaucgcu acaugaaau                                           19
```

```
<210> SEQ ID NO 40
<211> LENGTH: 19
<212> TYPE: RNA
<213> ORGANISM: artificial sequence
<220> FEATURE:
<223> OTHER INFORMATION: human FGF12 siRNA #4 (5'->3')

<400> SEQUENCE: 40
cuauugaagu guguaugua                                                   19

<210> SEQ ID NO 41
<211> LENGTH: 19
<212> TYPE: RNA
<213> ORGANISM: artificial sequence
<220> FEATURE:
<223> OTHER INFORMATION: human p53 siRNA #1 (5'->3')

<400> SEQUENCE: 41
gaaauuugcg uguggagua                                                   19

<210> SEQ ID NO 42
<211> LENGTH: 19
<212> TYPE: RNA
<213> ORGANISM: artificial sequence
<220> FEATURE:
<223> OTHER INFORMATION: human p53 siRNA #2 (5'->3')

<400> SEQUENCE: 42
gugcagcugu ggguugauu                                                   19

<210> SEQ ID NO 43
<211> LENGTH: 19
<212> TYPE: RNA
<213> ORGANISM: artificial sequence
<220> FEATURE:
<223> OTHER INFORMATION: human p53 siRNA #3 (5'->3')

<400> SEQUENCE: 43
gcagucagau ccuagcguc                                                   19

<210> SEQ ID NO 44
<211> LENGTH: 19
<212> TYPE: RNA
<213> ORGANISM: artificial sequence
<220> FEATURE:
<223> OTHER INFORMATION: human p53 siRNA #4 (5'->3')

<400> SEQUENCE: 44
ggagaauauu ucacccuuc                                                   19

<210> SEQ ID NO 45
<211> LENGTH: 21
<212> TYPE: RNA
<213> ORGANISM: artificial sequence
<220> FEATURE:
<223> OTHER INFORMATION: control siRNA (5'->3')

<400> SEQUENCE: 45
aauggaagac cacucccacu c                                                21

<210> SEQ ID NO 46
<211> LENGTH: 20
<212> TYPE: DNA
<213> ORGANISM: Artificial Sequence
<220> FEATURE:
<223> OTHER INFORMATION: human ID3 forward
```

```
<400> SEQUENCE: 46
gaggcactca gcttagccag                                              20

<210> SEQ ID NO 47
<211> LENGTH: 21
<212> TYPE: DNA
<213> ORGANISM: Artificial Sequence
<220> FEATURE:
<223> OTHER INFORMATION: human ID3 reverse

<400> SEQUENCE: 47
atgacaagtt ccggagtgag c                                            21

<210> SEQ ID NO 48
<211> LENGTH: 20
<212> TYPE: DNA
<213> ORGANISM: Artificial Sequence
<220> FEATURE:
<223> OTHER INFORMATION: human a-SMA forward

<400> SEQUENCE: 48
agcgacccta aagcttccca                                              20

<210> SEQ ID NO 49
<211> LENGTH: 20
<212> TYPE: DNA
<213> ORGANISM: Artificial Sequence
<220> FEATURE:
<223> OTHER INFORMATION: human a-SMA reverse

<400> SEQUENCE: 49
catagagaga cagcaccgcc                                              20

<210> SEQ ID NO 50
<211> LENGTH: 20
<212> TYPE: DNA
<213> ORGANISM: Artificial Sequence
<220> FEATURE:
<223> OTHER INFORMATION: human SM22a forward

<400> SEQUENCE: 50
ggagcagtgg gtgcatttca                                              20

<210> SEQ ID NO 51
<211> LENGTH: 20
<212> TYPE: DNA
<213> ORGANISM: Artificial Sequence
<220> FEATURE:
<223> OTHER INFORMATION: human SM22a reverse

<400> SEQUENCE: 51
tgcactagcc aagtcatccg                                              20

<210> SEQ ID NO 52
<211> LENGTH: 20
<212> TYPE: DNA
<213> ORGANISM: Artificial Sequence
<220> FEATURE:
<223> OTHER INFORMATION: human BMPR2 forward

<400> SEQUENCE: 52
aggaagataa tgcagccata                                              20

<210> SEQ ID NO 53
<211> LENGTH: 20
```

```
<212> TYPE: DNA
<213> ORGANISM: Artificial Sequence
<220> FEATURE:
<223> OTHER INFORMATION: human BMPR2 reverse

<400> SEQUENCE: 53
tgggaagagg tctgtacatc                                               20

<210> SEQ ID NO 54
<211> LENGTH: 19
<212> TYPE: RNA
<213> ORGANISM: Artificial Sequence
<220> FEATURE:
<223> OTHER INFORMATION: human BMPR2 siRNA #1

<400> SEQUENCE: 54
gaacgcaacc ugucacaua                                                19

<210> SEQ ID NO 55
<211> LENGTH: 19
<212> TYPE: RNA
<213> ORGANISM: Artificial Sequence
<220> FEATURE:
<223> OTHER INFORMATION: human BMPR2 siRNA #2

<400> SEQUENCE: 55
gcaugagccu uuacugaga                                                19

<210> SEQ ID NO 56
<211> LENGTH: 19
<212> TYPE: RNA
<213> ORGANISM: Artificial Sequence
<220> FEATURE:
<223> OTHER INFORMATION: human BMPR2 siRNA #3

<400> SEQUENCE: 56
gaaacaagua gacauguau                                                19

<210> SEQ ID NO 57
<211> LENGTH: 19
<212> TYPE: RNA
<213> ORGANISM: Artificial Sequence
<220> FEATURE:
<223> OTHER INFORMATION: human BMPR2 siRNA #4

<400> SEQUENCE: 57
gaagguggcc gaacuaauu                                                19
```

COMPOSITION FOR DIAGNOSING, PREVENTING, OR TREATING VASCULAR SMOOTH MUSCLE CELL PROLIFERATIVE DISEASES USING FGF12

CROSS-REFERENCE TO RELATED APPLICATIONS

This application is a continuation-in-part of International Application No. PCT/KR2016/008575, filed on Aug. 3, 2016, and claims the benefit of and priority from Korean Patent Application No. 10-2015-0113727, filed on Aug. 12, 2015, all of which are hereby incorporated by reference for all purpose as if fully set forth herein.

BACKGROUND

Field

The present invention relates to a composition for treating a vascular smooth muscle cell proliferative disease, a composition for diagnosing the same, and a method for detecting a diagnostic marker and, more specifically, to a composition for treating a vascular smooth muscle cell proliferative disease, the composition comprising, as an active ingredient, a recombinant expression vector comprising a polynucleotide encoding FGF12 or FGF12 protein or a fragment thereof; to a composition for diagnosing a vascular smooth muscle cell proliferative disease, the composition comprising an agent for measuring the expression level of FGF12 mRNA or FGF12 protein; and to a method for detecting a marker for a vascular smooth muscle cell proliferative disease using the same.

Discussion of the Background

Vascular smooth muscle cells form and support vascular structures and are very important in repeating relaxation and contraction through the regulation of autonomic nervous systems and hormones to achieve smooth blood circulation. Vascular smooth muscle cells highly express smooth muscle-specific genes, such as SMA, SM22α, SM-MHC, SM-calponin, and desmin and hardly proliferate in a healthy and normal condition, but actively proliferate and migrate, as a part of a remodeling procedure for restoring vascular injury in a situation where vascular injury due to vascular wounds, atherosclerosis, inflammation, or other vascular diseases needs to be restored. When the proliferation of vascular smooth muscle cells is not normally regulated and occurs excessively due to abnormal signaling or repetitive injury, smooth muscle cells migrate from the medial layer as the original position to the intima layer and continue to proliferate, thereby forming the neointimal layer, and the involvement of inflammation or thrombus formation results in the occurrence of diseases, such as pulmonary arterial hypertension and vascular stenosis including vascular wall thickening and vessel lumen narrowing.

The current treatment of vascular stenosis is mainly carried out by surgical procedures, such as stent procedures or angioplasty, while these procedures also injure blood vessels and thus have a high probability of recurrence. The stent procedures using the treatment with an anti-platelet agent, an anti-coagulant, an anti-allergic agent, or a drug inhibiting tissue regeneration have been clinically attempted to prevent or treat vascular stenosis, but these procedures do not sufficient treatment effects. Therefore, a fundamental medicine capable of inhibiting the proliferation of smooth muscle cells to treat vascular stenosis and a diagnostic reagent capable of diagnosing the prognosis of diseases and treatment thereof need to be developed.

Of the above-exemplified diseases accompanied by smooth muscle cell proliferation, especially pulmonary arterial hypertension (PAH) has no distinctive symptoms or signs from other diseases, and thus early diagnosis thereof is difficult, while PAH progresses slowly, and thus the time from initial symptoms to definite diagnosis is long, resulting in a high mortality rate. Pulmonary arterial hypertension is a condition in which the blood pressure of the pulmonary artery that supplies blood from the heart to the lungs is increased, resulting in degraded blood circulation, and defined as a state in which the mean pulmonary artery pressure is 25 mmHg or more. The initial symptoms of the disease are not detected, but as the disease progresses, the cardiac output decreases due to overload of the heart in which the blood needs to be released to the lungs through the narrowed pulmonary blood vessels. As a result, dyspnea during exercise, fatigue, general weakness, dizziness, and the like occur, and symptoms, such as hemoptysis, angina, chest pain, and leg edema, may develop, and in severe cases, the symptoms may lead to fainting or heart attack. The pulmonary arterial hypertension is a rare disease that occurs at a rate of 2-10 per million people, but the actual number of patients is expected to be greater considering that the diagnosis thereof is difficult, while the pulmonary arterial hypertension is an intractable disease with a mortality rate of 15% within one year and 50% or more after five years. On the contrary, the treatment strategies remain in symptomatic therapy for alleviating symptoms, while effective medicines and treatment methods are very few.

Therefore, the development of effective diagnostic reagents capable of achieving early diagnosis of diseases caused by excessive proliferation of smooth muscle cells, including pulmonary arterial hypertension, and therapeutic agents therefor is urgent.

The present inventors, while researching proliferation procedures of smooth muscle cells, found that the expression level of FGF12 is closely associated with the proliferation of vascular smooth muscle cells, and especially confirmed that the expression of FGF12 is reduced in the injured blood vessels in which the proliferation of smooth muscle cells actively occurs, and the excessive expression of FGF12 in the injured blood vessels inhibited the proliferation of smooth muscle cells, and therefore, the present inventors completed the present invention.

SUMMARY

The present disclosure provides a method for treating a smooth muscle cell proliferative disease in a subject in need thereof, the method comprising administering to the subject an effective amount of a composition comprising a recombinant expression vector comprising a polynucleotide encoding FGF12.

In another aspect, the present disclosure provides a method for treating a smooth muscle cell proliferative disease in a subject in need thereof, the method comprising administering to the subject an effective amount of a composition comprising FGF12 protein or a fragment thereof.

In still another aspect, the present disclosure provides a method for detecting a marker for a smooth muscle cell proliferative disease, the method, in order to provide information necessary for diagnosis of the smooth muscle cell proliferative disease, comprising:

(a) providing a sample of a subject to be detected;

(b) measuring the expression level of FGF12 in the sample; and (c) comparing the measured expression level of FGF12 with that of a normal subject and determining that the subject is considered to have been afflicted with a smooth muscle cell proliferative disease or to have a probability of being afflicted with a smooth muscle cell proliferative disease in case where the subject has a reduced FGF12 expression level compared with the normal subject.

It is to be understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows immunofluorescent staining results when the injured rat carotid arteries were stained against Ki67 (red), FGF12(green), and α-SMA(red). Cell nuclei were stained with DAPI (blue); NC indicates a negative control group; and scale bar is 50 μm. FIG. 1B shows RT-PCR results illustrating the mRNA levels of FGF12 and smooth muscle cell (SMC) marker genes (SM-MHC, SM22α, and SRF). GAPDH was used as a loading control.

FIG. 2A shows immunofluorescent staining results when arteries of ApoE$^{-/-}$ mice fed with normal diet or high fat diet (HFD) for 12 wk were stained against FGF12 (green) and α-SMA (red). Cell nuclei were stained with DAPI (blue); and scale bar is 50 μm. FIG. 2B shows immunofluorescent staining results when normal human artery (Normal) and arteriosclerotic artery (Patient) were stained against FGF12 (green) and α-SMA (red). NC indicates a negative control group; and scale bar is 100 μm.

FIG. 3A shows the immunofluorescent staining results against FGF12 in the lung tissues five days after saline or monocrotaline (MCT) injection. FIG. 3B shows analysis results of FGF12 mRNA expression in pulmonary arterial hypertension animal models through RT-PCR, indicating that FGF12 expression was remarkably reduced in pulmonary arterial hypertension animal models in a similar manner to the immunofluorescent staining results. FIG. 3C shows through Western blotting analysis that the expression of FGF12 and smooth muscle cell (SMC) marker genes (α-SMA, SM22α) decreased in the pulmonary arterial hypertension animal model, verifying that the expression of FGF12 decreases upon vascular smooth muscle cell dedifferentiation by pulmonary arterial hypertension. Actin is a loading control.

The left panel of FIG. 4A shows RT-PCR results illustrating the expression patterns of FGF12, CDK1, and SM-MHC mRNA in human aortic smooth muscle cells (HASMCs) stimulated with PDGF-BB (50 ng/ml) for 3 hours or 24 hours. The right panel of FIG. 4A shows RT-PCR results illustrating the mRNA expression patterns of FGF12 and SM-MHC mRNA in human pulmonary aortic smooth muscle cells (HPASMCs) stimulated with PDGF-BB (50 ng/ml) for 3 hours or 24 hours. The left panel of FIG. 4B shows immunofluorescent staining images when HASMCs were cultured in basal medium containing or not containing PDGF-BB (50 ng/ml) for one day and stained against FGF12 (green). Cell nuclei were stained with DAPI (blue); and scale bar is 50 μm. The right panel of FIG. 4B shows immunofluorescent staining images when HPASMCs were cultured in basal medium containing or not containing PDGF-BB (50 ng/ml) for one day and stained against FGF12 (green). Cell nuclei were stained with DAPI (blue); and scale bar is 50 μm. FIG. 4C shows luciferase activity measured 48 hours after transfection with a luciferase reporter vector controlled by the FGF12 promoter (pGL3-FGF12) or a control vector (pGL3-basic). * indicates p<0.05 and n=5 FIG. 4D shows RT-PCR results indicating FGF12 and CDK1 mRNA expressed in HASMCs stimulated with PDGF-BB (50 ng/ml) and treated with signaling inhibitors (LY294002, PD98059, U0126, SB203580, BIRB796).

FIG. 5B shows gene ontology (GO) terms of 362 DEGs identified using functional annotation clustering from DAVID. P values are plotted using −log 2. FIG. 5C shows RT-PCR results illustrating the expression patterns of FGF12 and cell cycle-related genes.

FIG. 6A shows FACS results for analyzing the cell cycles of wild type HASMCs (WT), empty vector-transfected HASMCs (pEntry), and FGF12-overexpressed HASMC (pFGF12). FIG. 6B is a bar graph quantitatively showing the cell cycle distribution of the cells derived from FIG. 6A. FIG. 6C shows MTS experimental results illustrating the effect of FGF12 on the FBS (10%)-induced HASMC proliferation. For WT and pEntry, * indicates p<0.05 and n=5. FIG. 6D shows MTS experimental results illustrating the effect of FGF12 on the PDGF-BB (50 ng/ml)-induced HASMC proliferation. For WT and pEntry, * indicates p<0.05 and n=5. FIG. 6E shows MTS experimental results illustrating the effect of FGF12 on the PDGF-BB (50 ng/ml)-induced HPASMC proliferation. For WT and pEntry, * indicates p<0.05 and n=6.

FIG. 8A shows RT-PCR results illustrating the mRNA levels of p53 and p21 expressed in wild type or transfected (pEntry, pFGF12) HASMCs. The mRNA levels in transfected HASMCs were expressed relative to those in WT HASMCs * indicates p<0.05 and n=4. FIG. 8B shows western blot results illustrating the protein levels of FGF12, p53, and phosphorylated p53 (p-p53) expressed in wild type or transfected HASMCs. β-actin is used as a loading control. FIG. 8C shows immunofluorescent staining results when the rat carotid arteries injured due to balloon injury were stained against FGF12 (green) and p-p53 (red). Cell nuclei were stained with DAPI (blue); and scale bar is 50 μm.

FIG. 9A shows RT-PCR results to confirm p53 expression in HASMCs at 24 hours after transfection with p53 siRNA (25 nM or 50 nM) or control siRNA (Cont siRNA) following transfection with adenovirus (Ad-FGF12) for FGF12 overexpression. GAPDH indicates a loading control. FIG. 9B shows cell proliferation patterns analyzed through Ki67 staining after adenovirus-transfected (Ad-LacZ, Ad-FGF12) or non-transfected (WT) HASMCs were transfected with siRNA(Cont siRNA, p53 siRNA). FIG. 9C shows cell proliferation patterns analyzed through Ki67 staining after adenovirus-transfected or non-transfected HASMCs were treated with pifithrin (10 μM) as a p53 inhibitor or PBS. For a control group, * indicates p<0.05, n=4, and NS=not significant. FIG. 9D shows cell proliferation patterns analyzed through Ki67 staining after adenovirus-transfected or non-transfected HASMCs were treated with pifithrin (10 μM) as a p53 inhibitor or PBS. For a control group, * indicates p<0.05, n=6, and NS=not significant.

FIG. 10A shows H&E images of rat common carotid arteries two weeks after balloon injury following transfection with adenovirus (Ad-LacZ or Ad-FGF12). Scale bar is 200 μm. FIG. 10B shows morphometric analysis results of balloon-injured rat common carotid arteries. The quantitative analysis results for neointimal area, intima to media area ratios (I/M), and luminal stenosis (%) were expressed by bar graphs. * indicates p<0.05 and n=5. FIG. 10C shows immunofluorescent staining results illustrating the expression pattern of FGF12 (green) and the cell proliferation pattern through Ki67 (red) staining in balloon-injured rat common carotid arteries following transfection with adenovirus ((Ad-LacZ, Ad-FGF12). The regions indicated by white dot lines on the left panel of FIG. 10C are magnified. The white arrows on the right panel of FIG. 10C indicate proliferating cells in which Ki67 is expressed at a high level. Scale bar is 200 μm.

FIG. 11A shows immunofluorescent staining results against FGF12 (green) and Ki67 (red) in HUVECs or hASMCs transfected with Ad-FGF12 or non-treated with viruses. Cell nuclei were stained with DAPI (blue). On the HUVEC Ad-FGF12 image, white * marks indicate cells expressing FGF12 and Ki67 simultaneously in Ad-FGF12-transfected HUVECs. On the hASMC Ad-FGF12 image, white arrow marks indicate cells expressing Ki67 while not expressing FGF12 in Ad-FGF12-transfected hASMCs. FIG. 11B shows a bar graph quantifying the Ki67 staining results of FIG. 11A as a percentage (%) of Ki67 stained cells.

FIG. 12A shows a real time RT-PCR result showing the tendency of FGF12, α-SMA, SM22α and ID3 mRNA expression in HPASMC stimulated with BMP-2, BMP-4 and BMP-7 (10 and 30 ng/ml) for 48 hours, respectively. FIG. 12B shows a Western blotting result showing the tendency of FGF12, α-SMA, SM22α and SM-MHC protein expression in HPASMC stimulated with BMP-2, BMP-4 and BMP-7 (30 ng/ml) for 48 hours, respectively, while actin is a loading control. FIG. 12C shows a RT-PCR result showing the mRNA expression pattern of BMPR2 and FGF12 after HPASMC [Cont siRNA (si-Cont), BMPR2 siRNA (si-BMPR2)] transformed with PBS or siRNA was cultured for 1 day in basal medium with or without BMP-4 (30 ng/ml), while GAPDH is a loading control.

FIG. 13A is RT-PCR results showing the mRNA expression profiles of FGF12 and smooth muscle cell (SMC) marker genes (α-SMA, SM22α) after PBS- or siRNA-transformed HPASMC [Cont siRNA (si-Cont), FGF12 siRNA (si-FGF12)] was respectively cultured for 1 day in a basal medium with or without BMP-4 (30 ng/ml). GAPDH is a loading control.

FIG. 13B is immunofluorescence staining results showing the stained proteins of smooth muscle cell (SMC) marker genes (α-SMA, SM-MHC) after PBS- or siRNA-transformed HPASMC (si-Cont, si-FGF12) was respectively cultured for 1 day in a basal medium with or without BMP-2 (30 ng/ml). The nucleus was stained with DAPI (blue). Quantitative analysis of immunostained cells expressing each smooth muscle cell marker protein is indicated by the bar graph at the bottom. It can be seen that HPASMC (Control: CTR) without BMP-2 treatment is not stained with smooth muscle cell markers. *p<0.05, and n=5.

FIG. 13C is immunofluorescence staining results showing the stained proteins of smooth muscle cell (SMC) marker genes (α-SMA, SM-MHC) after PBS- or siRNA-transformed HPASMC (si-Cont, si-FGF12) was respectively cultured for 1 day in a basal medium with or without BMP-4 (30 ng/ml). The nucleus was stained with DAPI (blue). Quantitative analysis of immunostained cells expressing each smooth muscle cell marker protein is indicated by the bar graph at the bottom. It can be seen that HPASMC (Control: CTR) without BMP-4 treatment is not stained with smooth muscle cell markers. *p<0.05.

FIG. 13D is immunofluorescence staining results showing the stained proteins of smooth muscle cell (SMC) marker genes (α-SMA, SM-MHC) after PBS- or siRNA-transformed HPASMC (si-Cont, si-FGF12) was respectively cultured for 1 day in a basal medium with or without BMP-7 (30 ng/ml). The nucleus was stained with DAPI (blue). Quantitative analysis of immunostained cells expressing each smooth muscle cell marker protein is indicated by the bar graph at the bottom. It can be seen that HPASMC (Control: CTR) without BMP-7 treatment is not stained with smooth muscle cell markers. *p<0.05.

The nuclei were stained with DAPI (blue), and the quantitative analysis of Ki67 stained cells (white arrowheads) in each HPASMC was indicated by the bar graph at the bottom. $*p<0.05$.

Figure 15A:
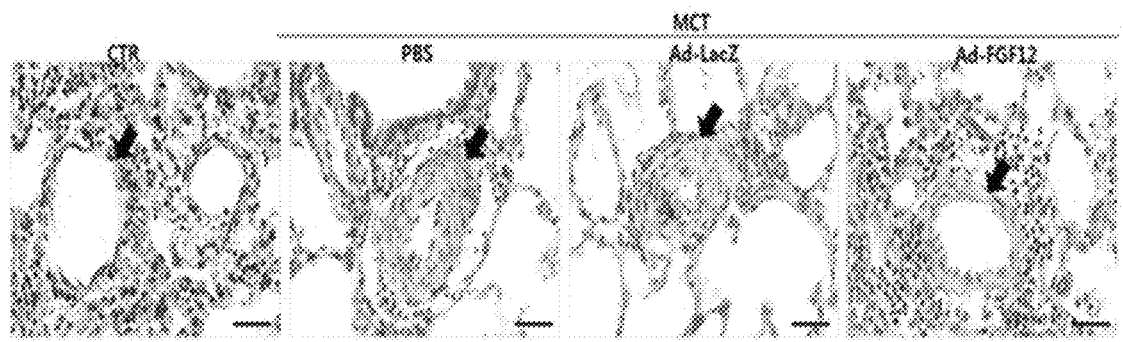
Figure 15B:
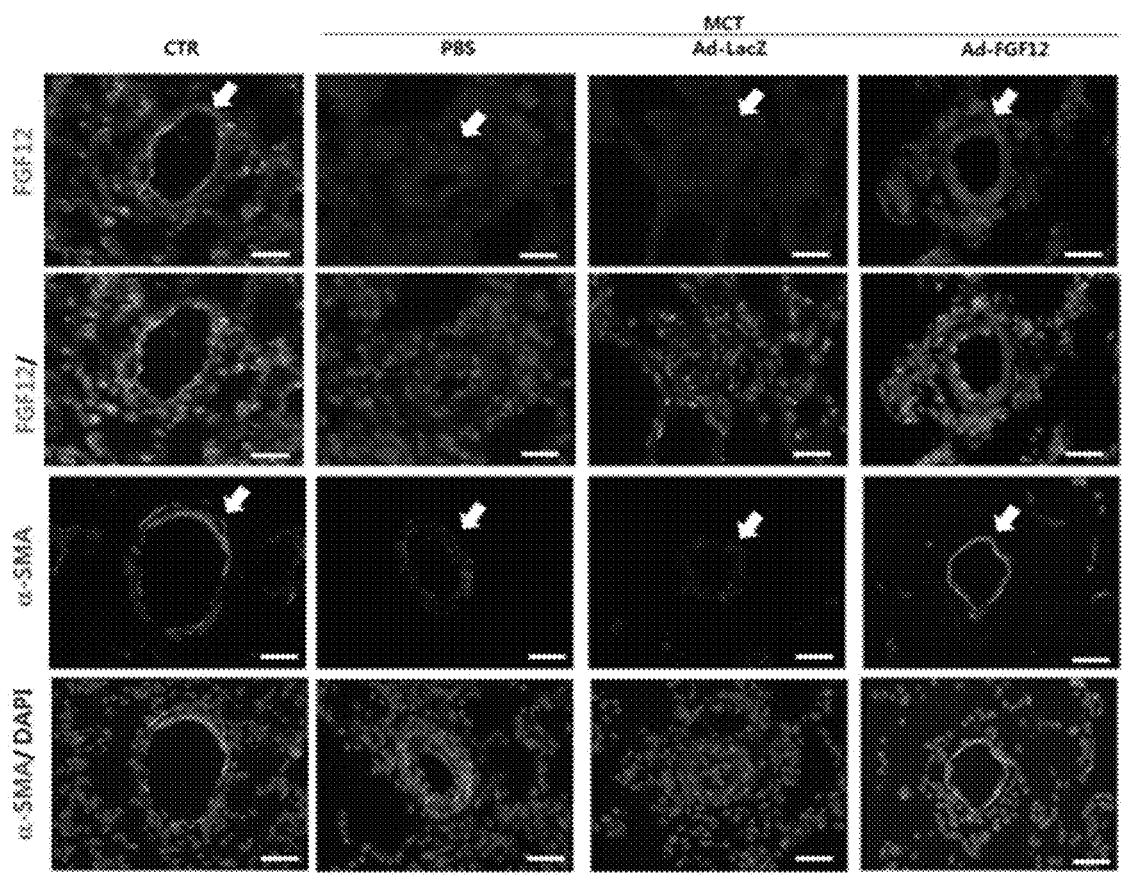
Figure 15C:
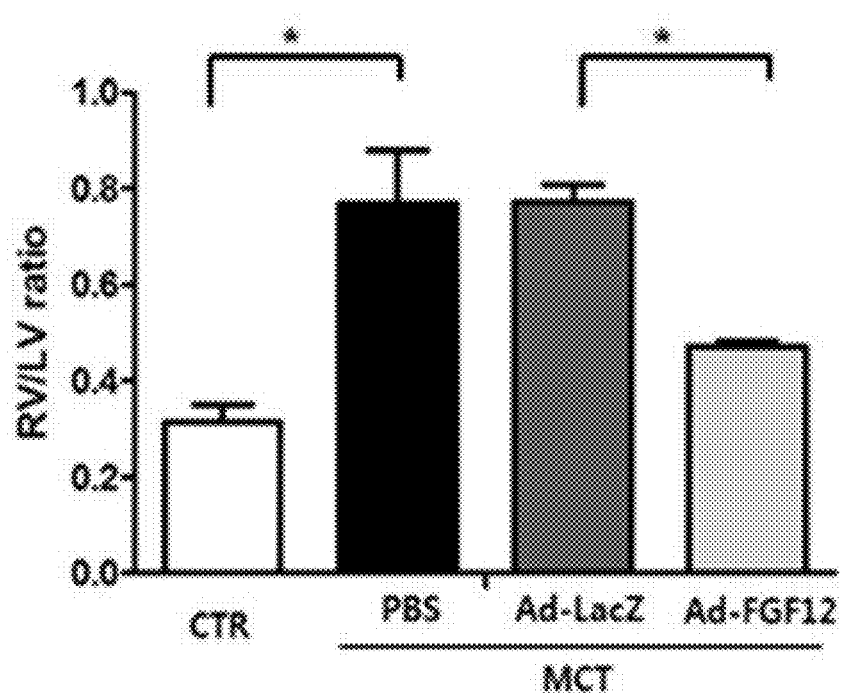

FIG. 15A, FIG. 15B and FIG. 15C are experimental results showing that the overexpression of FGF12 may treat pulmonary arterial hypertension (PAH).

FIG. 15A is a photograph of H&E staining of rat lung tissues after 3 weeks of intratracheal injection of PBS or adenovirus (Ad-LacZ, Ad-FGF12) preceded by 2 weeks after injection of monoclotharin (MCT) into rat (black arrow indicating the pulmonary artery). FIG. 15B shows the protein expression patterns of FGF12 (green) and smooth muscle cell marker gene ($\alpha$-SMA) in pulmonary artery treated with PBS or infected with adenovirus (Ad-LacZ, Ad-FGF12) through immunofluorescence staining. The nuclei were stained with DAPI (blue). FIG. 15C is a graphical representation of the weight ratio of right ventricular tissue to left ventricular tissue of rat infected with adenovirus (Ad-LacZ, Ad-FGF12). $*p<0.05$.

DETAILED DESCRIPTION OF THE ILLUSTRATED EMBODIMENTS

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art.

The present invention provides a composition for treating a smooth muscle cell proliferative disease, the composition comprising, as an active ingredient, a recombinant expression vector including a polynucleotide encoding FGF12.

The present inventors first established through a series of experiments that FGF12 plays a crucial role in inhibiting cell proliferation in smooth muscle cells through the p53 signaling system. The present inventors especially confirmed that even under conditions (stimulation by PDGF-BB or FBS, etc.) in which smooth muscle cell proliferation is promoted, the over-expression of FGF12 can inhibit the smooth muscle cell proliferation due to the above factors.

The composition of the present invention can be used for gene therapy for treating a smooth muscle cell proliferative disease by using the functions of FGF12 established by the present inventors. The term "gene therapy" refers to treating a disease by delivering a gene having a therapeutic effect to cells or tissues to be treated (or target cells or tissues) and allowing the gene to be expressed. The gene therapy can be topically applied to cells or tissues with a pathological phenomenon, and can be expected to have a therapeutic effect by gene expression for a relatively long period. The composition of the present invention comprises, as an active ingredient, a recombinant expression vector comprising a polynucleotide encoding FGF12, and inhibits the smooth muscle cell proliferation by delivering the FGF12 gene into proliferating smooth muscle cells and allowing the FGF12 gene to be excessively expressed therein.

As used herein, the term "treatment" or "treating" refers to inhibiting occurrence or recurrence of disease, alleviating symptoms, reducing direct or indirect pathological consequences of disease, reducing the rate of disease progression, improving, bettering, or relieving disease conditions, or improving prognosis. As used herein, the term "prevention" or "preventing" refers to all actions that suppress the onset of disease or delays the progress of disease.

The term "smooth muscle cell (SMC)" refers to muscle cells of the smooth muscle. The term "smooth muscle" refers to a muscle without horizontal patterns, and is also called a non-striated muscle. In vertebrates, the muscles constituting muscle walls of internal organs other than the heart, that is, the internal muscle walls for the gastrointestinal tract, the airway of respiratory organs, the blood vessels, the bladder, and the uterus are all smooth muscles. The smooth muscles move involuntarily, while the contraction of the smooth muscles is directly controlled by the autonomic nervous system and affected by hormones.

The smooth muscle cells of the present invention may be preferably vascular smooth muscle cells (VSMCs). The term "vascular smooth muscle cell" refers to cells constituting the smooth muscle of the blood vessels. The vascular smooth muscle cells form and support the structure of the vascular system, and regulate the blood pressure and blood flow by their contraction and relaxation through the regulation by the nervous system and hormones. The vascular smooth muscle cells highly express smooth muscle-specific genes (contractile genes), such as SMA, SM22$\alpha$, SM-MHC, SM-calponin, and the like, and hardly proliferate in the healthy and normal condition. Meanwhile, the vascular smooth muscle cells actively proliferate and migrate, as a part of a remodeling procedure for restoring vascular injury in a situation of vascular wounds, atherosclerosis, inflammation, or other vascular diseases, and induce changes, such as increasing matrix synthesis and secretion.

The term "smooth muscle cell proliferative disease" according to the present invention refers to a disease which occurs due to excessive proliferation of smooth muscle cells. Herein, the smooth muscle cell proliferative disease may be preferably a vascular smooth muscle cell proliferative disease. The vascular smooth muscle cell proliferative disease includes diseases occurring directly by the proliferation of vascular smooth muscle cells, for example, vascular stenosis, vascular restenosis, pulmonary arterial hypertension, arteriosclerosis, and atherosclerosis, as well as cardiovascular diseases caused secondarily or having severe symptoms by the above diseases, for example, cardiac heart failure, myocardial infarction, angina, arrhythmia, congenital heart disease, stroke, and peripheral vascular stenosis.

Herein, the vascular smooth muscle cell proliferative disease may be preferably vascular stenosis, vascular restenosis, pulmonary arterial hypertension, arteriosclerosis, or atherosclerosis.

The term "vascular stenosis" refers to a disease in which the inside of the blood vessel is abnormally narrowed and the blood flow is reduced due to inflammation, thrombosis, and excessive proliferation of smooth muscle cells, after the injury of the vascular walls. The term "vascular restenosis" refers to the re-occurrence of vascular stenosis. In most cases, the vascular restenosis occurs after vascular procedures, such as dilating the vascular lumen or decongesting the blocked blood vessels to remove vascular stenosis. Vascular procedures, for example, stent, angioplasty such as balloon angioplasty, and vascular bypass or vascular graft such as coronary artery bypass surgery, per se may injure blood vessels or cause inflammation, resulting in vascular stenosis. Arteriosclerosis is a disease in which fat is deposited or fiberized in the inner layer of the artery, and it is known that vascular restenosis occurring after stent insertion for progression of arteriosclerosis and vasodilation is due to the proliferation, migration, and extracellular matrix secretion of vascular smooth muscle cells.

When the media layer having endothelial cells or smooth muscle cells of the intima layer is injured due to the above procedures, inflammation, blood vessel wounds or the like, the smooth muscle cells migrate to the intima layer and develop a state characterized by the proliferation of cells and the secretion of a substrate, such as collagen, thereby forming the neointimal layer and causing neointimal hyperplasia continuing proliferation. Subsequently, the vascular wall is thickened and the vascular lumen is narrowed.

The term "pulmonary arterial hypertension (PAH)" refers to a disease in which the blood pressure of the pulmonary artery that supplies blood from the heart to the lung is increased and the blood circulation in the lungs is inhibited. Pulmonary arterial hypertension is diagnosed when the pressure of the pulmonary artery is 25 mmHg or more in a stable state and/or is 30 mmHg or more in an exercise state, and confirmed through echocardiography, electrocardiogram, cardiac catheterization, walking test or the like.

Pulmonary arterial hypertension diseases are divided into an idiopathic pulmonary arterial hypertension caused by no specific and a secondary pulmonary arterial hypertension caused by a primary disease. The main cause of pulmonary arterial hypertension is the abnormal proliferation of smooth muscle cells constituting the pulmonary artery blood vessels, and resultantly, the pulmonary arterial hypertension is accompanied by vascular remodeling, such as thickened vascular walls, vascular occlusion in which the pulmonary vascular lumen is narrowed, vasocontraction, while the functions of vascular endothelial cells are further degraded. If the disease progresses, blood clots may develop inside the blood vessels, and the blood may be released through the narrowed pulmonary artery, resulting in an overload of the heart with symptoms of breathing difficulty, chronic fatigue, and chest pain, and in severe cases, fainting or heart attack. The heritable PAH, which accounts for approximately 15-20% of pulmonary arterial hypertension, is known to be associated with autosomal dominant mutations of TGF-beta superfamily genes, such as BMPR2 and ALK1, while the mutations of these genes have been also found in many of the non-heritable PAH.

As medicines for pulmonary arterial hypertension, endostein receptor antagonists, such as Bosentan and Ambrisentan, phosphodiesterase (PDE)-5 inhibitors, such as Sildenafil and Tadalafil, and prostacyclin receptor agonists, such as Iloprost, Treprostinil, and Epoprostenol, which act on vascular endothelial cells to promote the expansion of blood vessels or to inhibit the contraction thereof, have been currently developed. However, 80% or more of patients with pulmonary arterial hypertension were reported not to respond to vasodilator therapy (Archer S L et al., *Circulation* (2010), 121:2045-2066). In these unresponsive patients, the lowering of the blood pressure through vascular expansion rather reduces the cardiac output, and thus there is a risk of worsening of symptoms. The effective diagnostic reagents and medicines for early diagnosis of pulmonary arterial hypertension are very few.

The term "FGF12" refers to fibroblast growth factor 12, and is also called FGF12, FGF12B, FHF1, or the like. Human FGF12 is known to have two isoforms, and the mRNA sequences or amino acid sequences thereof are NM_021032.4 (FGF12 isoform 1, mRNA), NP_066360.1 (FGF12 isoform 1, protein), NM_004113.5 (FGF12 isoform 2, mRNA), NP_004104.3 (FGF12 isoform 2, protein), and the like, which are known by Genbank accession numbers. FGF12 is similar to other fibroblast growth factors (FGFs) with respect to sequences and structures, while FGF12 is not secreted outside cells due to the absence of N-terminal secretion signal sequences, but is present mainly in the nucleus or cytoplasm, and has biochemically distinguishable features, such as not activating the FGF receptor on the cell surface. Therefore, FGF12 is often classified as an FGF homologous factor (FHF). The biological functions of FHF to which FGF12 belongs have been currently unknown. It has been reported that FHF is expressed at a high level in the developing or mature nervous system of humans, mice, chickens and the like, and that the impairment of FHF functions causes abnormalities in the nervous system and behavior (Pablo J L et al., *Neuroscientist* pii: 1073858414562217), but the research on FHF functions or related signaling systems is very insufficient in the areas other than the nervous system.

Herein, it is first disclosed by the present inventors that FGF12 plays an important role in inhibiting the proliferation of smooth muscle cells. The smooth muscle cell proliferation inhibitory effect by FGF12 is completely opposite to the promotion of division and proliferation of various cells by the other known FGFs. It has been found that FGFs of the FGF family, other than FHF, such as FGF1, and FGF2 also called basic FGF (bFGF), promote the proliferation of vascular smooth muscle cells through various signaling systems (Nabel E G et al., *Nature* 362:844-6, Reidy M A et al., *Circulation* 86:11143-6).

The specific functions of FGF12 established by the present inventors are as follows.

In an Example of the present invention, it has been found that the expression of FGF12 was reduced by factors for promoting smooth muscle cell proliferation. When the smooth muscle cells were stimulated with the platelet-derived growth factor subunit B homodimer (PDGF-BB; 50 ng/ml) BB or serum (FBS; 10%), the division of smooth muscle cells was increased and the expression of FGF12 was significantly reduced. As a result of the signaling system inhibitory test, the reduction of FGF12 expression by PDGF-BB was shown to be mediated by the PI3 kinase signaling system.

In another Example of the present invention, it has been confirmed that FGF12 inhibited the division of smooth muscle cells. Such an effect of FGF12 in inhibiting smooth muscle cell cannot be expected at all, considering the fact that other members of the FGF family, for example, FGF1 or FGF2, promote cell proliferation in various cells.

Specifically, FGF12 inhibited the expression of the CDK1, CDK2, CCNA2, CDC6, CDC20 genes and the like associated with cell cycle progression. In addition, in the smooth muscle cells which are transfected with a pCMV6 recombinant expression vector containing the operatively linked FGF12 to overexpress FGF12, the cell cycle was not progressed, and the proportion of cells in the G1 stage was significantly higher than that in the control group. It was confirmed that when FGF12 was overexpressed in the smooth muscle cells stimulated with the smooth muscle cell proliferation promoting factor PDGF-BB or FBS, the smooth muscle cell proliferation induced by the proliferation promoting factor was inhibited. The effect of FGF12 in inhibiting the smooth muscle cell proliferation could also be confirmed through the FGF12 activity inhibitory test using FGF12 siRNA.

In addition, the present inventors established, in another example, that the effect of FGF12 on smooth muscle cells was mediated by the p53 signaling system. As a result of analyzing the differentially expressed genes (DEGs) in FGF12-overexpressing smooth muscle cells, it was observed that there were several genes, of which transcription is regulated by p53, and that phosphorylated p53 was expressed in a very similar pattern to FGF12 also in the FGF12-overexpressing injured arterial tissues. In addition, when the p53 functions were inhibited by siRNA or an inhibitor compound (pifithrin; 10 μM) in the smooth muscle cells transfected with FGF12-overexpressing adenovirus (Ad-FGF12), the smooth muscle cell inhibitory effect of FGF12 was cancelled out.

In another example of the present invention, it was confirmed in vivo that the overexpression of FGF12 had a treatment effect to inhibit the proliferation of vascular smooth muscle cells. A balloon embolectomy catheter was used to cause vascular injury in the rat common carotid artery, and the rats were transfected with adenovirus to allow the overexpression of FGF12. As a result, the indicators of vascular stenosis, such as the neointimal area, the intimal to medial area ratio (I/M), and the luminal stenosis (%), were observed to be greatly reduced.

The present inventors also showed that the cell division and proliferation inhibitory effects by FGF12 were specific to smooth muscle cells, while FGF12 did not affect endothelial cells. When human vascular smooth muscle cells or vascular endothelial cells (HUVECs) were transfected with Ad-FGF12 to overexpress FGF12, vascular smooth muscle cells expressing the cell proliferation marker Ki67 were remarkably reduced, but the number of HUVECs expressing Ki67 was not changed.

In another Example of the present invention, it was confirmed that the expression of FGF12 is decreased in pulmonary arterial hypertension.

In still another Example of the present invention, it was verified that FGF12 inhibits the proliferation of smooth muscle cells, while promoting the differentiation thereof. The present inventor's finding that FGF12 inhibits the proliferation of smooth muscle cells is an unexpected result, in contrast to other members of the FGF family, such as FGF1 or FGF2, which are known to promote cell proliferation in various cells.

Specifically, it was observed that the expression of FGF12 significantly decreased by PDGF-BB which promotes the proliferation of vascular smooth muscle cells. It was found that as a result of transfection of pulmonary arterial smooth muscle cells to induce FGF12 overexpression, the proliferation of pulmonary arterial smooth muscle cells by PDGF-BB was remarkable reduced. In particular, bone morphogenetic protein (BMP), which is a potent differentiation promoter and proliferation inhibitor of vascular smooth muscle cells, was shown to increase the expression of FGF12 in pulmonary arterial smooth muscle cells through signal transduction via BMP receptor 2. That is, these results confirm that the effect of BMP in promoting the differentiation of and inhibiting the proliferation of vascular smooth muscle cells is mediated through FGF12.

Accordingly, in further another Example of the present invention, it was confirmed through in vivo experiments that the overexpression of FGF12 inhibited the proliferation of and promoted the differentiation of pulmonary arterial smooth muscle cells in which pulmonary arterial hypertension was progressing, thereby treating pulmonary arterial hypertension. As a result of the overexpression of FGF12 in the lungs by using adenovirus after inducing pulmonary arterial hypertension in rats with monocrotaline, it was observed that the thickness of the vascular endothelial and mesenchymal walls composed of vascular smooth muscle cells in the pulmonary artery was markedly decreased, resulting in the widened internal diameter of the blood vessel. It was also found that vascular smooth muscle cells expressed the differentiation markers at a high rate. In addition, the weight ratio of right ventricle to left ventricle in the animals with the overexpressed FGF12 were found to be significantly lower in comparison with PBS or control adenovirus-infected animals, indicating that pulmonary arterial hypertension may be treated through the overexpression of FGF12.

It can be expected that, on the basis of the cell proliferation inhibitory effect, differentiation stimulatory effect, and the action mechanism of FGF12 established by the present inventors, the recombinant expression vector containing a polynucleotide encoding FGF12 is used to induce the overexpression of FGF12 in smooth muscle cells, and can be used to prevent or treat the promotion of smooth muscle cells. Particularly, the cell proliferation inhibitory effect of FGF12 is specific to smooth muscle cells, while not affecting endothelial cells located closely to smooth muscle cells in the blood vessels. Therefore, it can be expected that the use of the present invention can minimize the side effect in neighboring cells, and thus therapeutic agents for a smooth muscle cell proliferative disease may be developed, which is distinguishable from other existing smooth muscle cell proliferation inhibitors that also inhibits the proliferation activity of vascular endothelial cells.

The composition for treating a smooth muscle cell proliferative disease in accordance with the present invention comprises, as an active ingredient, a recombinant expression vector containing a polynucleotide encoding FGF12.

As used herein, the term "polynucleotide" or "nucleic acid" refers to single- or double-stranded deoxyribonucleotide (DNA) or ribonucleotide (RNA) Unless otherwise limited, the term includes known analogs of natural nucleotides that hybridize to nucleic acids in a manner similar to naturally-occurring nucleotides.

The polynucleotide encoding the FGF12 in accordance with the present invention may be derived from a mammal, preferably from a human being. The polynucleotide encoding FGF12 may include a sequence of human FGF12 mRNA, and most preferably, may include a nucleotide sequence represented by SEQ ID NO: 1 or SEQ ID NO: 3.

In addition, the polynucleotide encoding FGF12 also includes a sequence that shows substantial identity with the sequence of human FGF12 mRNA, and preferably, the nucleotide sequence represented by SEQ ID NO: 1 or SEQ ID NO: 3. The term "substantial identity" refers to a sequence that shows at least 70% homology when the sequence is aligned with any other sequence, which is a comparative object to the human FGF12 mRNA sequence, as much as possible, and comparing and analyzing the sequences using an algorithm and an analysis method commonly used in the art. The protein encoded by the nucleotide sequence, which is substantially the same as the FGF12 mRNA nucleotide sequence, may be FGF12 protein, preferably a protein comprising an amino acid sequence represented by SEQ ID NO: 2 or SEQ ID NO: 4, or a functional equivalent to FGF12 protein. The term "functional equivalent" refers to a polypeptide having at least 70%, preferably at least 80%, and more preferably at least 90% sequence homology (i.e., identity) to the amino acid sequence of FGF12 of the invention, the polypeptide showing substantially homologous physiological activity with FGF12. The term "substantially homologous physiological activity" refers to the activity to induce and maintain the normal trait of smooth muscle cells on the basis of the mechanism in which FGF12 is expressed in the smooth muscle cells to inhibit the proliferation and mitigation of the smooth muscle cells.

The term "expression" refers to the production of a protein or nucleic acid in cells, and the term "recombinant expression vector" refers to a vector capable of expressing a target protein or a target nucleic acid (RNA) in suitable host cells, and indicates a gene construct containing an essential regulatory element operatively linked so as to express a polynucleotide (gene) insert. The term "operatively linked" refers to the functional linkage of a nucleic acid expression control sequence and a nucleic acid sequence encoding a target protein or RNA so as to perform general functions, and means the linkage therebetween so as to express a gene by an expression control sequence. The term "expression control sequence" refers to a DNA sequence that controls the expression of an operatively linked polynucleotide sequence in particular host cells. Such an expression control sequence includes a promoter for transcription, any operator sequence for controlling transcription, a sequence for encoding a proper mRNA ribosomal binding site, a sequence for controlling the termination of transcription and translation, an initiation codon, a termination codon, a polyadenylation A signal, an enhancer and the like. The recombinant expression vector of the present invention is used in a vector conventionally used in the field of cloning, particularly in the field of gene therapy, while the type thereof is not particularly limited as long as it can be selected by a person skilled in the art. Examples thereof include a plasmid vector, a cosmid vector, a bacteriophage vector, a virus vector and the like. The recombinant vector can be prepared using gene recombinant techniques well known in the art, while site-specific DNA cleavage and linkage are carried out using enzymes generally known in the art.

Therefore, the recombinant expression vector according to the present invention is a gene construct containing both a polynucleotide encoding FGF12 and an essential expression control sequence necessary for expressing FGF12 in smooth muscle cells, wherein these are operatively functionally linked. The recombinant expression vector of the present invention may contain a selection marker and/or a replication origin for selecting a host cell in the production of the recombinant expression vector. In addition, the expression vector may optionally contain an expression control sequence, a signal sequence for membrane targeting or secretion, a leader sequence, and the like, while the expression vector may be prepared variously according to purposes, including a sequence of a reporter or marker gene for showing and confirming smooth muscle cell-specific shrinkage.

The recombinant expression vector according to the present invention may be a recombinant virus vector.

As for the recombinant virus vector of the present invention, any vector that can be ordinarily used to deliver a gene in the field of gene therapy may be used without limitation. The recombinant virus vector may be selected from the group consisting of adenovirus vector, adeno-associated virus (AAV) vector, retrovirus vector, herpes virus vector, lentivirus vector, vaccinia virus vector, and poxvirus vector.

The recombinant virus vector in the present invention may preferably be an adenovirus vector. Adenovirus is used as a carrier for delivering a therapeutic gene in the field of gene therapy due to its medium size of genome among viruses, the convenience of gene manipulation and manufacturing, the ease of production and isolation with a high titer, and the broad range of target cells, high transfection efficiency and the like. Adenoviruses lacking the auto-replication and production capacity of viruses are widely used for gene therapy.

The composition for treating a smooth muscle cell proliferative disease, the composition comprising, as an active ingredient, the recombinant expression vector containing a polynucleotide encoding FGF12 of the present invention, can be applied in vivo through various delivery methods known in the field of gene therapy. Examples of the delivery method include naked DNA injection, electroporation, gene gun, sonoporation using ultrasound, magnetofection using electromagnetic field, gene delivery using a construct, such as liposome or nanoparticle, gene delivery using virus, and the like. The composition of the present invention may be delivered to smooth muscle cell using preferably virus, and most preferably adenovirus.

A suitable dose of the composition of the present invention may be properly adjusted considering various factors, such as the method of formulation, the manner of administration, patient's age, body weight, and sex, the severity of disease, the food, the time of administration, the route of administration, the period of treatment, the excretion rate, and the response sensitivity. A person skilled in the art can determine and prescribe a dose effective for treatment considering the above factors. When the composition of the present invention is used for gene therapy for a smooth muscle cell proliferative disease, the composition of the present invention contains, for example, adenovirus containing a polynucleotide encoding FGF12 at a concentration of $1 \times 10^5$ to $1 \times 10^{15}$ pfu/ml, and may be administered once to several times. In the present invention, the rat models with vascular injury caused by balloon injury were injected with adenovirus containing a polynucleotide encoding FGF12 through an injured vascular site at a concentration of $1 \times 10^7$ pfu/ml once, and then after two weeks, the treatment effect by FGF12 expression was examined.

The composition according to the present invention may be administered orally or parenterally, but preferably parenterally. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration, and may be preferably intravascular administration.

The composition of the present invention may be variously formulated, together with a pharmaceutically acceptable carrier, according to the route of administration, by a method known in the art. The term "pharmaceutically acceptable" composition refers to a non-toxic composition that is physiologically acceptable, does not inhibit action of an active ingredient when administered to humans, and does not normally cause an allergic reaction or similar reactions, such as gastroenteric troubles and dizziness. The carrier includes all kinds of solvents, dispersion media, oil-in-water or water-in-oil emulsions, aqueous compositions, liposomes, microbeads, and microsomes.

As for the parenteral administration, the pharmaceutical composition of the present invention may be formulated in a dosage form of an injection, a transdermal administration preparation, and a nasal inhalant, together with a suitable parenteral carrier, by a method known in the art. The injection needs to be essentially sterilized and to be protected from the contamination of microorganisms, such as bacteria and fungus. Examples of the suitable carrier for an injection may include, but are not limited to, water, ethanol, polyols (e.g., glycerol, propylene glycol, liquid polyethylene glycol, etc.), mixtures thereof, and/or solvents or dispersive media containing vegetable oils. More preferably, Hanks' solution, Ringer's solution, phosphate buffered saline (PBS) or sterile water containing triethanolamine for injection, or an isotonic solution (such as 10% ethanol, 40% propylene glycol, or 5% dextrose) may be used as a suitable carrier. In order to protect the injection from microbial contamination, the injection may further containing various antibacterial and antifungal agents, such as parabens, chlorobutanol, phenol, sorbic acid, and thimerosal. In most cases, the injection may further contain an isotonic agent, such as sugar or sodium chloride.

The form of the transdermal administration preparation includes ointment, cream, lotion, gel, solution for external application, plaster, liniment, and aerosol. The "transdermal administration" refers to locally administering the composition of the present invention into the skin to deliver an effective amount of active ingredient contained in the composition into the skin. For example, the composition of the present invention may be administered by a method of being made into an injection dosage form and slightly pricking the skin with a 30-gauge needle or being directly applied to the skin. These preparations are described in the document, which is a formulary generally known in pharmaceutical chemistry (Remington's Pharmaceutical Science, 15th Edition, 1975, Mack Publishing Company, Easton, Pa.).

In the case of an inhalation agent, the compound used according to the invention may be conveniently delivered in the form of aerosol spray from a pressurized pack or a nebulizer, using a suitable propellant, for example, dichlorofluoromethane, trichlorofluoromethane, dichlorotetrafluoroethane, carbon dioxide, or other suitable gases. In the case of a pressurized aerosol, the unit of administration may be determined by providing a valve that delivers a measured quantity. For example, a gelatin capsule and a cartridge used in an inhaler or an insufflator may be formulated to contain a compound, and a powder mixture of proper powder materials, such as lactose or starch.

Other pharmaceutically acceptable carriers are referenced in the following literature (Remington's Pharmaceutical Sciences, 19th ed., Mack Publishing Company, Easton, Pa., 1995).

The composition according to the present invention may further contain at least one buffer (for example, saline solution, or PBS), a carbohydrate (for example, glucose, mannose, sucrose, or dextran), a stabilizer (for example, sodium bisulfate, sodium sulfite, or ascorbic acid), an antioxidant, a bacteriostat, a chelating agent (for example, EDTA or glutathione), an adjuvant (for example, aluminum hydroxide), a suspension agent, a thickener, and/or a preservative).

In addition, the composition of the present invention may be variously formulated by a method known in the art so as to provide rapid, continuous, or delayed release of an active ingredient after the composition is administered to a mammal.

In addition, the composition of the present invention may be administered in combination with a known compound having an effect of treating a smooth muscle cell proliferative disease. In addition, the composition of the present invention may be administered together with a usual vascular procedure.

In addition, the present invention provides a composition for treating a smooth muscle cell proliferative disease, the composition comprising, as an active ingredient, FGF12 protein or a fragment thereof.

As used herein, the term "protein" is used interchangeably with the term "polypeptide" or "peptide", and refers to, for example, a polymer of amino acid residues, as typically found in proteins in nature. The term "fragment" of the FGF12 protein refers to a peptide of a portion of the FGF12 protein.

Herein, the FGF12 protein may be derived from a mammal, preferably from a human being. The FGF12 protein of the present invention may comprise, most preferably an amino acid sequence of human FGF12 protein, that is, an amino acid sequence represented by SEQ ID NO: 2 or SEQ ID NO: 4.

The FGF12 protein contained in the composition of the present invention refers to a protein having substantially equivalent physiological activity as the FGF12 protein. The protein having the substantially equivalent physiological activity includes a functional equivalent and a functional derivative of FGF12 protein. As used herein, the "functional equivalent" refers to a polypeptide exhibiting the same physical activity as in FGF12 protein, and includes a fragment of FGF12 protein. The substantially equivalent physiological activity refers to an activity to inhibit the division and proliferation of smooth muscle cells when delivered into the smooth muscle cells. The term "functional equivalent" refers to a polypeptide having sequence homology of at least 70%, preferably at least 80%, and more preferably at least 90% to the amino acid sequence represented by SEQ ID NO: 2 or SEQ ID NO: 4. The functional equivalent may include a polymorphism protein of FGF12, such as small nucleotide polymorphism (SNP), having the substantially equivalent physiological activity as in, for example, FGF12 protein.

The functional equivalent may result from the addition, substitution, or deletion of a portion of the amino acid sequence of FGF12 protein. Herein, the substitution of amino acid is preferably a conservative substitution. Examples of naturally occurring conservative substitution of amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). In addition, the functional equivalent includes variants in which some amino acids are deleted from the amino acid sequence of the FGF12 protein of the present invention. The deletion or substitution of amino acids is preferably located at a region that is not directly associated with the physiological activity of the protein of the present invention. The deletion of amino acids is preferably located at a region that is not directly involved in the physiological activity of the FGF12 protein of the present invention. The functional equivalent also includes variants in which some amino acids are added to both terminals of the amino acid sequence or into the amino acid sequence of the FGF12 protein.

Moreover, the functional equivalent of the present invention also includes a polypeptide derivative that has some modification in the chemical structure of the FGF12 protein according to the present invention, while the fundamental backbone of the FGF12 protein and physiological activity thereof are maintained. For example, the modification includes a structural modification for changing the stability, storability, volatility, or solubility of the FGF12 protein of the present invention. In addition, the FGF12 protein of the present invention may further include a chemical functional group or a cell-penetrating peptide (CPP) for effective delivery into smooth muscle cells while maintaining the basic skeleton and physiological activity. The cell-penetrating peptide per se can pass through the phospholipid bilayer structure of the cell membrane or has an amino acid sequence capable of promoting endocytosis, and examples thereof include, but are not limited to, HIV virus-TATderived peptide, a peptide derived from VP22, transportan, or penetratin, cell membrane-penetrating signal sequence, a peptide containing a large amount of positively charged amino acids, such as arginine/lysine, an amphipathic peptide carrier, and the like.

The FGF12 protein of the present invention can be constructed by a genetic engineering method. First, a DNA sequence encoding the FGF12 protein is constructed by a conventional method. The DNA sequence can be constructed by PCR amplification using appropriate primers. The constructed DNA sequence is inserted into a vector, which contains one or more expression control sequences (e.g., promoters, enhancers, etc.) that are operatively linked to the DNA sequence and control the expression of the DNA sequence, and the recombinant expression vector constructed therefrom is used to transform host cells. The prepared transformant is incubated in media under the condition suitable to express the DNA sequence, and a substantially pure polypeptide encoded by the DNA sequence is collected from the cultured product. The collection may be performed using a method known in the art (e.g., chromatography). Herein, the term "substantially pure polypeptide" means that the polypeptide according to the present invention does not substantially contain any other protein derived from host cells. Genetic engineering methods for the polypeptide synthesis of the present invention can be referenced in the following literature: Maniatis et al., Molecular Cloning; A laboratory Manual, Cold Spring Harbor laboratory, 1982; Sambrook et al., supra; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

In addition, the FGF12 protein of the present invention may be chemically synthesized according to a technique known in the art (Creighton, Proteins: Structures and Molecular Principles, W.H. Freeman and Co., NY (1983)). That is, the FGF12 protein of the present invention may be prepared by using stepwise liquid- or solid-phase synthesis, fragment condensation, or F-MOC or T-BOC chemical method (Chemical Approaches to the Synthesis of Peptides and Proteins, Williams et al., Eds., CRC Press, Boca Raton Fla., (1997); A Practical Approach, Atherton & Sheppard, Eds., IRL Press, Oxford, England, (1989)).

The recombinant peptide or chemically synthesized peptide produced by a genetic engineering method can be separated and purified by a method known in the art, for example, extraction, recrystallization, various chromatographic techniques (gel filtration, ion exchange, precipitation, adsorption, reverse phase), electrophoresis, countercurrent distribution, or the like.

The composition according to the present invention may be used as the composition per se or a salt, preferably a pharmaceutically acceptable salt. As used herein, the term "pharmaceutically acceptable" refers to being physiologically acceptable, and not usually causing an allergic response or a similar response when administered to humans. An acid addition salt formed by a pharmaceutically acceptable free acid is preferable as the salt. An inorganic acid and an organic acid may be used as the free acid. Examples of the organic acid include, but are not limited to, citric acid, acetic acid, lactic acid, tartaric acid, maleic acid, fumaric acid, formic acid, propionic acid, oxalic acid, tripleuroacetic acid, benzoic acid, gluconic acid, methanesulfonic acid, glycolic acid, succinic acid, 4-toluenesulfonic acid, glutamic acid, and aspartic acid. In addition, examples of the inorganic acid include, but are not limited to, hydrochloric acid, bromic acid, sulfuric acid, and phosphoric acid.

The composition of the present invention may be variously formulated, together with a pharmaceutically acceptable carrier, in order to exhibit a smooth muscle cell proliferation inhibitory effect, according to the route of administration, by a method known in the art. The carrier includes all kinds of solvents, dispersion media, oil-in-water or water-in-oil emulsions, aqueous compositions, liposomes, microbeads, and microsomes Specific examples of the pharmaceutical carrier are as described in the other part of the specification.

The route of administration may be an oral or parenteral route. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration. Specific examples of the route of administration are as described in the other part of the specification.

The composition containing FGF12 protein or a fragment thereof according to the present invention may be administered to a patient at an amount to exhibit a treatment effect. For a general daily dose, the composition may be administered in the range of 0.0001-100 mg/kg. The composition of the present invention may be administered once or divided into multiple doses within a desired dose range. However, the dose of the composition according to the present invention may be properly selected by a person skilled in the art depending on the route of administration, subject to be administered, age, sex, body weight, individual difference, and disease state.

The present invention provides a composition for diagnosing a smooth muscle cell proliferative disease, the composition comprising an agent for measuring the expression level of FGF12 mRNA or FGF12 protein.

The present inventors found that the expression of FGF12 has a high correlation with the proliferation of smooth muscle cells. FGF12 is highly expressed in smooth muscle cells of healthy blood vessels, but the expression of FGF12 is greatly reduced in smooth muscle cells proliferating in the blood vessels injured by vascular procedures or the blood vessels undergoing arteriosclerosis. In addition, the expression level of FGF12 is significantly reduced by PDGF-BB promoting the proliferation of smooth muscle cells. The measurement of the expression level of FGF12 using a functional correlation between FGF12 and the smooth muscle cell proliferation may be used in the diagnosis of the smooth muscle cell proliferative disease.

The term "diagnosis" refers to identifying the presence or characteristics of a pathological condition. The diagnosis in the present invention is to check the presence or absence of the pathological condition of a smooth muscle cell proliferative disease and to identify the occurrence of the disease or the probability of occurrence of the disease.

In the diagnostic composition of the present invention, the agent for measuring the expression level of FGF12 mRNA may be a probe or a primer set, which specifically binds to FGF12 mRNA.

The FGF12 mRNA in the present invention may comprises a nucleotide sequence represented by SEQ ID NO: 1 or SEQ ID NO: 3.

The "primer" is a short single-stranded oligonucleotide acting as a starting point of DNS synthesis. The primer specifically binds to a polynucleotide as a template under the conditions of suitable buffers and temperature. DNA is synthesized by allowing DNA polymerase to link the nucleoside triphosphate having a base complementary to template DNA to the primer. The primer is generally composed of a 15- to 30-nucleotide sequence, and the melting temperature (Tm) for binding to the template strand varies depending on the nucleotide constitution and length.

The sequence of the primer does not necessarily need to be perfectly complementary to a sequence of some nucleotides of the template, and the primer is good as long as the primer has sufficient complementarity within the range in which the primer can perform the inherent actions thereof through the hybridization with the template. Therefore, the primer for measuring the expression level of FGF12 RNA in the present invention does not necessarily need to be perfectly complementary to the FGF12 gene sequence, and the primer is good as long as the primer has a length and complementarity for the purpose of measuring the amount of FGF12 mRNA by amplifying a specific section of FGF12 mRNA or FGF12 cDNA through DNS synthesis. Primers for the amplification reaction are composed of a set (pair) of primers that complementarily bind to a template (or sense) and an opposite side (antisense), respectively, of both ends of a specific region of the FGF12 mRNA to be amplified. The primers may be easily designed by referring to the nucleotide sequence of FGF12 mRNA or cDNA by a person skilled in the art.

In the present invention, since FGF12 mRNA preferably comprises the nucleotide sequence represented by SEQ ID NO: 1 or SEQ ID NO: 3, the primers of the present invention may be one set or one pair specifically binding to the nucleotide sequence represented by SEQ ID NO: 1 or SEQ ID NO: 3, and most preferably, the primers of the present invention may be a set of nucleotide sequences represented by SEQ ID NO: 15 and SEQ ID NO: 16.

The term "probe" refers to a fragment of a polynucleotide, such as RNA or DNA, capable of specifically binding to mRNA or complementary DNA (cDNA) of a specific gene and having a length of from several to several hundreds of base pairs. The probe is labeled to check the presence or absence of target mRNA or cDNA to be bound or the expression level thereof. For the purpose of the present invention, the probe complementary to FGF12 mRNA can be used for the diagnosis of a smooth muscle cell proliferative disease by measuring the expression level of FGF12 mRNA through the hybridization with a sample of a subject. The selection and hybridization of the probe may be properly selected according to the technique known in the art.

The primers or probes of the present invention may be chemically synthesized using a phosphoramidite solid-phase synthesis method or another well-known methods. In addition, the primers or probes may be variously modified by a method known in the art within the scope in which the hybridization with FGF12 mRNA is not disturbed. Examples of the modification are methylation, capping, substitution of at least one natural nucleotide with an analogue thereof, and modification between nucleotides, for example, modification with an uncharged linker (e. g., methyl phosphonate, phosphotriester, phosphoroamidate, carbamate, etc) or a charged linker (e. g., phosphorothioate, phosphorodithioate, etc), binding with a labeling material using fluorescence or enzyme, and the like.

The agent for measuring the expression level of FGF12 protein in the diagnostic composition in the present invention may be an antibody specifically binding to FGF12 protein.

The FGF12 protein in the present invention may comprise an amino acid sequence represented by preferably SEQ ID NO: 2 or SEQ ID NO: 4.

The term "antibody" refers to an immunoglobulin specifically binding to an antigenic region. The antibody in the present invention is an antibody that binds specifically to only FGF12 protein but does not react with other proteins including other FGF other than FGF12. FGF12 gene is cloned into an expression vector to obtain a protein encoded by the gene, and FGF12 antibody is prepared from the obtained protein by a usual method in the art. The antibody includes a polyclonal antibody or a monoclonal antibody, and includes all immunoglobulin antibodies specifically binding to FGF12.

In the present invention, FGF12 protein preferably comprises an amino acid sequence represented by SEQ ID NO: 2 or SEQ ID NO: 4, while the antibody specifically binding to FGF12 protein may be an antibody specifically binding a protein having an amino acid sequence represented by SEQ ID NO: 2 or SEQ ID NO: 4.

In addition, the present invention provides a method for detecting a marker for a smooth muscle cell proliferative disease, the method, in order to provide information necessary for diagnosis of the smooth muscle cell proliferative disease, comprising:

(a) providing a sample of a subject to be detected;

(b) measuring the expression level of FGF12 in the sample; and (c) comparing the measured expression level of FGF12 with that of a normal subject and determining that the subject is considered to have been afflicted with a smooth muscle cell proliferative disease or to have a probability of being afflicted with a smooth muscle cell proliferative disease in case where the subject has a reduced FGF12 expression level compared with the normal subject.

Hereinafter, the method of the present invention will be described by each step.

In the above method of the present invention, step (a) is to provide a sample of a subject to be detected.

The sample of the subject in step (a) may be smooth muscle cells or a tissue or blood containing smooth muscle cells, and may be preferably vascular smooth muscle cells or blood vessels. The sample of the present invention may be derived from a mammal, and may be preferably derived from humans. The sample of a subject may be provided by collection through a technique known in the art, and for example, blood vessel tissues resected during the vascular procedure or blood may be provided as a sample.

In addition, the sample of a subject may be properly pre-treated according to the method for measuring the expression level of FGF12 as is known in the art. For example, the sample of a subject may be immobilized in a fixative, such as formalin, or may be stored frozen at −20 to −70° C. by rapid freezing using liquid nitrogen or the like. Tissue sections may be prepared from the immobilized or frozen sample, and then stored frozen.

In the method of the present invention, step (b) is to measure the expression level of FGF12 in the sample provided in step (a).

The step for measuring the expression level of FGF12 in step (b) may be the measurement of the expression level of FGF12 mRNA.

With respect to the expression level of FGF12 mRNA, the presence and the expression level of FGF12 mRNA in the sample of a subject may be measured by amplifying FGF12 mRNA or cDNA from the sample of a subject using a primer set or a probe that specifically binds to FGF12 mRNA or by using a hybridization reaction with a probe. The primers and probes are as described in the diagnostic composition of the present invention.

For the determination of the expression level of FGF12 mRNA, conventional methods for determining such expression levels may be used without limitation, while examples of the analysis method include, but are not limited to, reverse transcription polymerase chain reaction (RT-PCR), competitive RT-PCR, real-time RT-PCR, RNase protection assay (RPA), northern blotting, DNA microarray chip, RNA sequencing, hybridization using nano string, or in situ hybridization of tissue sections.

In addition, step (b) may be to measure the expression level of FGF12 protein.

The expression level of FGF12 protein may be detected and measured by using an antibody specifically binding to FGF12 protein. The antibody is as described in the diagnostic composition of the present invention.

As for the measurement method for the expression level of FGF12 protein, methods known in the art may be used without limitation, while exemplary methods may include, but is not limited to, western blotting, dot blotting, enzyme-linked immunosorbent assay, radioimmunoassay (RIA), radial immunodiffusion, Ouchterlony immunodiffusion, rocket immunoelectrophoresis, immunohistochemical staining, immunoprecipitation, complement fixation analysis, flow cytometry (FACS), or a protein chip method.

In the method of the present invention, step (c) is to compare the expression level of FGF12 as measured in step (b) with that of a normal subject and then determine that the subject has been afflicted with a smooth muscle cell proliferative disease or to have a probability of being afflicted with a smooth muscle cell proliferative disease in case where the subject has a reduced FGF12 expression level compared with the normal subject.

The FGF12 expression level of the subject is measured by the method in step (b), while the FGF12 expression level of the normal subject is measured by the same method. Then, the FGF12 expression level of the subject is compared with that of the normal subject. According to the present invention, smooth muscle cells in the healthy normal condition hardly proliferate and express FGF12 at a high level, whereas the FGF12 expression level is remarkably low in proliferating smooth muscle cells due to vascular injury or disease. Therefore, the smooth muscle cells can be determined to proliferate when the FGF12 expression level of the subject is reduced compared with that of the normal subject.

In addition, the subject can be determined to have a probability of being afflicted with a smooth muscle cell proliferative disease, to have already been afflicted with the disease, or to have the disease progressed, according to the degree of reduction in FGF12 expression level. The degree of reduction in FGF12 expression level, which may be used as the criteria of diagnosis, can be determined by grading the degree of its expression level suitable for a specific method for measuring such expression levels according to the techniques known in the art. For example, the FGF12 expression level may be measured in samples of a plurality of normal subjects and a plurality of patients, followed by accumulation and analysis of the obtained data, so that a proper criteria for diagnosis can be provided by classifying into a normal category, a smooth muscle cell proliferative disease category (or a severe disease category), or a disease likelihood category according to the degree of FGF12 expression level.

Specifically, the methods according to the present invention are particularly shown in Examples.

In an Example of the present invention, it was confirmed through immunofluorescent staining that the proliferating smooth muscle cells expressing Ki67 were remarkably increased and the protein expression level of FGF12 was greatly reduced in the rat common carotid arteries injured by the balloon embolectomy catheter, in comparison with the uninjured normal arteries. Meanwhile, as the vascular injury was restored, the number of proliferating smooth muscle cells was decreased and the protein expression level of FGF12 was increased to a similar level to a normal condition. The tendency of reduction and enhancement in the FGF12 expression level according to the vascular injury and restoration was also confirmed using the mRNA level through RT-PCR.

In another Example of the present invention, it was confirmed that the FGF12 protein was highly expressed in the smooth muscle cells of mouse arteries in a normal condition, whereas the smooth muscle cell proliferation was increased and the expression of FGF12 protein was greatly reduced in the arteries of $Apo^{-/-}$ mice fed with high fat diet. It was also confirmed through immunofluorescent staining experiments that the FGF12 protein expression was also greatly reduced in the human atherosclerotic artery tissues like in animal experiments.

In still another Example of the present invention, it was confirmed through immunofluorescent staining, RT-PCR and Western blotting that the FGF12 protein expression in the pulmonary vascular smooth muscle cells was greatly reduced in experimental rats having pulmonary arterial hypertension induced by monocrotaline (MCT) injection, compared with the control group administered with saline.

In further another Example of the present invention, it was confirmed that the overexpression of FGF12 in the lungs of pulmonary arterial hypertension-induced rats by monocrotaline (MCT) injection stimulated the differentiation of vascular smooth muscle cells in the pulmonary artery, and significantly decreased the thickness of the vascular endothelial and mesenchymal walls composed of vascular smooth muscle cells, resulting in the widened internal diameter of the blood vessel.

The present invention provides a use of a recombinant expression vector comprising a polynucleotide encoding FGF12 for preparing an agent for treating a smooth muscle cell proliferative disease.

The present invention provides a method for treating a smooth muscle cell proliferative disease in a subject in need thereof, the method comprising administering an effective amount of a composition for treating a smooth muscle proliferative disease to a subject in need thereof, the composition comprising, as an active ingredient, a recombinant expression vector comprising a polynucleotide encoding FGF12.

The present invention provides a use of FGF12 protein or a fragment thereof for preparing an agent for treating a smooth muscle cell proliferative disease.

The present invention provides a method for treating a smooth muscle cell proliferative disease in subject in need thereof, the method comprising administering an effective amount of a composition for treating a smooth muscle proliferative disease to a subject in need thereof, the composition comprising, as an active ingredient, FGF12 protein or a fragment thereof.

The present invention provides a use of an agent for measuring the expression level of FGF12 mRNA or FGF12 protein for preparing an agent for diagnosing a smooth muscle cell proliferative disease.

The present invention provides a method for diagnosing a smooth muscle cell proliferative disease, the method comprising administering an effective amount of a composition for diagnosing a smooth muscle proliferative disease to a subject in need thereof, the composition comprising an agent for measuring the expression level of FGF12 mRNA or FGF12 protein.

As used herein, the term "effective amount" refers to an amount which exhibits an alleviation, treatment, prevention, detection, or diagnosis effect of a smooth muscle cell proliferative disease when the composition is administered to a patient. As used herein, the term "subject" refers to an animal, preferably a mammal, especially an animal including a human being, and may be cells, tissues, organs, or the like derived from an animal. The subject may be a patient in need of treatment.

The term "treatment" of the present invention refers collectively to alleviation of symptoms of a smooth muscle cell proliferative disease, may include healing, substantially preventing, or improving the condition of such a disease, and may include alleviating, healing, or preventing one symptom or most symptoms resulting from a smooth muscle cell proliferative disease, but it not limited thereto.

Hereinafter, the present invention will be described in detail.

However, the following examples are merely for illustrating the present invention, and are not intended to limit the scope of the present invention.

Experimental Methods

Animal Experiments

Animal experiments were conducted using 9- to 10-week-old male Sprague-Dawley (SD) rats (Orient) and apolipoprotein E-knockout (ApoE−/−) mice (Japan SLC). The rats were fed a normal chow diet and were given water ad libitum. ApoE−/− mice were fed a normal diet or western-type high-fat diet (HFD; 42% of total calrories from fat, 0.15% cholesterol; REsearch Diets) for 4 weeks. All animals were cared for in accordance with the Guide for the Care and Use of Laboratory Animals published by the United States National Institutes of Health. Protocols for all animal experiments were approved by the Institutional Animal Care and Use Committee. For surgical procedures, mice and rats were anesthetized by intraperitoneally injecting ketamine (mice, 79.5 mg/kg; rats, 80 mg/kg) and xylazine (mice: 9.1 mg/kg; rats 5 mg/kg). The adequacy of anesthesia induction was assessed by monitoring the pedal withdrawal reflex.

Rat Model of Carotid Artery Injury

For inducing carotid artery balloon injury, SD rats were anesthetized and their common carotid artery was exposed by making a midline cervical incision. A 2F Fogarty balloon embolectomy catheter (Baxter) was introduced through the external carotid artery and was advanced into the thoracic aorta. The catheter was inflated and was withdrawn into the entry point. The entire procedure was repeated 3 times. For gene transfer using adenovirus, $1\times10^9$ plaque-forming units/100 ml adenoviruses were injected into the ligated segment of the common carotid artery for 30 min. The external carotid artery was then permanently ligated, and blood flow in the common carotid artery was restored. Two weeks after balloon injury, the common carotid arteries were collected for histological evaluation.

Morphometric Analysis

For morphometric analysis, the carotid arteries were fixed, dehydrated, and embedded in paraffin. Carotid artery sections (5 µm) were stained with hematoxylin and eosin. The morphometric analysis was performed using three sections isolated from the middle of each injured arterial segment by an investigator blinded to the experimental conditions. The intima/media area ratios (I/M), luminal stenosis (%), and neointimal area were measured using NIS Elements Imaging Software (Nikon).

Human Arteriosclerotic Tissue Specimens

The protocol for clinical research was approved by a local ethical committee (IRB2014-04-077; Samsung Medical Center, Republic of KOREA), and informed consent was obtained from all patients. Human arteriosclerotic tissues were obtained from patients who underwent carotid endarterectomy. For immunohistochemical examination, the collected tissues were fixed in formalin and were embedded in paraffin.

Pulmonary Arterial Hypertension Animal Models

For construction of rat pulmonary arterial hypertension animal models, SD rats were divided into a control group and a monocrotaline group. Monocrotaline (300 mg, MCT) was dissolved in 1.8 ml of 1 M HCl, added with 3-4 ml of distilled water, adjusted to pH 7.4 with 1M NaOH, and added with distilled water, thereby making 15 ml of an aqueous solution. The monoclotharin group was subcutaneously injected once with the monocrotaline aqueous solution (60 mg/kg), while the control group was subcutaneously injected with the same amount of physiological saline. For experiments, the animals at 5 weeks after monocrotaline injection were sacrificed.

In the experiment on the effect of the overexpression of FGF12 in treating pulmonary arterial hypertension, PBS or adenovirus ($3\times10^9$ plaque forming unit) was intratracheally injected with a microspray aerosolizer (PennCentury) after 2 weeks of monocrotaline (MCT) injection into rats. Three weeks after the adenovirus administration, 4% paraformaldehyde was perfused to fix the lung tissues of the rats, followed by histological examination. In addition, heart tissues were collected to measure the weight of the right and left ventricles.

Immunofluorescence Staining

Tissue sections and cells were stained with primary antibody against Ki67 (Dako Inc.), FGF12 (Abcam), phospho-p53 (p-p53; Cell Signaling Technology), α-smooth muscle actin (α-SMA; Sigma), or SM22α (Abcam) and proper fluorescence-labeled secondary antibody. Nuclei were stained with 4',6-diamidino-2-phenylindole (DAPI). The stained cells were observed using a fluorescence microscope (Nikon). All images shown are representative of independent three experiments.

Reverse Transcription-Polymerase Chain Reaction

Total RNA of cells or tissues for reverse transcription-polymerase chain reaction (RT-PCR) was isolated with TRIzol reagent (Invitrogen). Next, cDNA was synthesized from total RNA using primers specific to corresponding genes and a Superscript first-strand synthesis kit (Invitrogen), and was amplified by PCR (30-35 cycles). Glyceraldehyde-3-phosphate dehydrogenase (GAPDH) was used as a loading control. Real-time PCR was performed using a SYBR-Green PCR master mix (Applied biosystems) and the StepOnePlus™ Real Time PCR System (Applied Biosystems). Data were analyzed according to ΔΔCt method, and gene expression values were normalized to GAPDH expression. The primers used in PCR are listed in Table 1 below.

TABLE 1

| Nucleotide Sequences of Primer | | |
|---|---|---|
| Primer | Forward (5' to 3') | Reverse (5' to 3') |
| Rat FGF12 | GCGATAGCCAGCTCCTTGAT (SEQ ID NO: 5) | GAAGCGCACTTTGCTGAACA (SEQ ID NO: 6) |
| Rat SM-MHC | AAAGCCAGATGTCCGAAGCA (SEQ ID NO: 7) | AGATCTGCTACTGGGGTGGA (SEQ ID NO: 8) |

TABLE 1-continued

Nucleotide Sequences of Primer

| Primer | Forward (5' to 3') | Reverse (5' to 3') |
|---|---|---|
| Rat SM22α | ACCAAGCCTTTTCTGCCTCAA (SEQ ID NO: 9) | GGTTCTCAGGCACCTTCACT (SEQ ID NO: 10) |
| Rat SRF | ACGACCTTCAGCAAGAGGAA (SEQ ID NO: 11) | GAGAGTCTGGCGAGTTGAGG (SEQ ID NO: 12) |
| Rat GAPDH | CTCATGACCACAGTCCATGC (SEQ ID NO: 13) | TTCAGCTCTGGGATGACCTT (SEQ ID NO: 14) |
| Human FGF12 (total) | GCGATAGCCAGCTCCTTGAT (SEQ ID NO: 15) | GAAGCGCACTTTGCTGAACA (SEQ ID NO: 16) |
| Human FGF12 (exo) | AGCTTGGTTTCTGGGACTCA (SEQ ID NO: 17) | CTCTTCTGAGATGAGTTTCTGCTC (SEQ ID NO: 18) |
| Human CDK1 | AAACTGGCTGATTTTGGCCT (SEQ ID NO: 19) | GGAGTGCCCAAAGCTCTGAA (SEQ ID NO: 20) |
| Human CDK2 | CTCCAGGGCCTAGCTTTCTG (SEQ ID NO: 21) | TTCAGGAGCTCGGTACCACA (SEQ ID NO: 22) |
| Human CCNA2 | TGCATCTCTGGGCGTCTTTG (SEQ ID NO: 23) | ACCCGGCCAAAGAATAGTCG (SEQ ID NO: 24) |
| Human CDC6 | AAGGGCGTTGGGGTCATAAG (SEQ ID NO: 25) | GGCTTCATCTAAGGGCAGCA (SEQ ID NO: 26) |
| Human CDC20 | GCAAGCTCTGGTGACATCCT (SEQ ID NO: 27) | ACATGGTGTTCTGCTACCCG (SEQ ID NO: 28) |
| Human SM-MHC | ATGAGGCCACGGAGAGCAACGA (SEQ ID NO: 29) | CCATTGAAGTCTGCGTCTCGA (SEQ ID NO: 30) |
| Human p53 | AGCGATGGTCTGGCCCCTCCT (SEQ ID NO: 31) | CTCAGGCGGCTCATAGGGCAC (SEQ ID NO: 32) |
| Human p21 | TTGCCGACAGGATGCAGAAG (SEQ ID NO: 33) | AGGTGGACAGCGAGGCCAGG (SEQ ID NO: 34) |
| Human GAPDH | GAAGGTGAAGGTCGGAGTC (SEQ ID NO: 35) | GAAGATGGTGATGGATTTC (SEQ ID NO: 36) |
| Human ID3 | GAGGCACTCAGCTTAGCCAG (SEQ ID NO: 46) | ATGACAAGTTCCGGAGTGAGC (SEQ ID NO: 47) |
| Human α-SMA | AGCGACCCTAAAGCTTCCCA (SEQ ID NO: 48) | CATAGAGAGACAGCACCGCC (SEQ ID NO: 49) |
| Human SM22α | GGAGCAGTGGGTGCATTTCA (SEQ ID NO: 50) | TGCACTAGCCAAGTCATCCG (SEQ ID NO: 51) |
| Human BMPR2 | AGGAAGATAATGCAGCCATA (SEQ ID NO: 52) | TGGGAAGAGGTCTGTACATC (SEQ ID NO: 53) |

Cell Culture

Human aortic vascular smooth muscle cells (HASMCs; ScienCell Research Laboratories) and human pulmonary aortic vascular smooth muscle cell (HPASMC, ScienCell Research laboratories) were cultured in smooth muscle growth medium (SMGM, ScienCell Research Laboratories) or basal medium. For a compound inhibitor experiment, HASMCs and HPASMCs were pre-treated with pifithrin (10 µM; Sigma), LY294002 (20 µM; Cell Signaling Technology), PD98059 (50 µM; Cell Signaling Technology), U0126 (10 µM; Cell Signaling Technology), SB203580 (50 µM; Cell Signaling Technology), and BIRB796 (10 µM; Merck) at 37° C. for 24 hours.

Transfection

For transfection for FGF12 overexpression, an expression vector (pCMV6-Entry having the c-terminal labeled Myc-DDK) encoding a rat homologous gene (Origene) having 100% amino acid homology with human FGF12 cDNA was used. HASMCs and HPASMCs were transfected with pCMV6-FGF12(pFGF12) or pCMV6-Entry (pEntry) control vector using Lipofectamien™ 2000 according to the protocol of the manufacturer, and selected using G418 (Sigma) for 2 weeks. For the inhibition of FGF12, p53 or BMPR2 expression, subconfluent HASMCs were transfected with specific or non-specific small interfering RNA (siRNA; GE Healthcare) using Lipofectamien™ 2000. The siRNA nucleotide sequences are shown in Table 2.

TABLE 2

Nucleotide Sequences of siRNA

| siRNA Target Gene | siRNA sequence (5' to 3') |
|---|---|
| Human FGF12 | 1. AAACAAGGGCGUUCAAGGA (SEQ ID NO: 37)<br>2. GGTGAAGGCUAUCUCUACA (SEQ ID NO: 38)<br>3. AACCAUCGCUACAUGAAAU (SEQ ID NO: 39)<br>4. CUAUUGAAGUGUGUAUGUA (SEQ ID NO: 40) |
| Human p53 | 1. GAAAUUUGCGUGUGGAGUA (SEQ ID NO: 41)<br>2. GUGCAGCUGUGGGUUGAUU (SEQ ID NO: 42)<br>3. GCAGUCAGAUCCUAGCGUC (SEQ ID NO: 43)<br>4. GGAGAAUAUUUCACCCUUC (SEQ ID NO: 44) |
| Human BMPR2 | 1. GAACGCAACCUGUCACAUA (SEQ ID NO: 54)<br>2. GCAUGAGCCUUUACUGAGA (SEQ ID NO: 55)<br>3. GAAACAAGUAGACAUGUAU (SEQ ID NO: 56)<br>4. GAAGGUGGCCGAACUAAUU (SEQ ID NO: 57) |
| Control siRNA | AAUGGAAGACCACUCCCACUC (SEQ ID NO: 45) | cDNA Microarray p cDNA microarray analysis were performed according to the manufacturer's protocol (Affymetrix Genchip Human Gene 1.0 ST oligonucleotide array). Briefly, biotin-labeled cDNA was synthesized from the equivalent amount of total RNA using the RNeasy Mini Kit column (Qiagen Inc.). cDNA probe hybridization was performed according to the Gene Chip Whole Transcript Sense Target Labeling Assay manual (Affymetrix), and chip was scanned using the Genechip Array scanner 3000 7G (Affymetrix), and the scanned images were analyzed using the Affymetrix command console software (version 1.1). A probe with $p<0.05$ was used for analysis, and normalization was performed according to the Robust Multi-array Average normalization method. Transcripts with a 2-fold or higher expression level difference were defined as differentially expressed genes (DEGs). The derived DEGs was subjected to gene ontology (GO) term enrichment analysis using the Database for Annotation, Visualization and Integrated Discovery (DAVID).

Cell Cycle Analysis

For cell cycle analysis, the cells were serum-deprived, and stimulated with SMGM for 24 hours. Next, the cells were trypsinized, washed, and fixed with 70% ethanol at −20° C. The cells were then resuspended in the propidium iodide (PI) buffer (50 µg/ml PI, 0.1% Triton-X, 0.1 mM EDTA, 0.05 mg/ml RNase), and analyzed using the BD FACSCalibur (Becton, Dickinson and Company). Cell cycle distribution was analyzed using software.

Cell Poliferation Aalysis

For cell proliferation analysis, cells were inoculated triplicate in a 24-well plate, and cultured in the basal medium supplemented with 50 ng/ml platelet-derived growth factor-BB (PDGF-BB; R&D systems), 100 ng/ml Bone morphogenic protein-4 (BMP-4; R&D systems), or 10% FBS. Cell proliferation was determined by an MTS assay (MTS assay; Promega) or immunofluorescence assay using anti-Ki67 IgG (Dako). Five representative color images were randomly acquired from each sample for quantifying Ki67 stained cells (Ki67+ cells), and the percentage of Ki67+ cells was determined through dividing the mean value of Ki67+ cells by the total number of cells on each image.

Luciferase Reporter Assay

For the luciferase reporter assay, approximately 2000 base pairs of the FGF12 5'-UTR were cloned into a firefly luciferase reporter vector (pGL3-phFGF12). HASMCs were co-transfected with an empty vector (pGL3-basic) or pGL3-phFGF12, together with a constitutively active β-galactosidase reporter plasmid as a transfection control. After 48 hours, luciferase and galactosidase activities were analyzed using a luciferase and galactosidase assay kit (Stratagene). The luciferase activity was normalized to galactosidase activity, and expressed as a relative value compared with the luciferase activity measured in HASMCs transfected with pGL3-basic and cultured in a medium containing PDGF-BB (50 ng/ml) for 1 day.

Preparation of Adenovirus

For the preparation of adenovirus encoding FGF12, an expression vector (pCMV6-Entry having Myc-DDK-labeled c-terminus) encoding mouse homologous gene (Origene) having 100% amino acid sequence homology with human FGF12 cDNA was used. Human FGF12 cDNA was subcloned into a pShuttle-CMV vector to construct the recombinant adenoviral plasmid using pAdEasy-1 vector (Qbiogene). A recombinant adenovirus used for the experiment was prepared and purified by ViraQuest Inc.

Western Blotting

Cell and tissue lysates were separated by SDS-PAGE, and protein bands were transferred on blots. Blots were reacted with appropriate primary antibodies such as FGF12 (Abcam), p-p53 (Cell Signaling Technology), p53 (BD Biosciences), α-SMA (Sigma), SM22α (Abcam), SM-MHC, or β-actin (Santa Cruz biotechnology), followed by treatment with horseradish peroxidase-conjugated secondary antibodies. The protein bands reacted with antibodies were confirmed by a chemiluminescent reagent (Amersham Biosciences).

Statistical Analysis

All data are presented as mean±SEMs. Statistical significance was evaluated using one way analysis of variance followed by Bonferroni's post hoc multiple comparison test. A p-value of <0.05 was considered statistically significant. The number of samples is indicated by using n.

Experimental Results

Example 1

Differential Expression Profiles of FGF12 in Injured Arteries 1-1. Reduction in FGF12 Expression in Balloon-Injured Arteries The expression pattern of FGF12 in the injured arteries was examined.

Figure 1A:
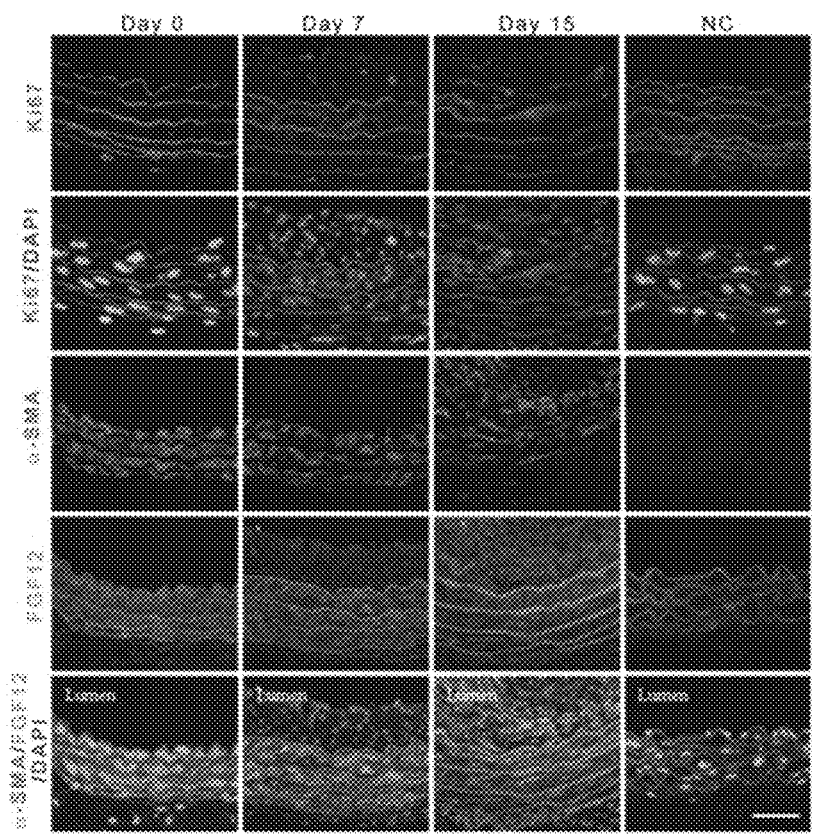
FIG. 1A and FIG. 1B show experimental results to confirm the expression pattern of FGF12 over time after injury in rat carotid arteries injured due to balloon injury.
Figure 1B:
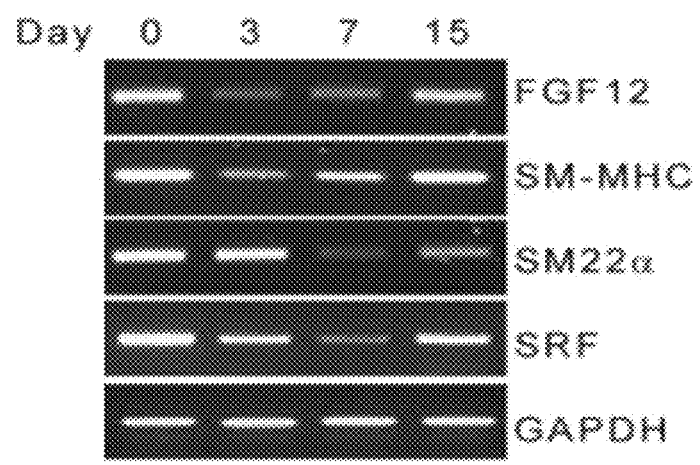

FGF12 was highly expressed in α-SMA-expressing (α-SMA+) smooth muscle cells (SMCs) in the medial layers of the normal rat aorta (day 0, FIG. 1A). However, FGF12 expression was remarkably reduced in the neointimal layers of proliferating (Ki67+) and α-SMC-not-expressing (α-SMA−) non-contractile SMCs on day 7 after balloon injury. On day 15 when partial recovery from injury was observed, the FGF12 level was again increased in α-SMA+ smooth muscle cells in the neointimal layers. RT-PCR confirmed that vascular injury-induced changes in FGF12 expression level were in parallel over time with the expression of the smooth muscle cell contractile markers SM-MHC, SM22α, and SRF (FIG. 1B).

1-2. Reduction in FGF12 Expression in Arteriosclerosis

The expression pattern of FGF12 in the arteries undergoing arteriosclerosis was examined.

Figure 2A:
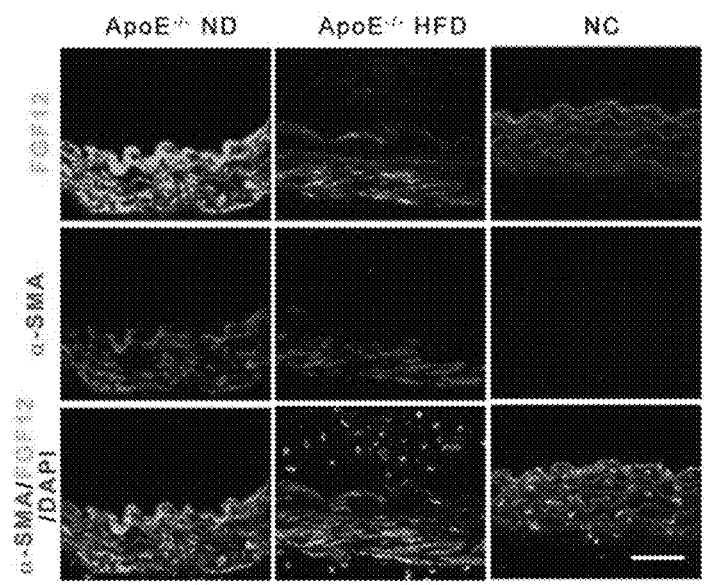
FIG. 2A and FIG. 2B show experimental results to confirm the expression patterns of FGF12 in the arteries of mice and humans with undergoing arteriosclerosis.
Figure 2B:
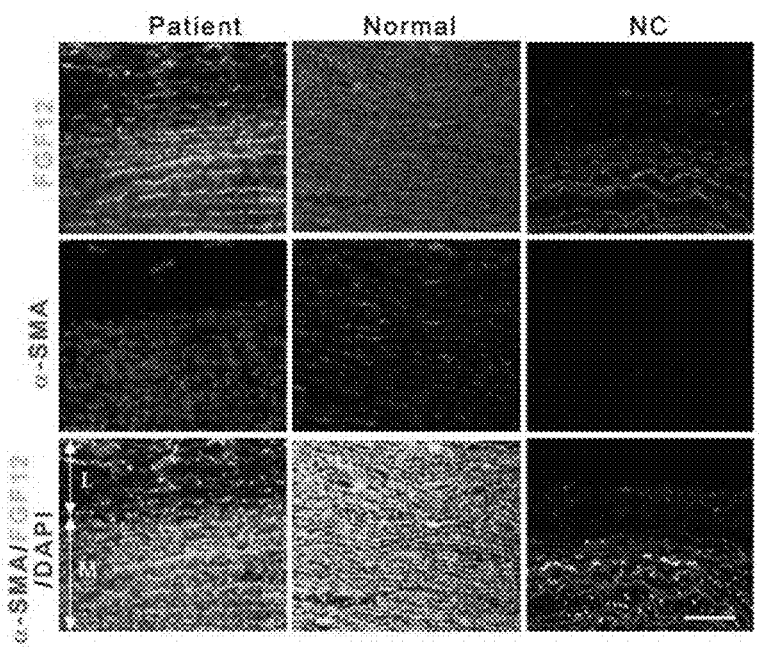

In high-fat diet-fed ApoE$^{-/-}$ mice as arteriosclerosis animal models, the FGF12 expression patterns in the arteries were shown to almost coincide with the α-SMA expression pattern in the aortic plaques (FIG. 2A). In the immunohistochemical analysis of atherosclerotic tissue specimen of human arteriosclerotic patient, FGF12 was selectively expressed in α-SMC+ medial layer smooth muscle cells, and the FGF12 expression was significantly reduced in α-SMC+ smooth muscle cells of arteriosclerosis-injured site. These results coincide with those in the animal models (FIG. 2B).

1-3. Reduction in FGF12 Expression in Pulmonary Artery Hypertension

The expression pattern of FGF12 was examined in pulmonary artery hypertension animal models.

Figure 3A:
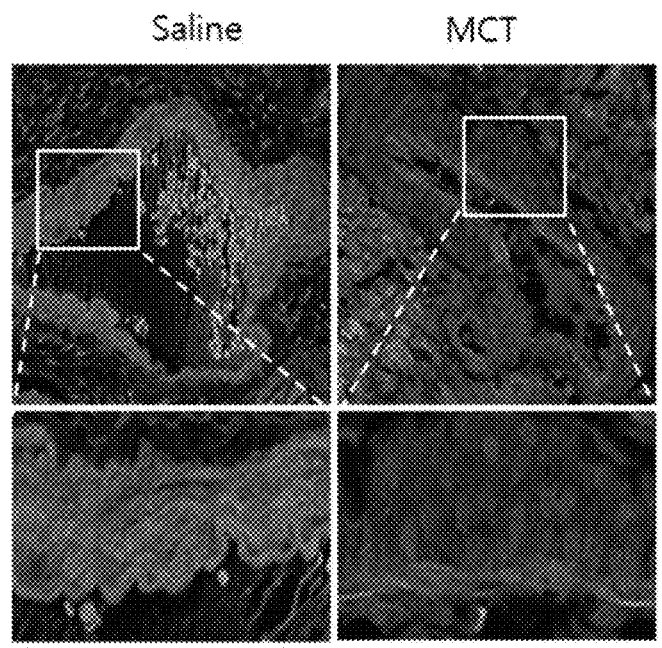
FIG. 3A, FIG. 3B and FIG. 3C show experimental results to confirm the expression patterns of FGF12 in pulmonary vascular smooth muscle cells of pulmonary arterial hypertension animal models prepared by injecting monocrotaline (MCT) into rats.
Figure 3B:
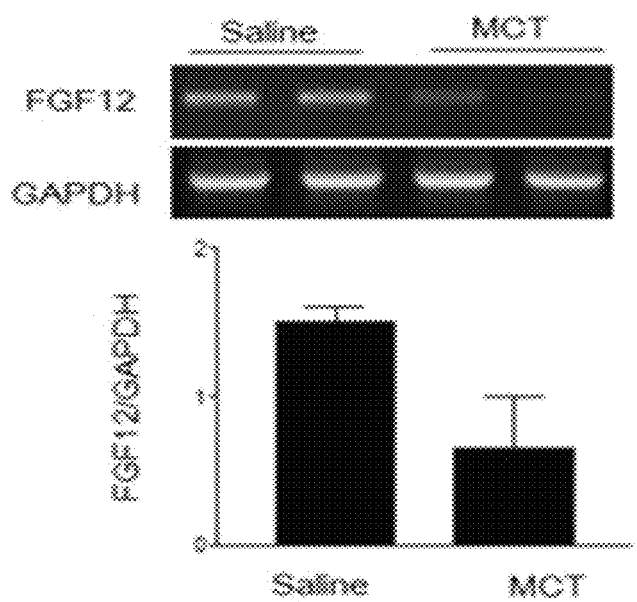
Figure 3C:
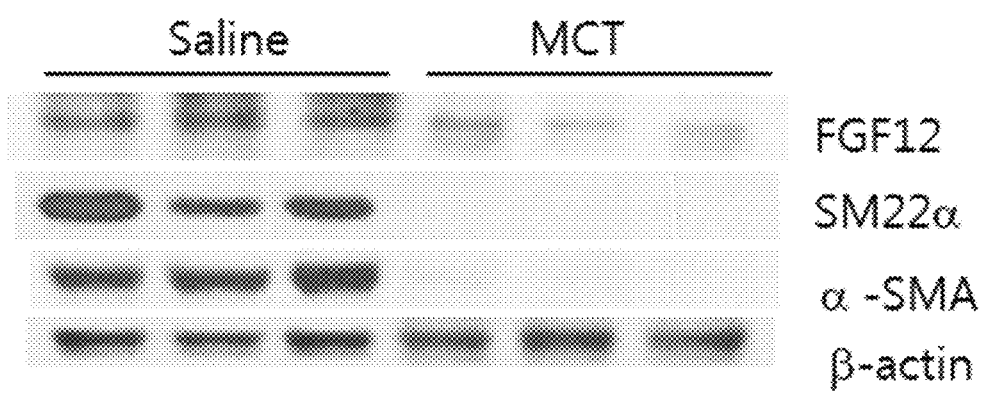

FGF12 expression was remarkably reduced in pulmonary artery hypertension animal model induced by monocrotaline (MCT) injection (FIG. 3A, MCT), and a high expression pattern was shown in normal rats (FIG. 3A, saline). It was confirmed from FGF12 expression pattern confirmed through RT-PCR that FGF12 gene was remarkably reduced in the MCT-injected group compared with the saline-injected group (FIG. 3B). Western blotting also shows the significantly reduced expression of FGF12 protein as well as vascular smooth muscle cell differentiation markers (α-SMA, SM22α) in MCT-injected animals (FIG. 3C).

The above experimental results show that the FGF12 expression level is closely associated with the proliferation of vascular smooth muscle cells. That is, FGF12 is highly expressed in non-proliferating smooth muscle cells, whereas the expression level of FGF12 is remarkably reduced in proliferating smooth muscle cells.

Example 2

FGF12 Expression Regulation by Vascular Smooth Muscle Cell Proliferation Factor PDGF-BB It was examined whether the FGF12 expression is regulated by a potent vascular smooth muscle cell mitogen PDGF-BB.

Figure 4A:
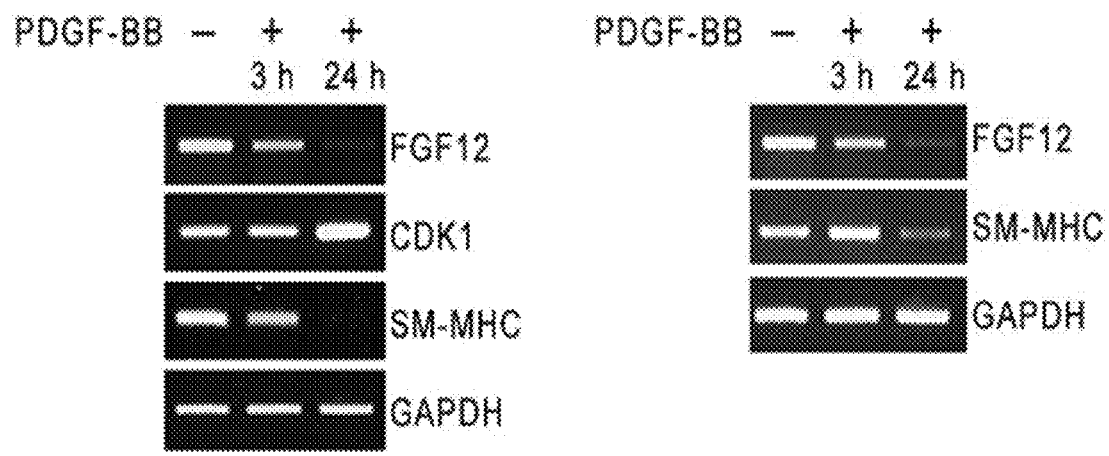
FIG. 4A, FIG. 4B, FIG. 4C and FIG. 4D show experimental results illustrating that FGF12 expression is regulated by PDGF-BB.
Figure 4B:
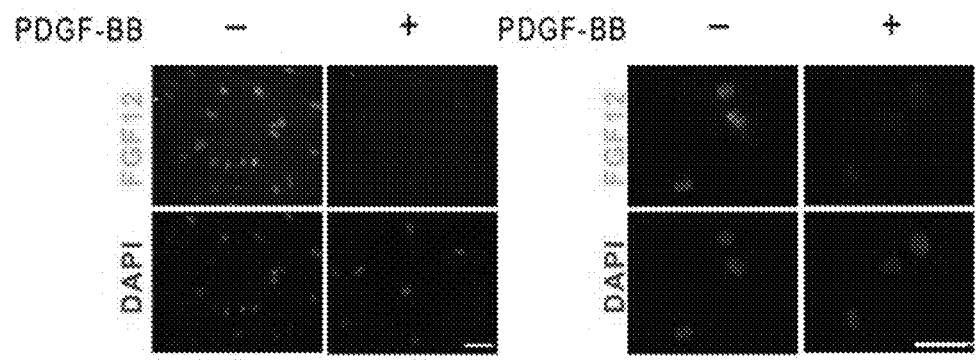
Figure 4C:
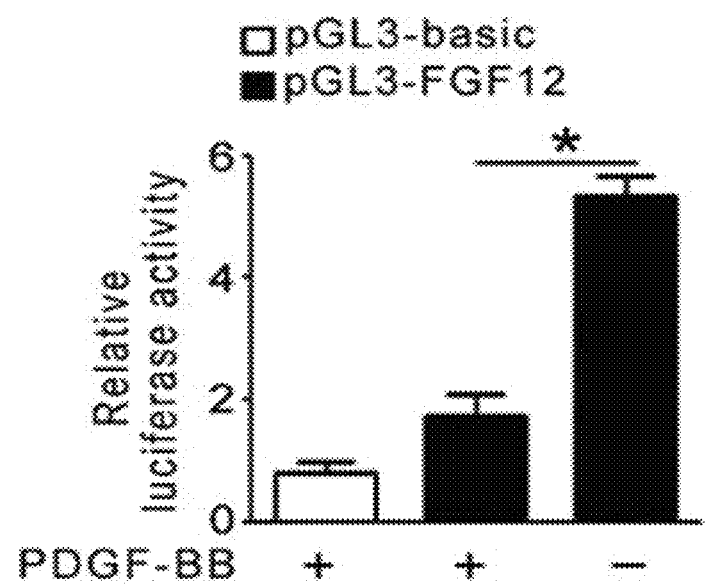

It was confirmed through RT-PCR that the mRNA level of FGF12 was greatly decreased in human aortic smooth muscle cells (HASMCs) and human pulmonary aortic vascular smooth muscle cells (HPASMCs) 3 hours after PDGF-BB was added to basal medium (FIG. 4A). After 24 hours of PDGF-BB stimulation, the mRNA level of FGF12 was further decreased, the mRNA level of the proliferation marker gene CDK1 was increased, and the mRNA level of the contractible gene SM-HMC was decreased. It could also be confirmed through the immunofluorescent experiment that the expression level of FGF12 was decreased in HASMCs and HPASMCs treated with PDFGF-BB (FIG. 4B). It was observed from the reporter experimental results using FGF12 promoter that the transcriptional activity of the FGF12 promoter was remarkably increased when PDGF-BB was removed from the basal medium (FIG. 4C), which verifies that PDGF-BB inhibits the expression of FGF12 at a transcriptional level.

Figure 4D:
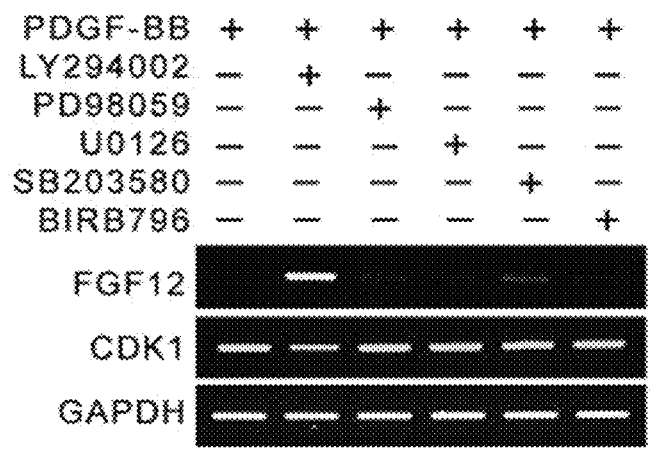

In order to examine FGF12 expression regulation mechanism by PDGF-BB signaling system, the expression pattern of FGF12 was examined through RT-PCR after the treatment with various signaling inhibitors (FIG. 4D). The PI3 kinase (PI3K) inhibitor LY294002 abolished the PDGF-BB-induced decrease in FGF12 expression in HASMCs. However, MEK, ERK, or p38 MAPK signaling inhibitors did not affect the expression of FGF12. That is, it shows that PDGF-BB inhibited the transcription of FGF12 gene through PI3K signaling. Similarly, it was confirmed that the expression of FGF12 was significantly reduced in HASMCs and HPASMCs stimulated with FBS, which promotes the proliferation of vascular smooth muscle cells (data not shown).

Example 3

Inhibition of Vascular Smooth Muscle Cell Proliferation by FGF12

3-1. Gene Expression Regulation by FGF12

It was examined whether FGF12 can regulate the proliferation of vascular smooth muscle cells, through the gain-of-function experiment for FGF12 overexpression in HASMCs and the gene assay profile analysis using microarray.

Figure 5A:
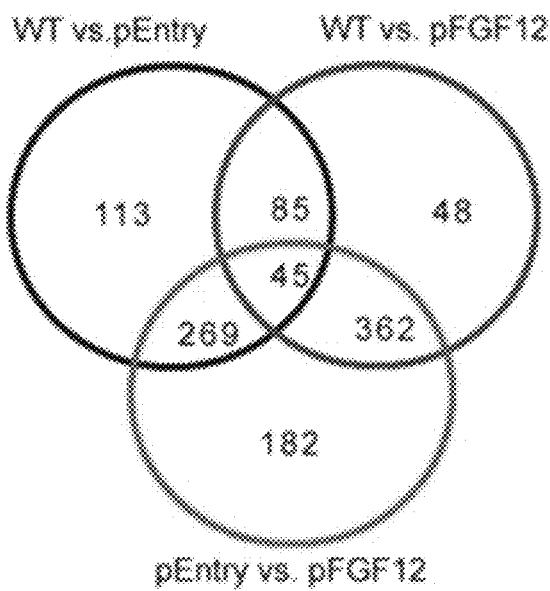
FIG. 5A shows Venn diagram showing the number of DEGs determined by multiple comparisons of untransfected wild-type (WT) HASMC, pCMV6-Entry-transfected HASMCs (pEntry), and pCMV6-FGF12-transfected HASMCs (pFGF12).
Figure 5B:
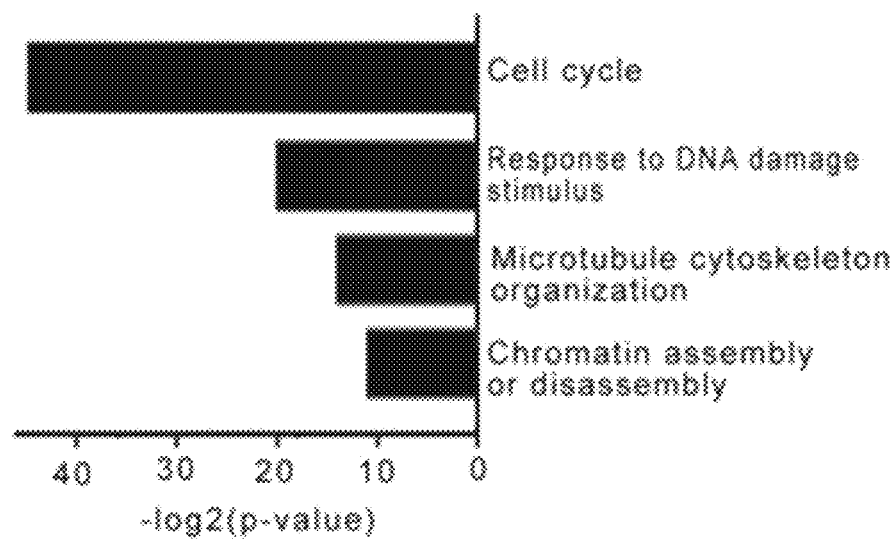
FIG. 5C, FIG. 5B, and FIG. 5C show experimental results illustrating the analysis of genes of which expression is regulated by FGF12 in HASMCs.
Figure 5C:
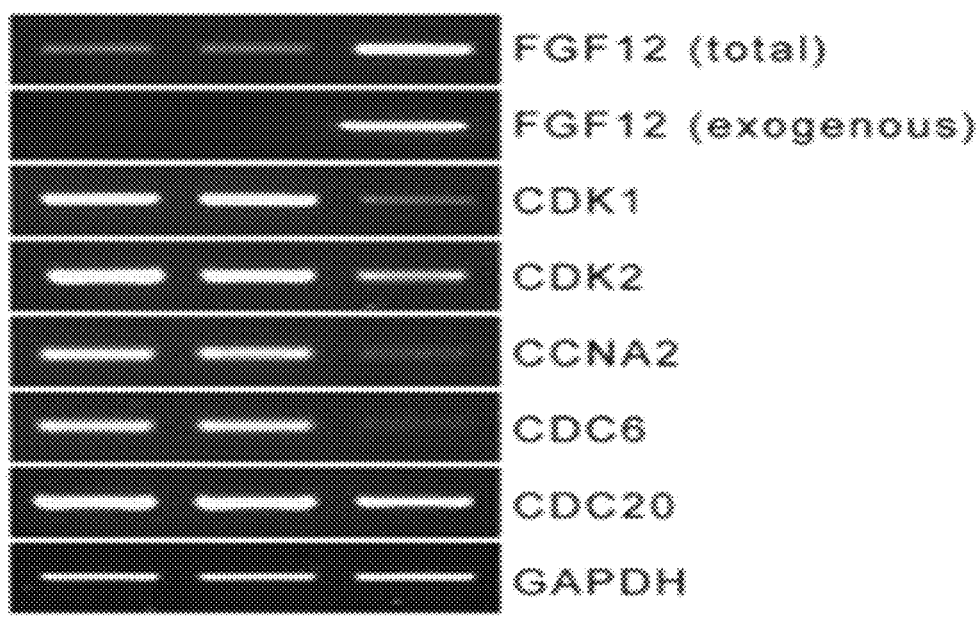

The results of comparative analysis of gene expression profile confirmed that 362 genes were commonly differentially expressed between FGF12-overexpressing HASMCs (pFGF12) and two types of control groups (wild type (WT) HASMCs and HASMCs transfected with an empty vector (pEntry) (FIG. 5A). The results of GO enrichment analysis of the 362 DEGs showed that biological processes, such as cell cycle, responses to DNA damage, microtubule cytoskeleton organization, and chromatic assembly and disassembly, were profoundly altered in FGF12-overexpressing HASMCs (FIG. 5B). Particularly, it was confirmed through RT-PCR that the expression of several genes (CDK1, CDK2, CCNA2, CDC6, CDC20) involved in cell cycle progression was remarkably decreased in FGF12-overexpressing HASMCs (FIG. 5C).

3-2. Inhibition of Cell Division by FGF12

The effect of FGF12 expression on cell cycle was further examined.

Figure 6A:
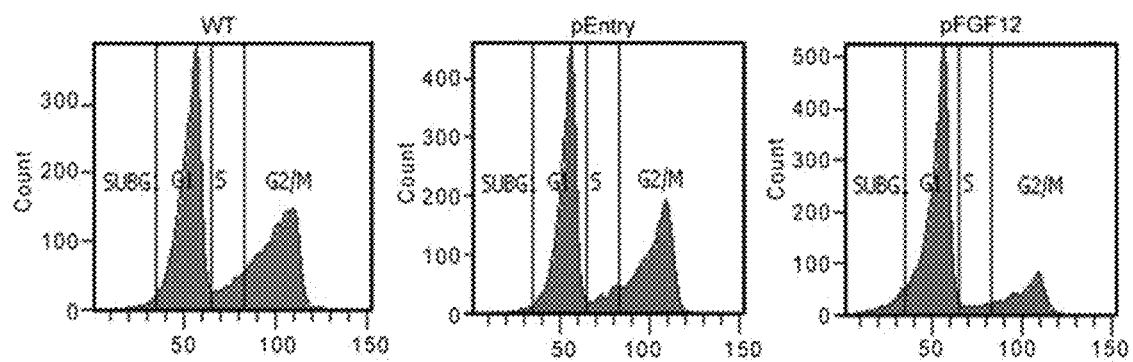
FIG. 6A, FIG. 6B, FIG. 6C, FIG. 6D, and FIG. 6E show experimental results illustrating the effect of FGF12 on cell cycle.
Figure 6B:
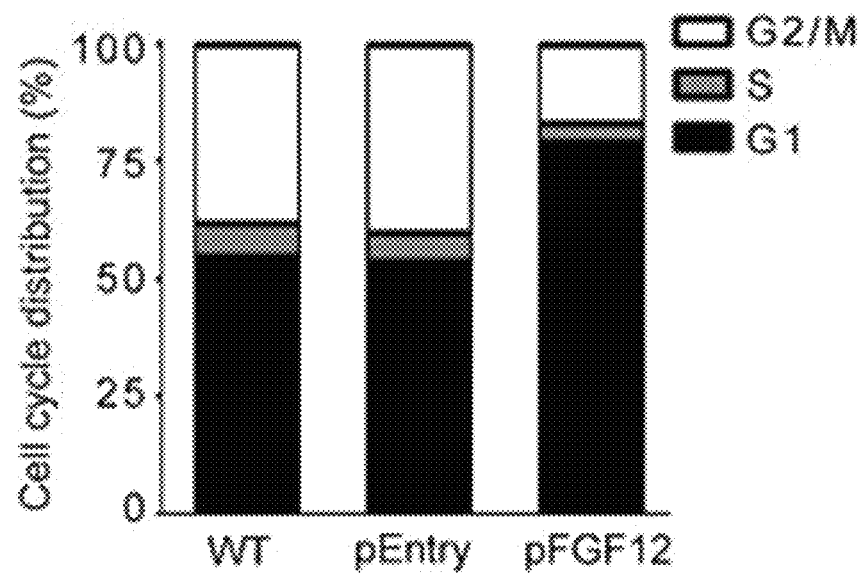
Figure 6C:
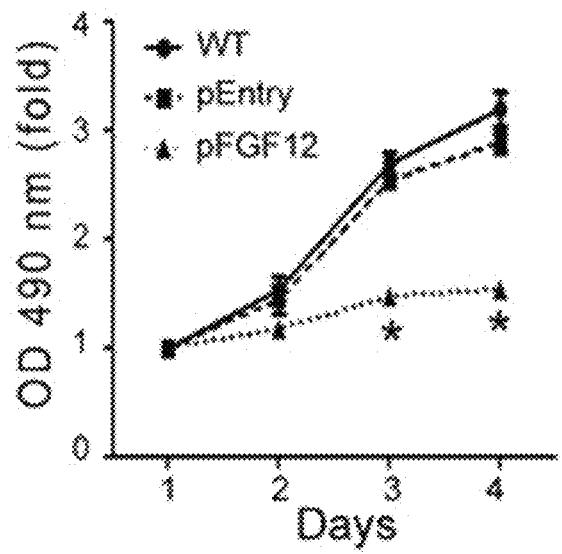
Figure 6D:
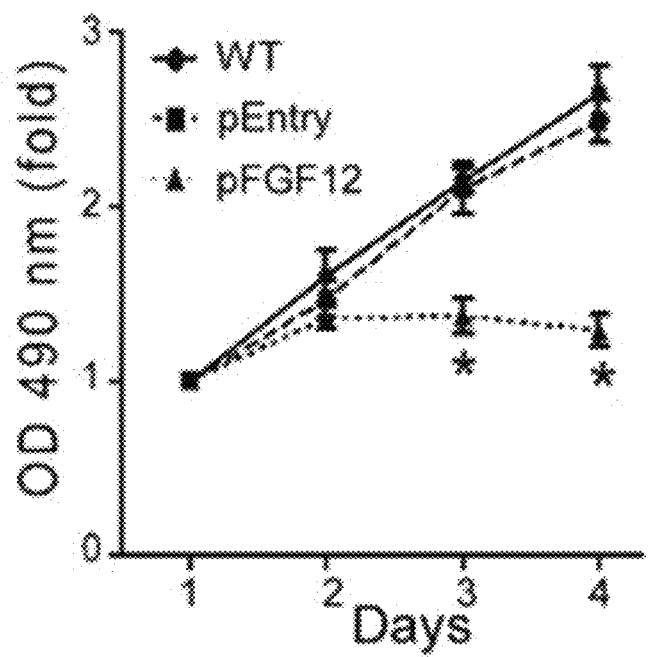
Figure 6E:
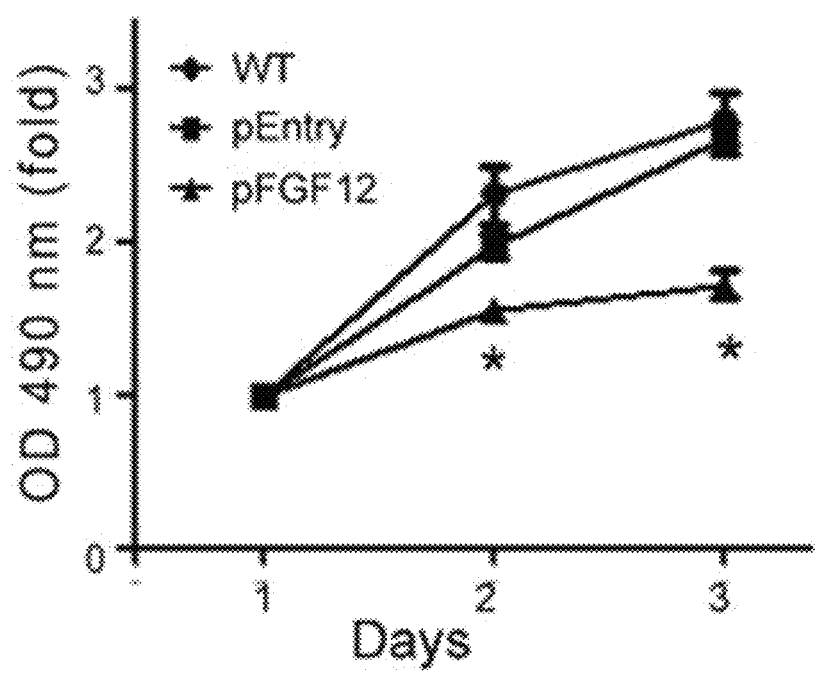

As a result of analysis of cell cycle state of cells, the proportion of cells in the G1 phase was remarkably high in FGF12-overexpressing HASMCs, compared with a control group (FIG. 6A and FIG. 6B). The MTS cell proliferation experiment results also showed that serum-induced or PDGF-BB-induced cell proliferation was remarkably inhibited in FGF12-overexpressing HASMCs. In addition, the PDGF-BB-induced cell proliferation was also remarkably inhibited in HPASMCs transfected to overexpress FGF12 (FIG. 6E).

The above experimental results show that the overexpression of FGF12 is sufficient in inhibiting the proliferation of serum-induced or PDGF-BB-induced HASMCs and HPASMCs.

Figure 7:
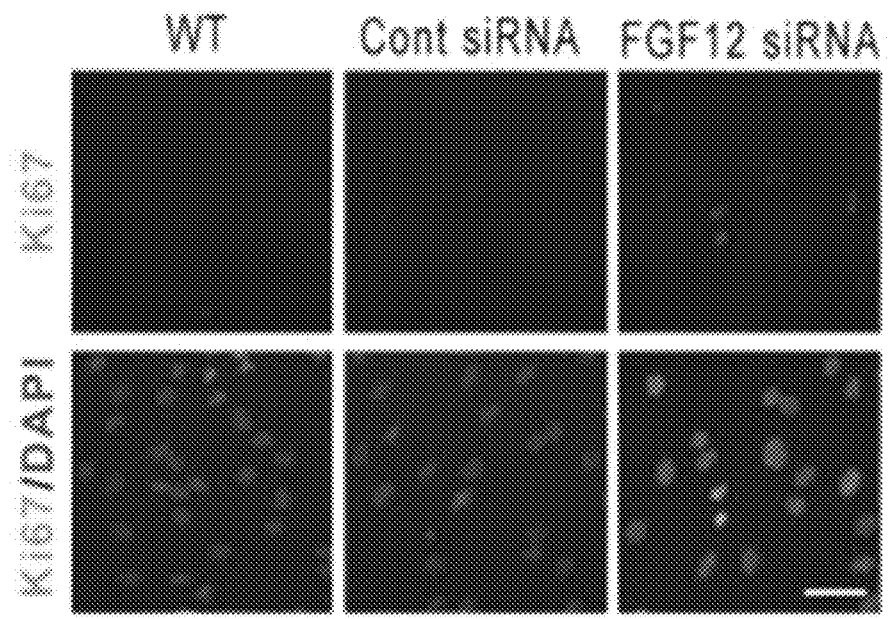
FIG. 7 shows immunofluorescent staining results of wild type (WT) or siRNA-transfected HASMCs (Cont siRNA, FGF12 siRNA) against the cell proliferation marker Ki67 (green). Cell nuclei were stained with DAPI (blue); and scale bar is 50 μm. Quantitative analysis of HASMCs stained against Ki67 was indicated as a bar graph below. For WT and pEntry, * indicates p<0.05 and n=5.
Figure 7:
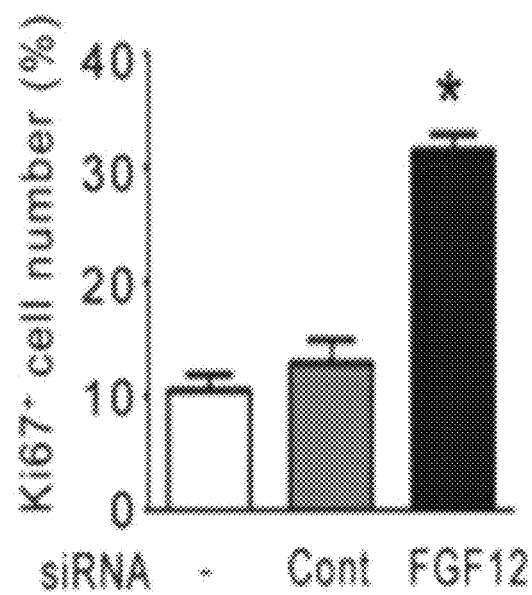

In addition, it was examined whether the FGF12 expression was essential in the inhibition of cell division in the resting phase of HASMCs. HASMCs were cultured in basal medium not containing either serum or PDGF-BB for 3 days. As a result of FGF12 expression inhibition using FGF12 siRNA and Ki67 staining under such starvation conditions, it was observed that cell proliferation was greatly increased in FGF12 siRNA-treated HASMCs (FIG. 7).

The above results verify that FGF12 expression is essential in the inhibition of cell division in the resting phase of starved HASMCs.

Example 4

Activation of p53 Signaling in Smooth Muscle Proliferation Inhibition by FGF12

4-1. p53 Expression Regulation by FGF12

In order to reveal molecular mechanisms of FGF12 to inhibit the cell proliferation of HASMCs, the functional relation between FGF12 and p53 was examined.

Figure 8A:
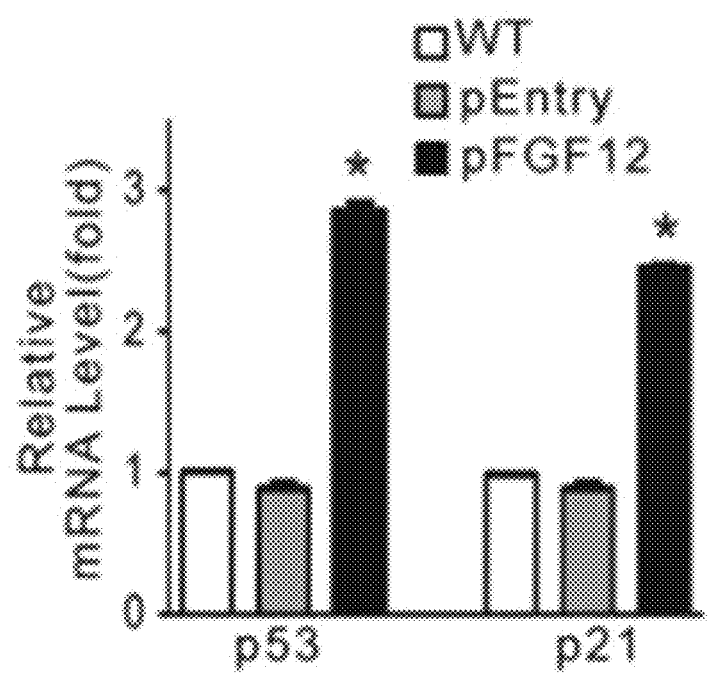
FIG. 8A, FIG. 8B, and FIG. 8C show experimental results illustrating the functional relation between FGF12-induced HASMC proliferation inhibition and p53.
Figure 8B:
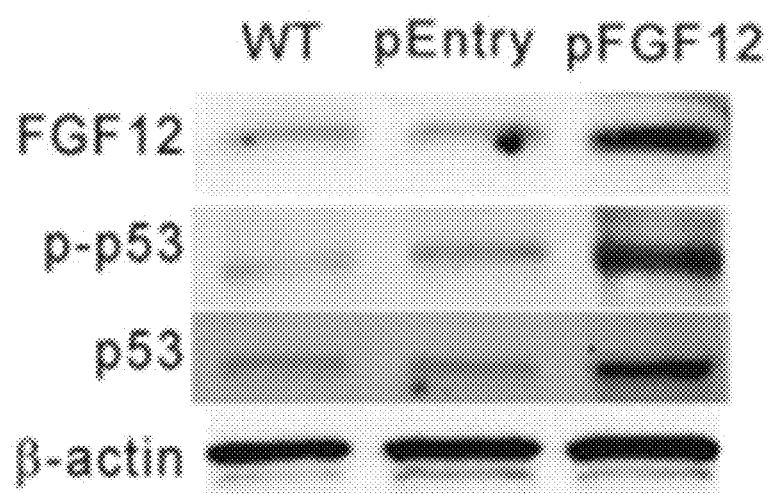
Figure 8C:
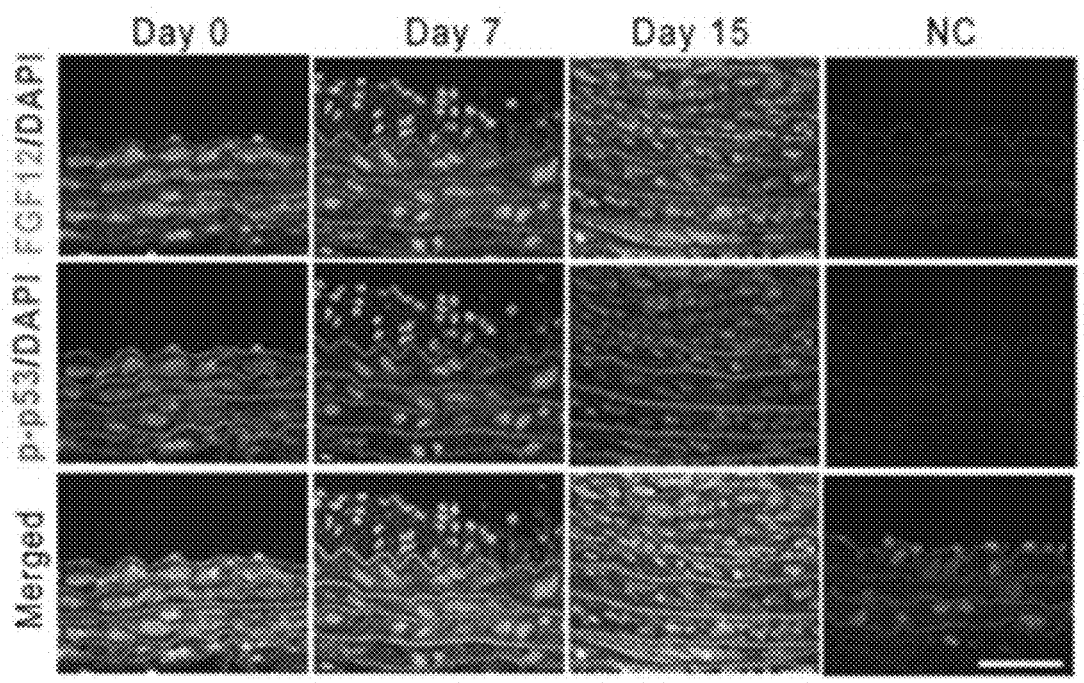

First, as a result of in-depth analysis of the microarray array in Example <3-1>, a plurality of genes (CDKN1A, CDK1, CCNE, BRCA1, CCNB1, MDM2), of which transcription is regulated by p53, are included in the DEGs of FGF12-overexpressing HASMCs, while FGF12 overexpression is likely to activate the p53 signaling system. As a result of RT-PCR, the mRNA levels of p53 and its direct transcriptional target p21 were greatly increased in FGF12-overexpressing HASMCs, compared with wild type (WT) HASMCs and empty vector (pEntry)-transfected HASMCs (FIG. 8A). It was also confirmed through Western blotting that the levels of p53 protein and phosphorylated p53 protein (p-p53) were greatly increased in FGF12-overexpressing HASMCs (FIG. 8B). It was shown that the expression profiles of FGF12 and p-p53 were also very similar in rat carotid artery injured tissue samples (FIG. 8C). A high level of p-p53 was detected in FGF12-expressing SMCs in the medial layers of the normal rat aorta (Day 0), but p-p53 was not detected in most SMCs not expressing FGF12 in the neointimal layers (Day 7). Meanwhile, on day 15 when SMCs express FGF12 in the neointimal layers, p-p53 was detected in the neointimal layers in many FGF12-expressing SMCs.

The above experimental results show that there is a close association between FGF12 expression and p53 expression in vascular smooth muscle cells.

4-2. Role of p53 in FGF12-Induced Cell Proliferation Inhibition

In order to reveal the p53 functions in the FGF12-induced inhibition of HASMC cell proliferation, the effect of p53 siRNA and p53 inhibitory compound on the inhibition of p53 signaling system and HASMC and HPASMC cell proliferation was examined.

Figure 9A:
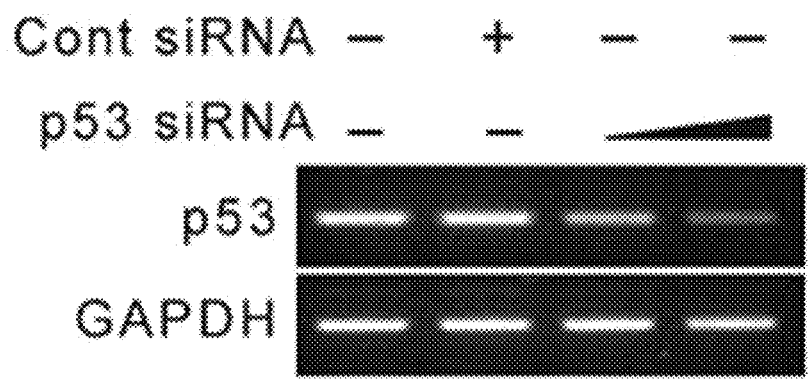
FIG. 9A, FIG. 9B, FIG. 9C, and FIG. 9D show experimental results illustrating the effect of p53 expression or dysfunction on HASMC proliferation.
Figure 9B:
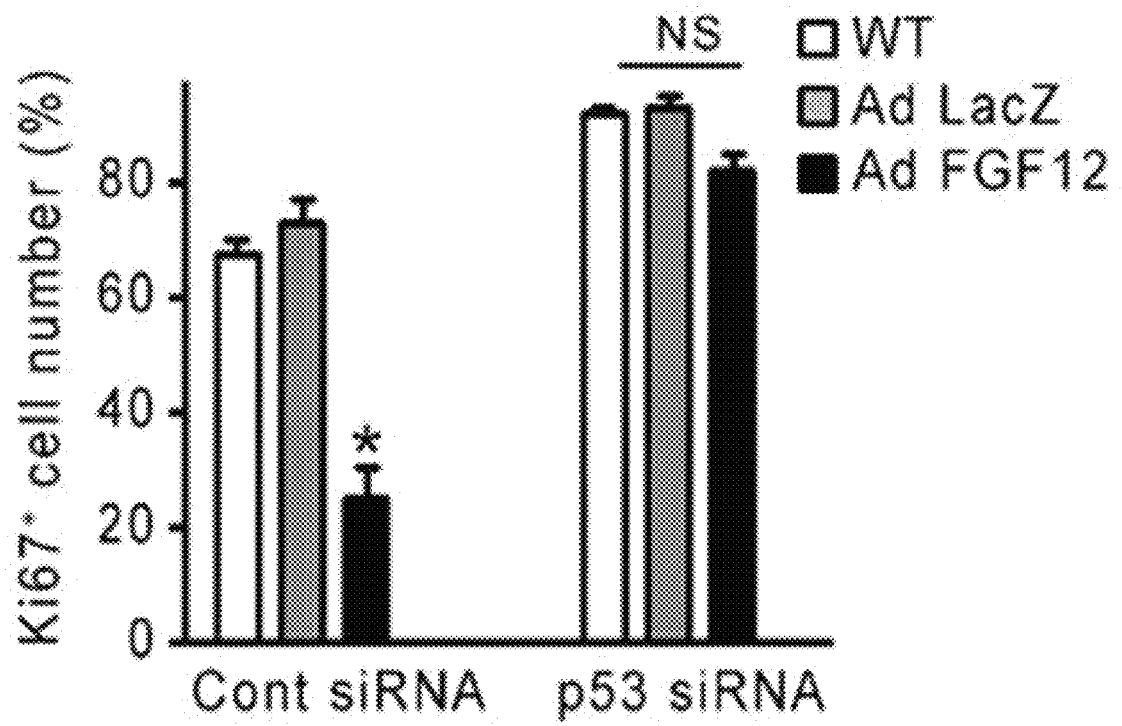
Figure 9C:
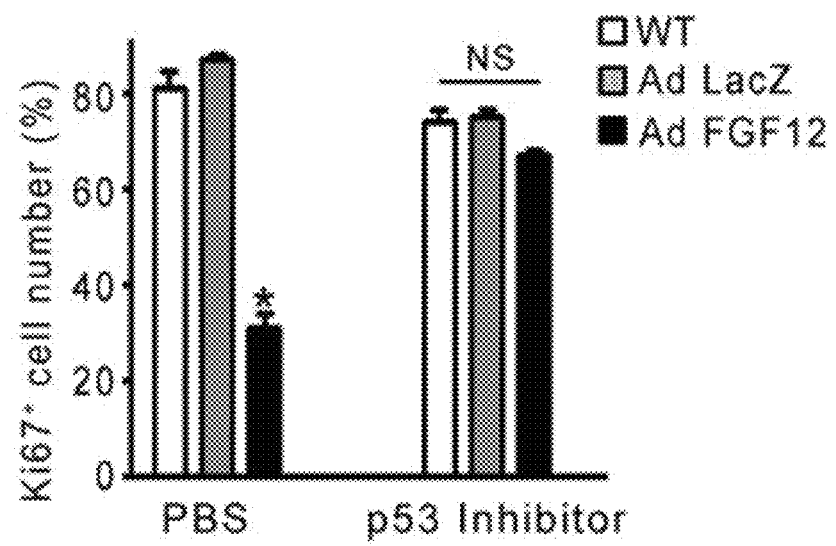
Figure 9D:
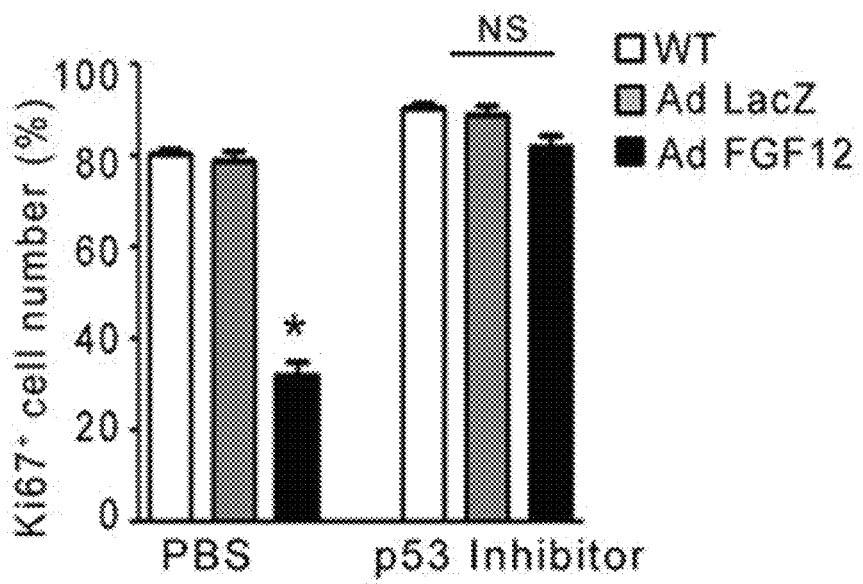

HASMCs transfected with FGF12-containing adenovirus (Ad-FGF12) were transfected with p53 siRNA, and the remarkable decrease in p53 mRNA level by p53 siRNA was then confirmed (FIG. 9A). The FGF12-induced cell proliferation inhibitory effect was also reduced in siRNA-mediated knockdown of p53 expression in HASMCs (FIG. 9B). Similarly, the p53 inhibitor pifithrin also exerted an effect of significantly improving the cell proliferation of Ad-FGF12-tranfected HASMCs (FIG. 9C). In addition, the p53 inhibitor pifithrin showed an effect of significantly improving the cell proliferation of Ad-FGF12-tranfected HPASMCs (FIG. 9D).

The above experimental results show that FGF12 promotes the expression and activation of p53 to inhibit the proliferation of HASMCs and HPASMCs.

Example 5

Therapeutic Effect of FGF12 Overexpression in In Vivo Vascular Injury

It was examined using carotid artery balloon injury models whether FGF12 overexpression could inhibit the vascular injury-induced neointima formation.

Figure 10A:
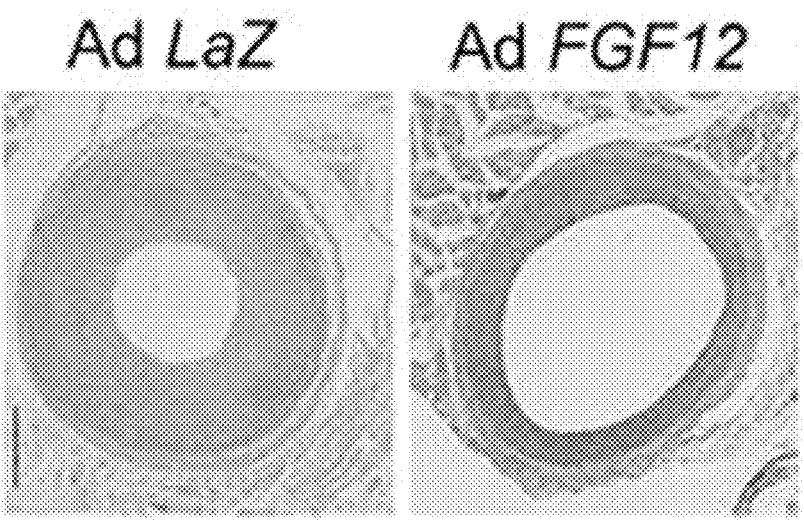
FIG. 10A, FIG. 10B, and FIG. 10C show experimental results illustrating the effect of FGF12 overexpression on neointimal formation.
Figure 10B:
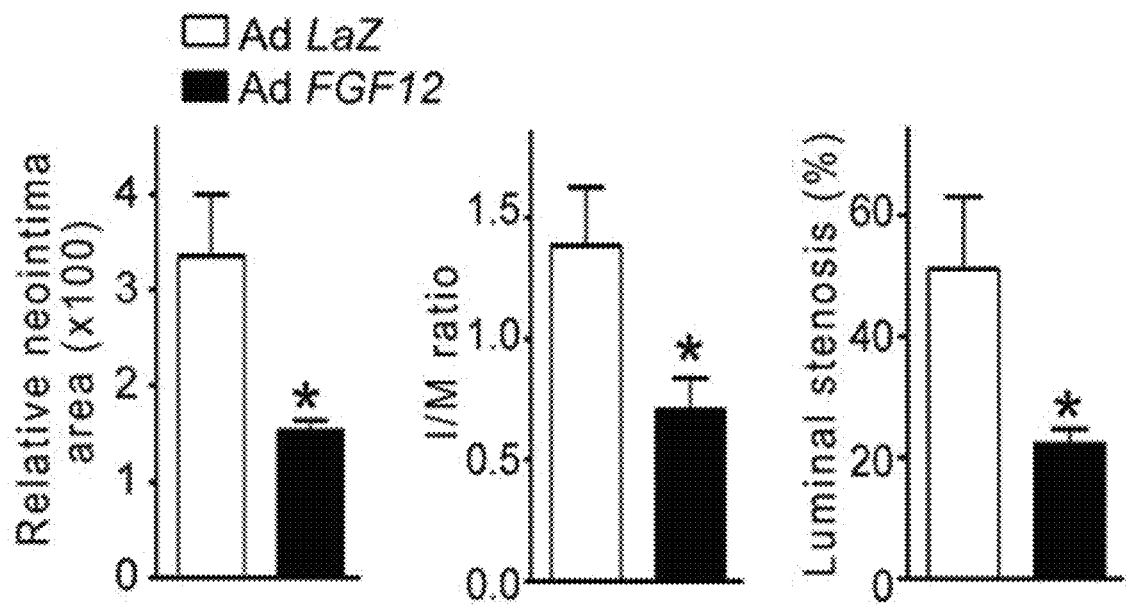
Figure 10C:
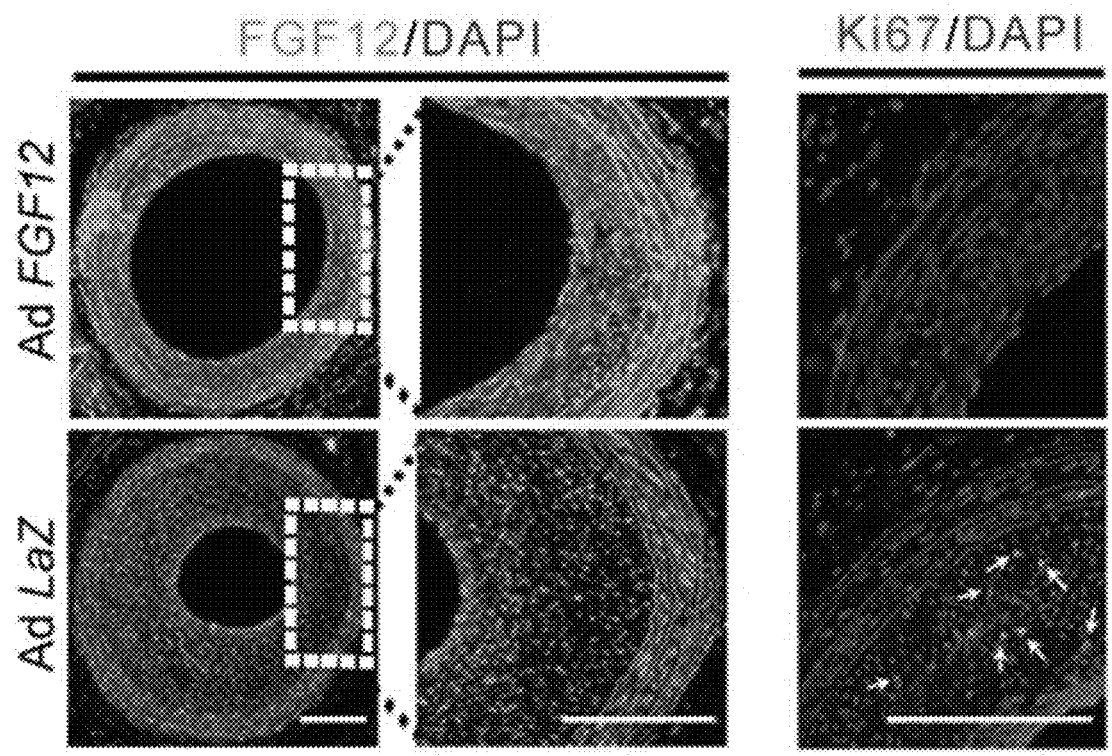

FGF12 was overexpressed in rats with balloon injured carotid arteries using adenovirus, and the change in the injured blood vessels was subjected to histological analysis (FIG. 10A to FIG. 10C). On day 14 after the balloon injury, the vascular wall transfected with Ad-FGF12 adenovirus was remarkably thin compared with the control vascular wall transfected with Ad-LacZ adenovirus (FIG. 10A). All the indicators of vascular injuries, such as the neointimal area, the intima/media ratio (I/M), and luminal stenosis (%), were remarkably decreased, and the neointima formation was overly reduced by about 50% (FIG. 10B). In addition, the vessels transfected with Ad-FGF12 adenovirus showed a greatly low number of Ki67-expressing cells compared with the control group, verifying a greatly low degrees of cell division and proliferation in comparison with the control group (FIG. 10C).

The above results show that the neointima formation of the injured vessels can be inhibited by FGF12 overexpression in in vivo vessels.

Example 6

Effect of FGF12 Overexpression on Vascular Endothelial Cell Proliferation

The effect of FGF12 on the proliferation of vascular endothelial cells was examined.

FGF12 was overexpressed in human umbilical vein endothelial cells (HUVECs) or human aortic smooth muscle cells (hASMCs) using adenoviruses, and the immunofluorescent staining was then performed on the cell proliferation marker Ki67 protein.

Figure 11A:
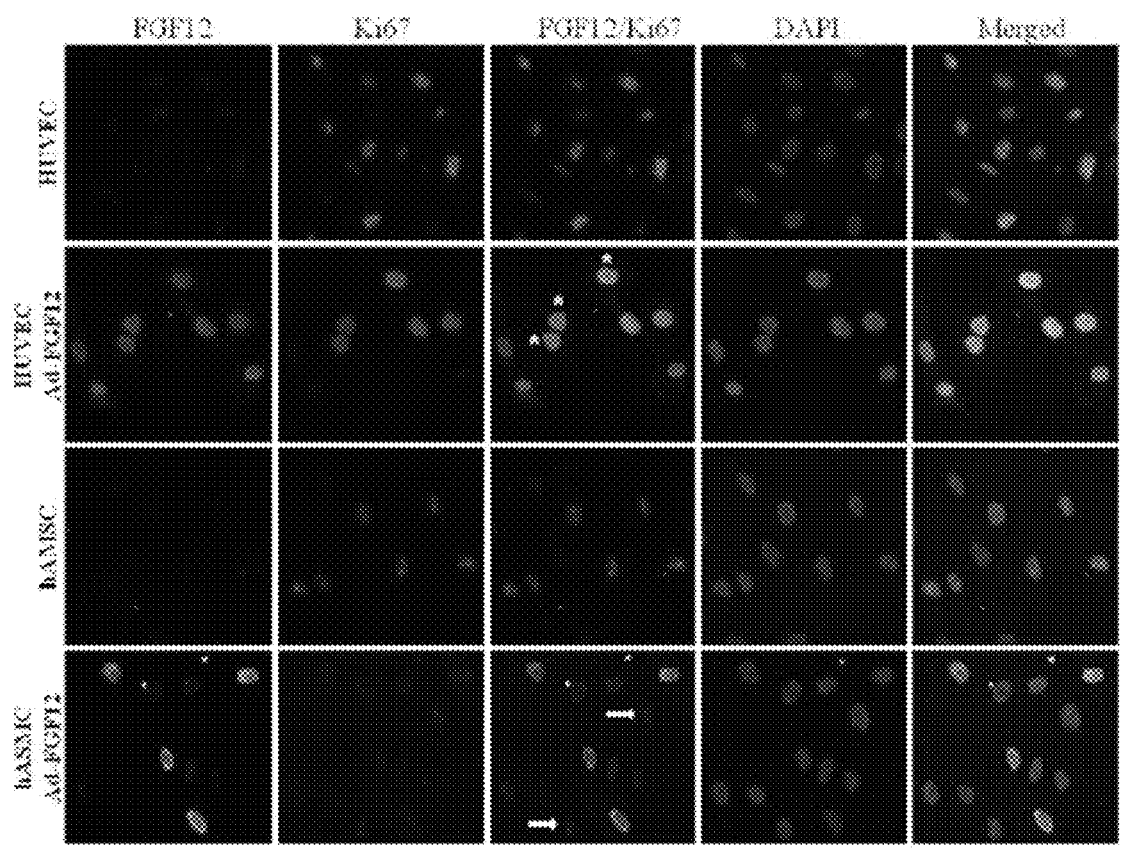
FIG. 11A and FIG. 11B show experimental results illustrating the effect of overexpression of FGF12 on the proliferation of human vascular smooth muscle cells and vascular endothelial cells.
Figure 11B:
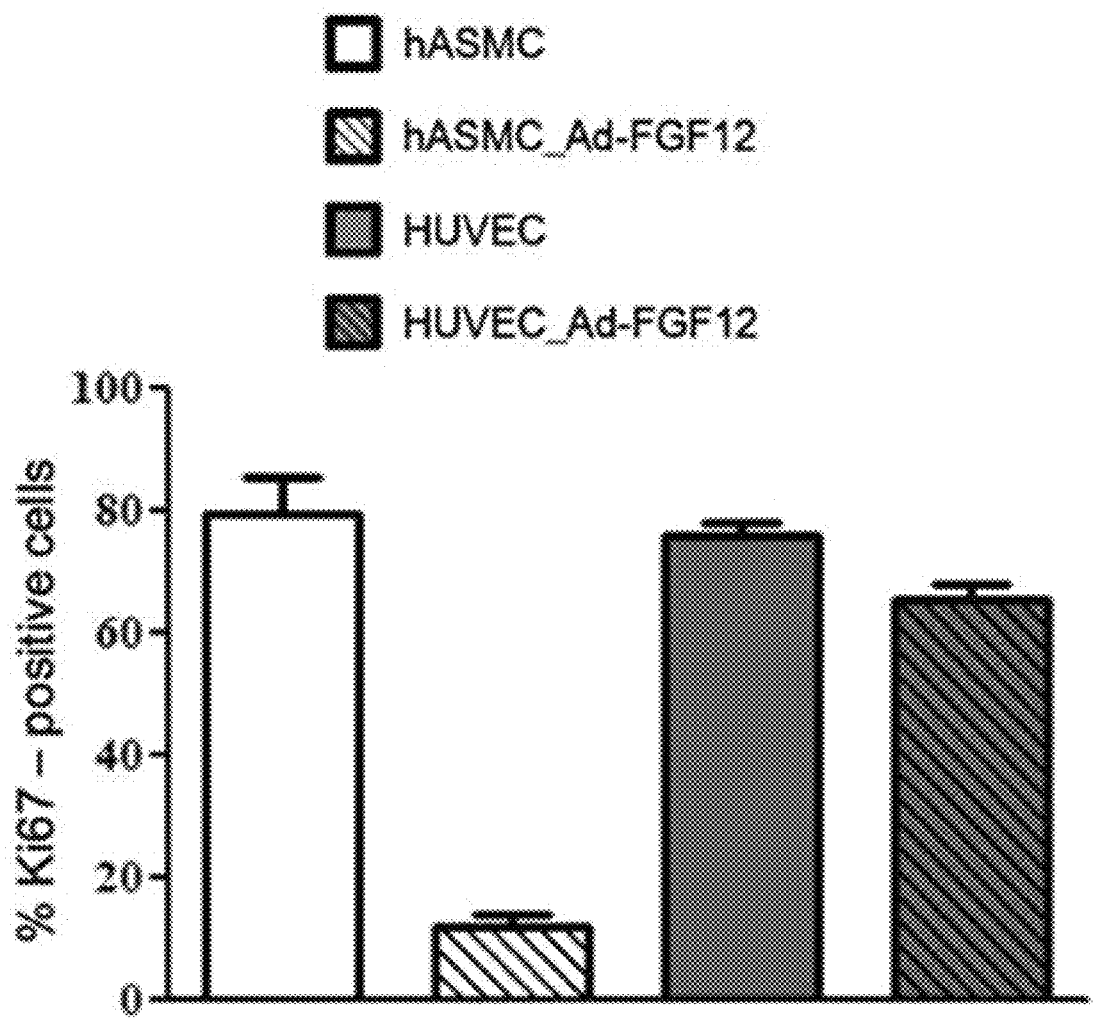

As a result, as confirmed in the above examples, the FGF12 overexpression was observed to remarkably reduce cell division and proliferation in human aortic smooth muscle cells (hASMCs) (FIG. 11A and FIG. 11B). The number of Ki67-expressing cells undergoing division for each type of cells is shown in FIG. 11B. Ad-FGF12-transfected hASMCs showed a remarkably reduced number of Ki67-expressing cells in comparison with virus-untransfected cells, while most of the Ki67-expressing cells do not express FGF12 (FIG. 11A, hASMC Ad-FGF12, cells indicated by white arrows). On the contrary, even though FGF12 was overexpressed in HUVECs transfected with Ad-FGF12, the number of Ki67-expressing cells in the HUVECs was not greatly different from that in the virus-untransfected cells. Especially, cells expressing both FGF12 and Ki67 at high levels were observed in Ad-FGF12-transfected HUVECs (FIG. 11A, HUVEC_Ad-FGF12, cells indicated by white mark *), and thus the expression of FGF12 did not affect the division of endothelial cells.

The above experimental results show that FGF12 exhibits a cell proliferation inhibitory effect specifically in vascular smooth muscle cells, with no effect of inhibiting the division and proliferation of vascular endothelial cells.

Example 7

Regulation of FGF12 Expression by BMP, an Agent for Promoting the Differentiation and Inhibiting the Proliferation of Pulmonary Vascular Smooth Muscle Cells It was verified whether the expression of FGF12 was regulated by bone morphogenetic protein (BMP), which is a potent agent for promoting the differentiation and inhibiting the proliferation of vascular smooth muscle cells.

Figure 12A:
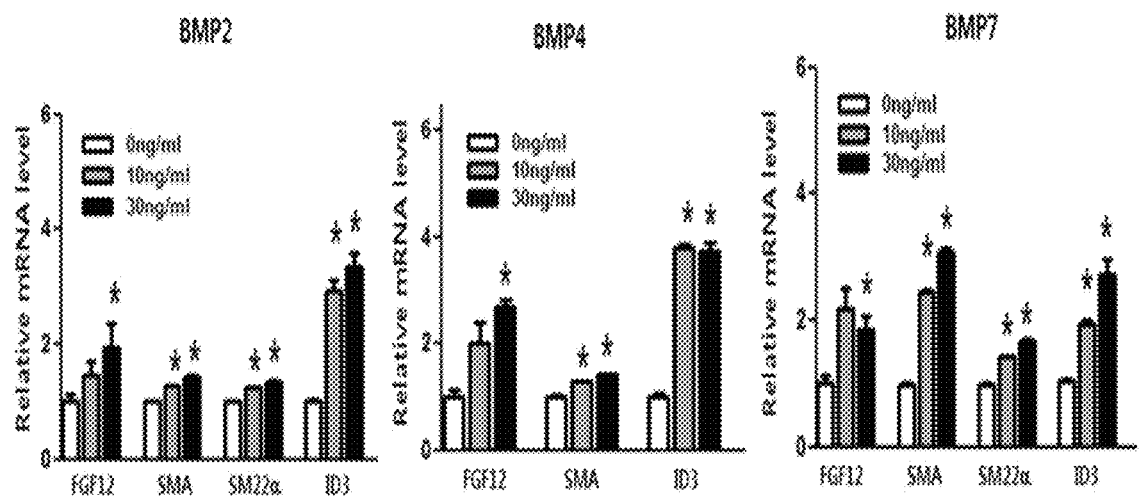
FIG. 12A, FIG. 12B, and FIG. 12C are experimental results showing that the expression of FGF12 in HPASMC is regulated by BMP.
Figure 12B:
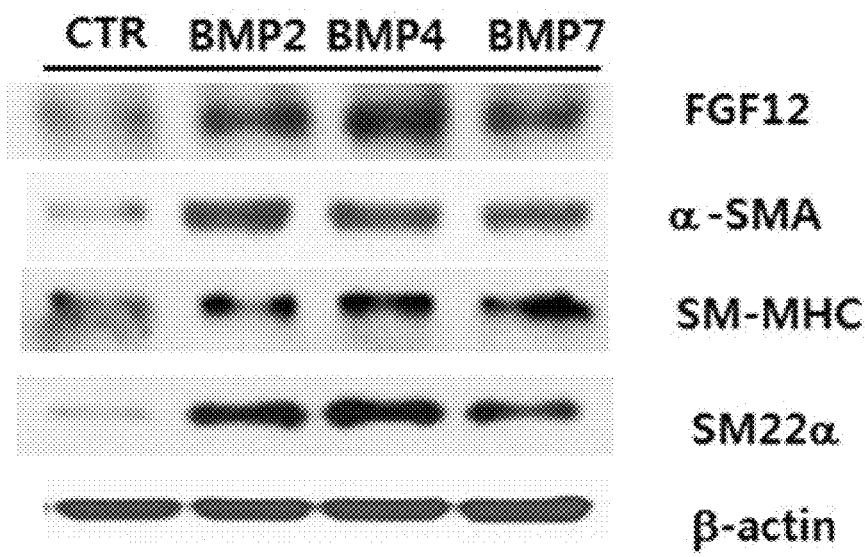
Figure 12C:
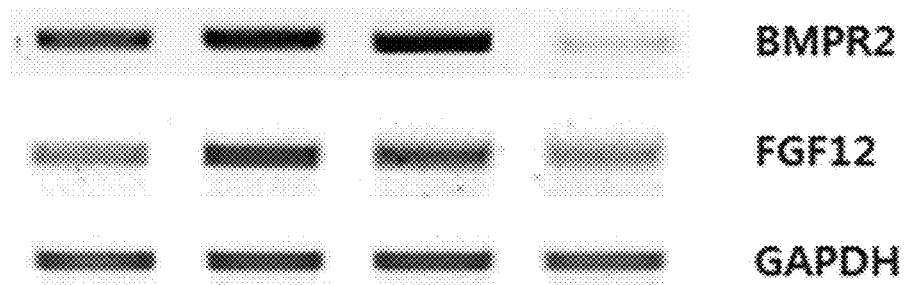

RT-PCR confirmed that the level of FGF12 mRNA was significantly increased in HPASMC (human pulmonary aortic vascular smooth muscle cell) 48 hours after the addition of BMP-2, BMP-4 and BMP-7 to the basal medium, respectively (FIG. 12A). The expression of the vascular smooth muscle cell differentiation marker genes ($\alpha$-SMA, SM22$\alpha$) was increased by BMP, respectively, while the expression of ID3 gene, which is known to increase by an activated BMP signaling, was also elevated (FIG. 12A). These results were also verified by western blotting analysis that the expression of vascular smooth muscle cell differentiation markers ($\alpha$-SMA, SM22$\alpha$) and FGF12 protein was increased by BMP-2, BMP-4 and BMP-7, respectively (FIG. 12B). In order to confirm whether the increased expression of FGF12 by BMP was a phenomenon caused by BMP receptor (BMPR2), the expression of BMPR2 was decreased by siRNA and followed by BMP treatment, leading to the significant reduction in the mRNA level of FGF12 gene (FIG. 12C). In other words, it was observed that BMP, which promotes the differentiation and inhibits the proliferation of vascular smooth muscle cells, increases the expression of FGF12 in HPASMC through BMPR2 signaling.

Example 8

Evaluation on BMP-Mediated Pulmonary Vascular Smooth Muscle Cell Differentiation and Proliferation Regulatory Mediating Function of FGF12

8-1. Disruption of the Activity of BMP in Promoting Differentiation by the Reduced Expression of FGF12

Figure 13A:
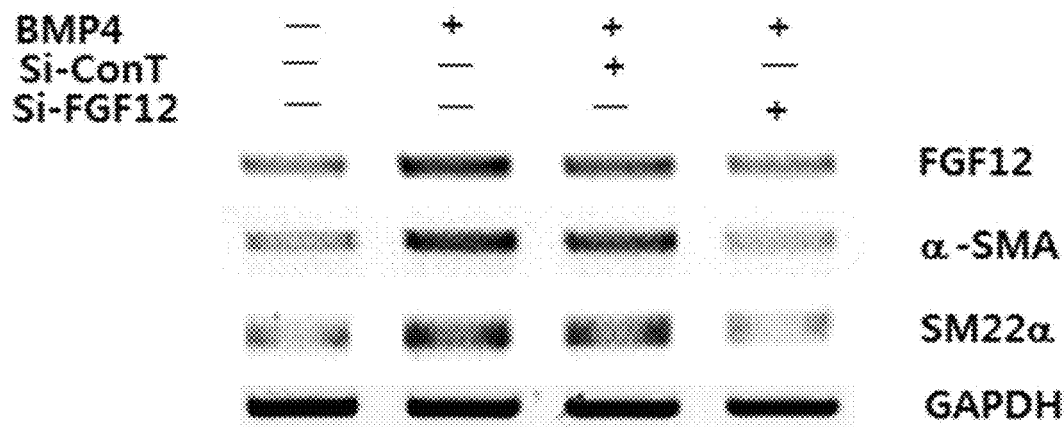
FIG. 13A, FIG. 13B, FIG. 13C and FIG. 13D are experimental results showing that the expression of FGF12 regulates the differentiation of HPASMC by BMP.
Figure 13B:
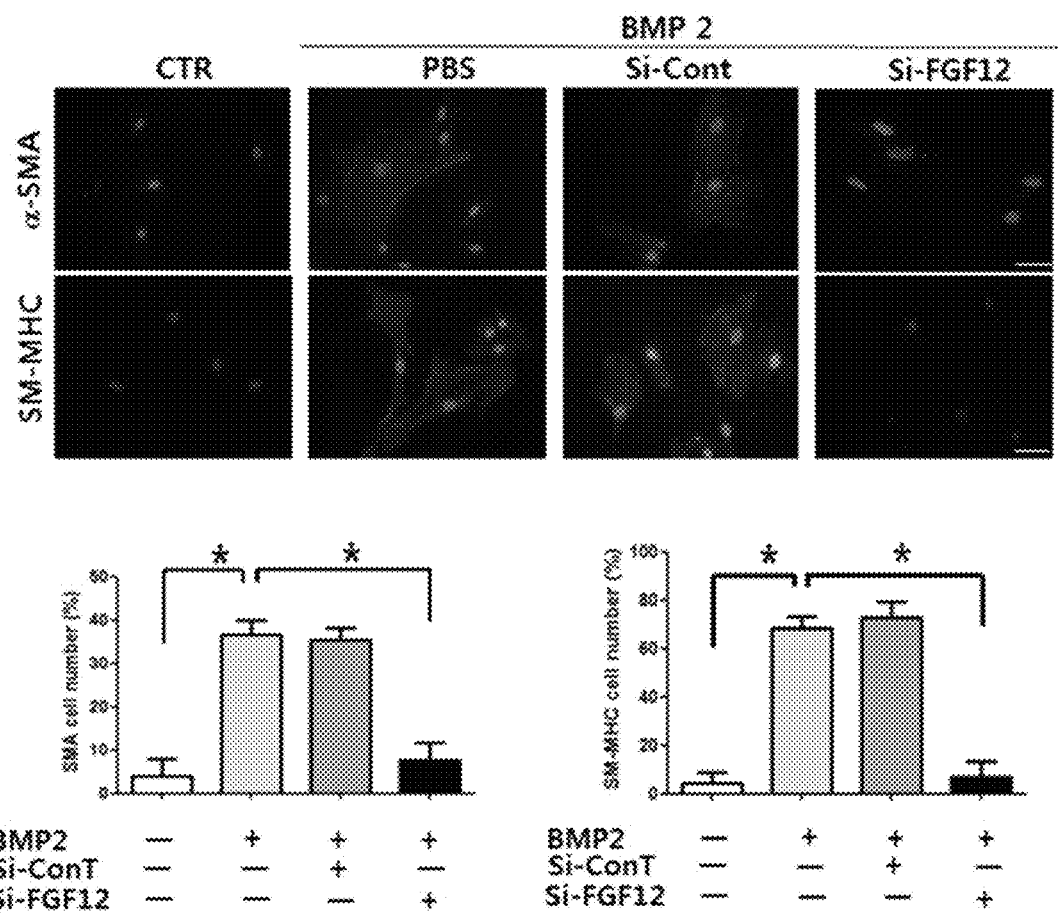
Figure 13C:
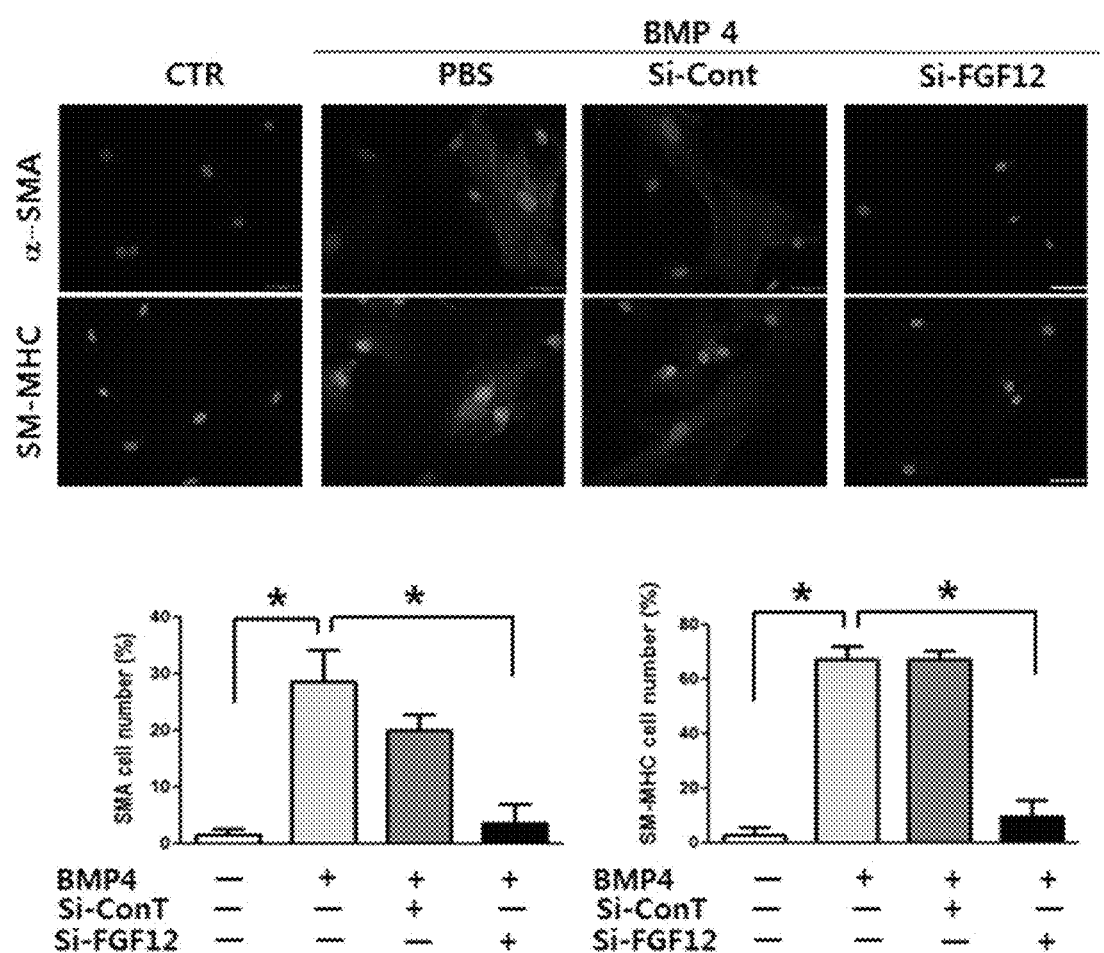
Figure 13D:
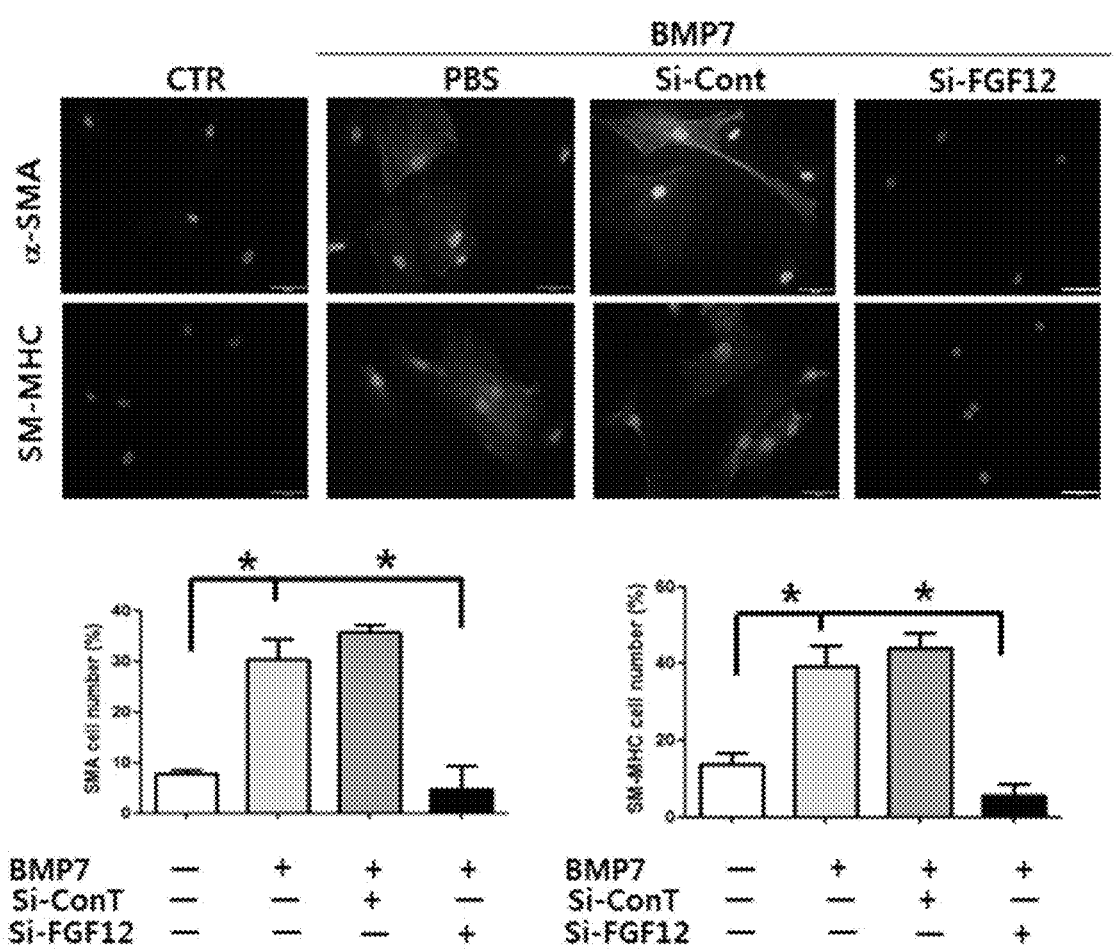

First, the expression of FGF12 was reduced in HPASMC using siRNA in order to confirm whether FGF12 regulates the differentiation of pulmonary vascular smooth muscle cells by BMP (FIG. 13A). PBS or siRNA-transformed HPASMC [Cont siRNA (si-Cont), FGF12 siRNA (si-FGF12)] were cultured for 1 day in medium containing BMP-2, BMP-4 and BMP-7, respectively, followed by measuring the protein expression of the smooth muscle cell (SMC) differentiation marker genes ($\alpha$-SMA, SM22$\alpha$). As a result, it was found that the expression of the differentiation marker genes of vascular smooth muscle cells was significantly reduced by BMP in HPASMC wherein the expression of FGF12 was reduced (FIG. 13B, FIG. 13C and FIG. 13D).

8-2. Disruption of the Activity of BMP in Inhibiting Proliferation by the Reduced Expression of FGF12

Figure 14:
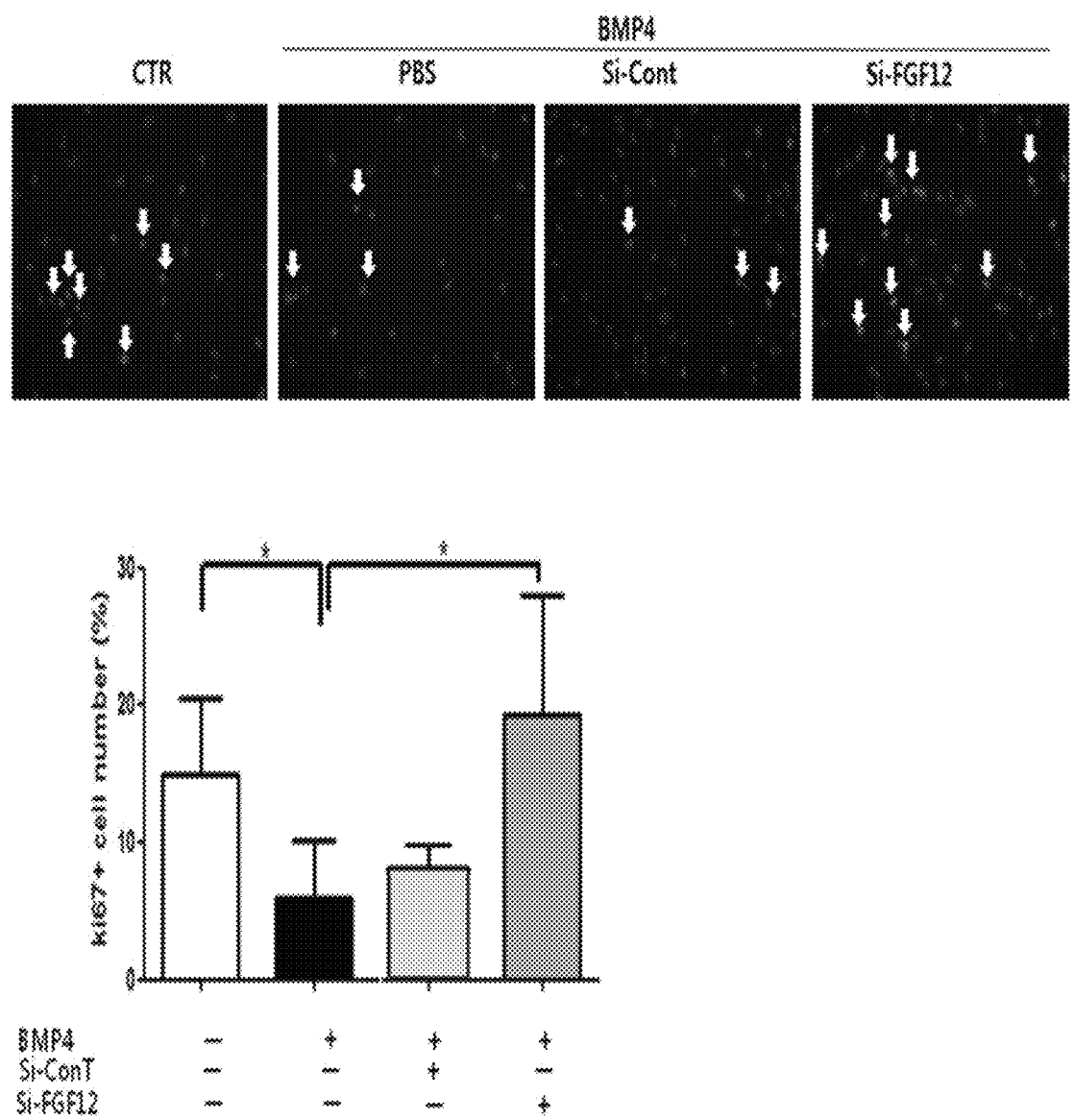
FIG. 14 is immunofluorescence staining results showing the stained Ki67 (green), a cellular marker of proliferation, after PBS- or siRNA-transformed HPASMC (si-Cont, si-FGF12) were cultured for 2 days in a basal medium with or without BMP-4 (100 ng/ml), indicating that the expression of FGF12 regulates the proliferation of HPASMC by BMP.

In addition, it was evaluated whether the expression of FGF12 regulates the inhibitory activity of BMP in the proliferation of pulmonary vascular smooth muscle cells. The expression of FGF12 in HPASMC was reduced using siRNA, followed by culture for 2 days in medium containing BMP4, and then Ki67 staining to measure the number of proliferating Ki67-positive cells (arrowheads). As a result, the decreased expression of FGF12 gene through FGF12 siRNA suppressed the inhibitory effect of BMP-4 on vascular smooth muscle cell proliferation (FIG. 14). These results show that the expression of FGF12 is essential for promoting the differentiation and inhibiting the proliferation of HPASMC by BMP.

Example 9

Therapeutic Effect of the Over-Expression of FGF12 in Pulmonary Arterial Hypertension The inventors investigated whether the over-expression of FGF12 could inhibit dedifferentiation and abnormal proliferation of vascular smooth muscle cells in pulmonary hypertension, by using animal model with monocrotaline (MCT).

FGF12 was over-expressed in the lungs using adenovirus in the rat after two weeks of monocrotaline administration, and changes in the blood vessels of the lung tissues were analyzed immunohistologically after 3 weeks of adenovirus administration (FIG. 15A, FIG. 15B and FIG. 15C). In the pulmonary artery where the over-expression of FGF12 was induced using adenovirus two weeks after monocrotaline-induced pulmonary arterial hypertension, it was observed that the thickness of the vascular endothelial and mesenchymal walls composed of vascular smooth muscle cells was markedly reduced, resulting in the enlarged vascular diameter (FIG. 15A). Furthermore, the overexpression of FGF12 protein was confirmed in pulmonary artery blood vessels through immuno-staining analysis, while the expression of α-SMA, a blood vessel smooth muscle cell differentiation marker, was elevated in a similar manner to that of normal pulmonary artery blood vessels (FIG. 15B).

In addition, as a result of measuring the right ventricular hypertrophy caused by pulmonary arterial hypertension, it was confirmed that the weight ratio of right ventricle/left ventricle in the FGF12-overexpressed rat via adenovirus was significantly lower than that of PBS or adenovirus LacZ-administered rat (FIG. 15C).

These results indicate that the over-expression of FGF12 is effective in the treatment of pulmonary arterial hypertension.

What is claimed is:

1. A method for treating a subject with a vascular smooth muscle cell proliferative disease, the method comprising administering to the subject an effective amount of a composition comprising a recombinant expression vector comprising a polynucleotide encoding FGF12 and an expression control sequence operatively linked thereto, thereby treating the vascular smooth muscle cell proliferative disease in the subject,
   wherein the vascular smooth muscle cell proliferative disease is vascular restenosis, and/or pulmonary arterial hypertension,
   wherein the recombinant expression vector is in a recombinant adenovirus vector or adeno-associated virus (AAV) vector,
   wherein the effective amount of the composition is administered to the subject via a direct local administration or an intratracheal administration, and
   wherein the polynucleotide encoding FGF12 comprises the nucleotide sequence of SEQ ID NO: 1 or SEQ ID NO: 3.

2. A method for treating a subject with a vascular smooth muscle cell proliferative disease, the method comprising administering to the subject an effective amount of a composition comprising FGF12 protein, thereby treating the vascular smooth muscle cell proliferative disease in the subject,
   wherein the vascular smooth muscle cell proliferative disease is vascular restenosis, and/or pulmonary arterial hypertension,
   wherein the effective amount of the composition is administered to the subject via a direct local administration or an intratracheal administration, and
   wherein the FGF12 protein comprises the amino acid sequence of SEQ ID NO: 2 or SEQ ID NO: 4.

3. A method for diagnosing a smooth muscle cell proliferative disease and treating a subject with the smooth muscle cell proliferative disease, the method comprising:
 (a) obtaining a vascular sample from the subject;
 (b) measuring the expression level of FGF12 in the sample; and
 (c) comparing the measured expression level of FGF12 of the subject with that of a healthy subject;
 (d) diagnosing the subject with the vascular smooth muscle cell proliferative disease when the expression level of FGF12 in the sample of the subject is lower than that of the healthy subject; and
 (e) administering a therapeutic composition to a subject diagnosed with the vascular smooth muscle cell proliferative disease by direct administration or intratracheal administration,
 wherein the vascular smooth muscle cell proliferative disease is vascular restenosis, and/or pulmonary arterial hypertension;
 wherein the therapeutic composition comprises (i) a recombinant expression vector comprising a polynucleotide encoding FGF12 and an expression control sequence operatively linked thereto, or (ii) FGF12 protein,
 wherein the polynucleotide encoding FGF12 comprises the nucleotide sequence of SEQ ID NO: 1 or SEQ ID NO: 3, and
 wherein the FGF12 protein comprises the amino acid sequence of SEQ ID NO: 2 or SEQ ID NO: 4.

4. The method of claim 3, wherein the expression level of FGF12 in step (b) is the expression level of FGF12 mRNA.

5. The method of claim 3, wherein the expression level of FGF12 in step (b) is the expression level of FGF12 protein.

6. The method of claim 3, wherein the expression level of FGF 12 in step (b) is measured by using a probe or a primer set specifically binding to the FGF12 mRNA.

7. The method of claim 6, wherein the FGF12 mRNA comprises the nucleotide sequence of SEQ ID NO: 1 or SEQ ID NO: 3.

8. The method of claim 6, wherein the primer set is the primer set of SEQ ID NO: 15 and SEQ ID NO: 16.

9. The method of claim 3, wherein the expression level of FGF12 in step (b) is measured by using an antibody specifically binding to the FGF12 protein.

10. The method of claim 9, wherein the FGF12 protein comprises the amino acid sequence of SEQ ID NO: 2 or SEQ ID NO: 4.

* * * * *